(12) United States Patent
Wähling et al.

(10) Patent No.: US 7,700,552 B2
(45) Date of Patent: Apr. 20, 2010

(54) MACROCYCLIC INHIBITORS OF HEPATITIS C VIRUS

(75) Inventors: Horst Wähling, Huddinge (SE); Bertil Samuelsson, Huddinge (SE)

(73) Assignee: Medivir AB, Huddinge (SE)

( * ) Notice: Subject to any disclaimer, the term of this patent is extended or adjusted under 35 U.S.C. 154(b) by 66 days.

(21) Appl. No.: 11/997,082

(22) PCT Filed: Jul. 28, 2006

(86) PCT No.: PCT/EP2006/007514

§ 371 (c)(1),
(2), (4) Date: Jan. 28, 2008

(87) PCT Pub. No.: WO2007/017144

PCT Pub. Date: Feb. 15, 2007

(65) Prior Publication Data

US 2009/0023758 A1     Jan. 22, 2009

(30) Foreign Application Priority Data

Jul. 29, 2005 (EP) ................................. 05107059

(51) Int. Cl.
| | | |
|---|---|---|
| A61K 38/00 | (2006.01) | |
| A01N 43/54 | (2006.01) | |
| A61K 31/517 | (2006.01) | |
| A61K 31/47 | (2006.01) | |
| C07D 401/00 | (2006.01) | |
| C07D 403/00 | (2006.01) | |
| C07D 413/00 | (2006.01) | |
| C07D 417/00 | (2006.01) | |
| C07D 419/00 | (2006.01) | |

(52) U.S. Cl. ................. 514/10; 514/266.2; 514/314; 544/284; 546/165

(58) Field of Classification Search .................. None
See application file for complete search history.

(56) References Cited

U.S. PATENT DOCUMENTS

| 7,041,814 B1 * | 5/2006 | Weinstock et al. ......... 536/24.1 |
| 7,125,845 B2 * | 10/2006 | Wu et al. ...................... 514/10 |
| 7,255,088 B2 * | 8/2007 | Nakamura et al. ........... 123/352 |
| 2007/0203072 A1 * | 8/2007 | Rosenquist et al. ........... 514/18 |

FOREIGN PATENT DOCUMENTS

| WO | WO 03/053349 | 7/2003 |
| WO | WO 2004/037855 | 5/2004 |
| WO | WO 2005/010029 | 2/2005 |
| WO | WO 2005/028501 | 3/2005 |
| WO | WO 2005/073195 | 8/2005 |
| WO | WO 2005/073216 | 8/2005 |

* cited by examiner

Primary Examiner—Cecilia Tsang
Assistant Examiner—Marcela M Cordero Garcia
(74) Attorney, Agent, or Firm—Birch, Stewart, Kolasch, & Birch LLP

(57) ABSTRACT

Compounds of the formula (I): and N-oxides, salts and stereoisomers thereof wherein A is $OR^1$, $NHS(=O)_pR^2$, $NHR^3$, NRaRb, $C(=O)NHR^3$ or $C(=O)NRaRb$ wherein; $R^1$ is hydrogen, $C_1$-$C_6$alkyl, $C_0$-$C_3$alkylenecarbocyclyl, $C_0$-$C_3$alkyleneheterocyclyl; $R^2$ is $C_1$-$C_6$alkyl, $C_0$-$C_3$alkylenecarbocyclyl, $C_0$-$C_3$alkyleneheterocyclyl or NRaRb; $R^3$ is $C_1$-$C_6$alkyl, $C_0$-$C_3$alkylenecarbocyclyl, $C_0$-$C_3$alkyleneheterocyclyl, —$OC_1$-$C_6$alkyl, —$OC_0$-$C_3$alkylenecarbocyclyl, —$OC_0$-$C_3$alkyleneheterocyclyl; wherein any alkyl, carbocyclyl or heterocyclyl in $R^1$, $R^2$ or $R^3$ are optionally substituted p is independently 1 or 2; n is 3, 4, 5 or 6; denotes an optional double bond; Rq is H or when L is CRz, Rq can also be $C_1$-$C_6$alkyl; Ry and Ry' are independently $C_1$-$C_6$alkyl; L is N or CRz; Rz is H or forms a double bond with the asterisked carbon; W is —$CH_2$—, —O—, —OC(=O)NH—, —OC(=O)—, —S—, —NH—, —NRa, —$NHS(=O)_2$—, —NHC(=0)NH— or —NHC(=O)—, —NHC(=S)NH— or a bond; $R^8$ is an optionally substituted ring system containing 1 or 2 saturated, partially saturated or unsaturated carbo or heterocyclic rings have utility in the inhibition of NS-3 serine proteases, such as flavivirus infections.

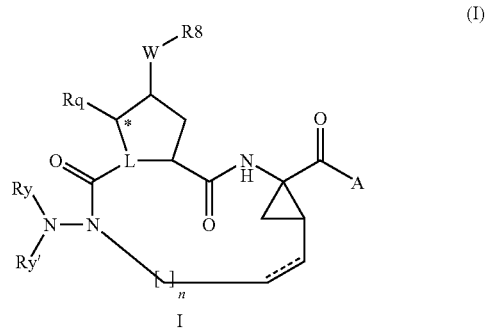

12 Claims, No Drawings

MACROCYCLIC INHIBITORS OF HEPATITIS C VIRUS

The present invention is concerned with macrocylic compounds having inhibitory activity on the replication of the hepatitis C virus (HCV). It further concerns compositions comprising these compounds as active ingredients as well as processes for preparing these compounds and compositions.

Hepatitis C virus is the leading cause of chronic liver disease worldwide and has become a focus of considerable medical research. HCV is a member of the Flaviviridae family of viruses in the *hepacivirus* genus, and is closely related to the *flavivirus* genus, which includes a number of viruses implicated in human disease, such as dengue virus and yellow fever virus, and to the animal pestivirus family, which includes bovine viral diarrhea virus (BVDV). HCV is a positive-sense, single-stranded RNA virus, with a genome of around 9,600 bases. The genome comprises both 5' and 3' untranslated regions which adopt RNA secondary structures, and a central open reading frame that encodes a single polyprotein of around 3,010-3,030 amino acids. The polyprotein encodes ten gene products which are generated from the precursor polyprotein by an orchestrated series of co- and posttranslational endoproteolytic cleavages mediated by both host and viral proteases. The viral structural proteins include the core nucleocapsid protein, and two envelope glycoproteins E1 and E2. The non-structural (NS) proteins encode some essential viral enzymatic functions (helicase, polymerase, protease), as well as proteins of unknown function. Replication of the viral genome is mediated by an RNA-dependent RNA polymerase, encoded by non-structural protein 5b (NS5B). In addition to the polymerase, the viral helicase and protease functions, both encoded in the bifunctional NS3 protein, have been shown to be essential for replication of HCV RNA. In addition to the NS3 serine protease, HCV also encodes a metalloproteinase in the NS2 region.

Following the initial acute infection, a majority of infected individuals develop chronic hepatitis because HCV replicates preferentially in hepatocytes but is not directly cytopathic. In particular, the lack of a vigorous T-lymphocyte response and the high propensity of the virus to mutate appear to promote a high rate of chronic infection. Chronic hepatitis can progress to liver fibrosis leading to cirrhosis, end-stage liver disease, and HCC (hepatocellular carcinoma), making it the leading cause of liver transplantations.

There are 6 major HCV genotypes and more than 50 subtypes, which are differently distributed geographically. HCV type 1 is the predominant genotype in Europe and the US. The extensive genetic heterogeneity of HCV has important diagnostic and clinical implications, perhaps explaining difficulties in vaccine development and the lack of response to therapy.

Transmission of HCV can occur through contact with contaminated blood or blood products, for example following blood transfusion or intravenous drug use. The introduction of diagnostic tests used in blood screening has led to a downward trend in post-transfusion HCV incidence. However, given the slow progression to the end-stage liver disease, the existing infections will continue to present a serious medical and economic burden for decades.

Current HCV therapies are based on (pegylated) interferon-alpha (IFN-α) in combination with ribavirin. This combination therapy yields a sustained virologic response in more than 40% of patients infected by genotype 1 viruses and about 80% of those infected by genotypes 2 and 3. Beside the limited efficacy on HCV type 1, this combination therapy has significant side effects and is poorly tolerated in many patients. Major side effects include influenza-like symptoms, hematologic abnormalities, and neuropsychiatric symptoms. Hence there is a need for more effective, convenient and better tolerated treatments.

Recently, two peptidomimetic HCV protease inhibitors have gained attention as clinical candidates, namely BILN-2061 disclosed in WO00/59929 and VX-950 disclosed in WO03/87092. A number of similar HCV protease inhibitors have also been disclosed in the academic and patent literature. It has already become apparent that the sustained administration of BILN-2061 or VX-950 selects HCV mutants which are resistant to the respective drug, so called drug escape mutants. These drug escape mutants have characteristic mutations in the HCV protease genome, notably D168V, D168Y and/or A165S. Accordingly, additional drugs with different resistance patterns are required to provide failing patients with treatment options, and combination therapy with multiple drugs is likely to be the norm in the future, even for first line treatment.

Experience with HIV drugs, and HIV protease inhibitors in particular, has further emphasized that sub-optimal pharmacokinetics and complex dosage regimes quickly result in inadvertent compliance failures. This in turn means that the 24 hour trough concentration (minimum plasma concentration) for the respective drugs in an HIV regime frequently falls below the $IC_{90}$ or $ED_{90}$ threshold for large parts of the day. It is considered that a 24 hour trough level of at least the $IC_{50}$, and more realistically, the $IC_{90}$ or $ED_{90}$, is essential to slow down the development of drug escape mutants. Achieving the necessary pharmacokinetics and drug metabolism to allow such trough levels provides a stringent challenge to drug design. The strong peptidomimetic nature of prior art HCV protease inhibitors, with multiple peptide bonds poses pharmacokinetic hurdles to effective dosage regimes.

There is a need for HCV inhibitors which may overcome the disadvantages of current HCV therapy such as side effects, limited efficacy, the emerging of resistance, and compliance failures.

The present invention concerns inhibitors of HCV replication which not only show good activity as HCV inhibitors but also exhibit improved cell permeability which also results in an enhanced bioavailability. This is contrary to the currently prevailing opinion which expects less active drugs with decreasing structural flexibility such as in less flexible macrocyclic rings. The compounds of the present invention having relatively low molecular weight are easy to synthesize, starting from starting materials that are commercially available or readily available through art-known synthesis procedures.

A first aspect of the invention provides compounds of the formula (I)

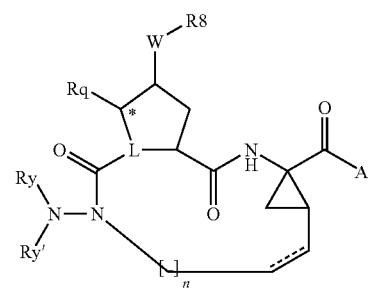

and N-oxides, salts, prodrugs, esters and stereoisomers thereof wherein

A is $OR^1$, $NHS(=O)_pR^2$, $NHR^3$, NRaRb, $C(=O)NHR^3$ or $C(=O)NRaRb$ wherein;

$R^1$ is hydrogen, $C_1$-$C_6$alkyl, $C_0$-$C_3$alkylenecarbocyclyl, $C_0$-$C_3$alkyleneheterocyclyl;

$R^2$ is $C_1$-$C_6$alkyl, $C_0$-$C_3$alkylenecarbocyclyl, $C_0$-$C_3$alkyleneheterocyclyl or NRaRb;

$R^3$ is $C_1$-$C_6$alkyl, $C_0$-$C_3$alkylenecarbocyclyl, $C_0$-$C_3$alkyleneheterocyclyl, —$OC_1$-$C_6$alkyl, —$OC_0$-$C_3$alkylenecarbocyclyl, —$OC_0$-$C_3$alkyleneheterocyclyl;

wherein any alkyl, carbocyclyl or heterocycylyl in $R^1$, $R^2$ or $R^3$ are optionally substituted with 1 to 3 substituents independently selected from the group consisting of halo, oxo, cyano, azido, nitro, $C_1$-$C_6$alkyl, $C_0$-$C_3$alkylenecarbocyclyl, $C_0$-$C_3$alkyleneheterocyclyl, —$C(=O)NH_2$, Y—NRaRb, Y—O—Rb, Y—$C(=O)$Rb, Y—$(C=O)$NRaRb, Y—NRaC$(=O)$Rb, Y—$NHSO_p$Rb, Y—$S(=O)_p$Rb and Y—$S(=O)_p$NRaRb, Y—$C(=O)$ORb, Y—NRaC$(=O)$ORb;

Y is independently a bond or $C_1$-$C_3$alkylene;

Ra is independently H, $C_1$-$C_6$alkyl or $C_1$-$C_6$alkoxy;

Rb is independently H, $C_1$-$C_6$alkyl, $C_1$-$C_6$alkoxy, $C_0$-$C_3$alkylenecarbocyclyl or $C_0$-$C_3$alkyleneheterocyclyl;

or Ra and Rb together with the nitrogen to which they are attached join to form a heterocyclyl group;

p is independently 1 or 2;

n is 3, 4, 5 or 6;

----- denotes an optional double bond;

Rq is H or when L is CRz, Rq can also be $C_1$-$C_6$alkyl;

Ry and Ry' are independently $C_1$-$C_6$alkyl;

L is N or CRz;

Rz is H or forms a double bond with the asterisked carbon;

W is —$CH_2$—, —O—, —$OC(=O)NH$—, —$OC(=O)$—, —S—, —NH—, —NRa, —$NHS(=O)_2$—, —$NHC(=O)NH$— or —$NHC(=O)$—, —$NHC(=S)NH$— or a bond;

$R^8$ is a ring system containing 1 or 2 saturated, partially saturated or unsaturated rings each of which has 4-7 ring atoms and each of which has 0 to 4 hetero atoms independently selected from S, O and N, the ring system being optionally spaced from W by a $C_1$-$C_3$ alkylene group; or $R^8$ is $C_1$-$C_6$alkyl; any of which $R^8$ groups can be optionally mono-, di-, or tri-substituted with $R^9$, wherein $R^9$ is independently selected from the group consisting of halo, oxo, cyano, azido, nitro, $C_1$-$C_6$alkyl, $C_0$-$C_3$alkylenecarbocyclyl, $C_0$-$C_3$alkyleneheterocyclyl, —$C(=O)NH_2$, Y—NRaRb, Y—O—Rb, Y—$C(=O)$Rb, Y—$(C=O)$NRaRb, Y—NRaC$(=O)$Rb, Y—$NHS(=O)_p$Rb, Y—$S(=O)_p$Rb, Y—$S(=O)_p$NRaRb, Y—$C(=O)$ORb, Y—NRaC$(=O)$ORb;

wherein said carbocyclyl or heterocyclyl is optionally substituted with one to three substituents selected from $R^{10}$; wherein $R^{10}$ is $C_1$-$C_6$alkyl, $C_3$-$C_7$cycloalkyl, $C_1$-$C_6$alkoxy, amino, amido, sulfonyl, ($C_1$-$C_3$ alkyl)sulfonyl, nitro, hydroxy, mercapto, halo, haloalkyl, carboxyl;

The invention further envisions compounds of the formula I represented by formula (It):

It the prodrugs, N-oxides, addition salts, quaternary amines, metal complexes, and stereochemically isomeric forms thereof, wherein the dashed line represents an optional double bond between atoms C7 and C8;

$Rt^1$ is aryl or a saturated, a partially unsaturated or completely unsaturated 5 or 6 membered monocyclic or 9 to 12 membered bicyclic heterocyclic ring system wherein said ring system contains one nitrogen, and optionally one to three additional heteroatoms selected from the group consisting of oxygen, sulfur and nitrogen, and wherein the remaining ring members are carbon atoms; wherein said ring system may be optionally substituted on any carbon or nitrogen ring atom with one, two, three, or four substituents each independently selected from $C_{3-7}$cycloalkyl, aryl, Het, —$C(=O)NRt^{5a}Rt^{5b}$, —$C(=O)Rt^7$, —$C(=O)OR^{6a}$, and $C_{1-6}$alkyl optionally substituted with $C_{3-7}$cycloalkyl, aryl, Het, —$C(=O)NRt^{5a}R^{5b}$, —$NRt^{5a}Rt^{5b}$, —$C(=O)Rt^7$, $NRt^{5a}C(=O)Rt^7$, —$NRt^{5a}SO_pRt^8$, —$SO_pRt^8$, —$SO_pNRt^{5a}Rt^{5b}$, —$C(=O)ORt^6$, or —$NRt^{5a}C(=O)OR^{6a}$; and wherein the substituents on any carbon atom of the heterocyclic ring may also be selected from $C_{1-6}$alkoxy, hydroxy, halo, polyhalo-$C_{1-6}$alkyl, $C_{1-6}$alkylthio, oxo, cyano, nitro, azido, —$NRt^{5a}Rt^{5b}$, —$NRt^{5a}C(=O)Rt^7$, —$NRt^{5a}SO_pRt^8$, —$SO_pRt^8$, —$SO_pNRt^{5a}Rt^{5b}$, —$C(=O)OH$, and —$NRt^{5a}C(=O)ORt^{6a}$;

Lt is a direct bond, —O—, —O—$C_{1-4}$alkanediyl-, —O—CO—, —O—$C(=O)$—$NRt^{5a}$— or —O—$C(=O)$—$NRt^{5a}$—$C_{1-4}$alkanediyl-;

X is N, CH, or C bearing a double bond to the asterisked carbon;

Rq is H, or when X is C may be $C_1$-$C_6$ alkyl;

Ry and Ry' are Ry and Ry' are independently $C_1$-$C_6$alkyl; or

Ry and Ry' together with the N atom to which they are attached form a saturated heterocyclic ring selected from pyrrolidinyl, piperidinyl, piperazinyl, 4-$C_1$-$C_6$alkylpiperazinyl, 4-$C_1$-$C_6$alkylcarbonylpiperazinyl or morpholinyl;

$Rt^2$ represents hydrogen, —$ORt^6$, —$C(=O)ORt^6$, —$C(=O)Rt^7$, —$C(=O)NRt^{5a}Rt^{5b}$, —$C(=O)NHRt^{5c}$, —$NRt^{5a}Rt^{5b}$, —$NHRt^{5c}$, —$NHSO_pNRt^{5a}Rt^{5b}$, —$NRt^{5a}SO_pRt^8$, or —$B(ORt^6)_2$;

n is 3, 4, 5 or 5;

p is 1 or 2;

each $Rt^{5a}$ and $Rt^{5b}$ are, independently, hydrogen, $C_{3-7}$cycloalkyl, aryl, Het, $C_{1-6}$alkyl optionally substituted with halo, $C_{1-6}$alkoxy, cyano, polyhalo$C_{1-6}$alkoxy, $C_{3-7}$cycloalkyl, aryl, or with Het;

$Rt^{5c}$ is $C_{3-7}$cycloalkyl, aryl, Het, —O—$C_{3-7}$cycloalkyl, —O-aryl, —O-Het, $C_{1-6}$alkyl, or $C_{1-6}$alkoxy, wherein said $C_{1-6}$alkyl or $C_{1-6}$alkoxy may be each optionally substituted with —C(=O)OR$t^6$, $C_{3-7}$cycloalkyl, aryl, or Het;

$Rt^6$ is hydrogen; $C_{2-6}$alkenyl; Het; $C_{3-7}$cycloalkyl optionally substituted with $C_{1-6}$alkyl; or $C_{1-6}$alkyl optionally substituted with $C_{3-7}$cycloalkyl or Het;

$Rt^{6a}$ is $C_{2-6}$alkenyl, $C_{3-7}$cycloalkyl, Het, or $C_{1-6}$alkyl optionally substituted with $C_{3-7}$cycloalkyl or Het;

$Rt^7$ is hydrogen, $C_{1-6}$alkyl, $C_{3-7}$cycloalkyl, or aryl;

$Rt^8$ is hydrogen, polyhalo$C_{1-6}$alkyl, aryl, Het, $C_{3-7}$cycloalkyl optionally substituted with $C_{1-6}$alkyl, or $C_{1-6}$alkyl optionally substituted with $C_{3-7}$cycloalkyl, aryl or Het;

aryl as a group or part of a group is phenyl, naphthyl, indanyl, or 1,2,3,4-tetrahydronaphthyl, each of which may be optionally substituted with one, two or three substituents selected from halo, $C_{1-6}$alkyl, polyhalo$C_{1-6}$alkyl, hydroxy, $C_{1-6}$alkoxy, polyhalo$C_{1-6}$alkoxy, $C_{1-6}$alkoxy$C_{1-6}$alkyl, carboxyl, $C_{1-6}$alkylcarbonyl, cyano, nitro, amino, mono- or di$C_{1-6}$alkylamino, azido, mercapto, $C_3$-$C_7$ cycloalkyl, (cyclopropyl), pyrrolidinyl, piperidinyl, piperazinyl, 4-$C_{1-6}$alkylpiperazinyl, 4-$C_{1-6}$alkylcarbonyl-piperazinyl, and morpholinyl; and Het as a group or part of a group is a 5 or 6 membered saturated, partially unsaturated or completely unsaturated heterocyclic ring containing 1 to 4 heteroatoms each independently selected from nitrogen, oxygen and sulfur, being optionally condensed with a benzene ring, and wherein the group Het as a whole may be optionally substituted with one, two or three substituents each independently selected from the group consisting of halo, $C_{1-6}$alkyl, polyhalo$C_{1-6}$alkyl, hydroxy, $C_{1-6}$alkoxy, polyhalo$C_{1-6}$alkoxy, $C_{1-6}$alkoxy$C_{1-6}$alkyl, carboxyl, $C_{1-6}$alkylcarbonyl, cyano, nitro, amino, mono- or di$C_{1-6}$alkylamino, $C_3$-$C_7$ cycloalkyl, (cyclopropyl), pyrrolidinyl, piperidinyl, piperazinyl, 4-$C_{1-6}$alkylpiperazinyl, 4-$C_{1-6}$alkylcarbonylpiperazinyl, and morpholinyl.

It will be apparent that in the alternative embodiment of the invention in the paragraph immediately above, that $Rt^1$ broadly corresponds to $R^8$, $Rt^2$ broadly corresponds to A, Lt broadly corresponds to W, aryl is broadly speaking embraced by $C_0$-$C_3$alkylenecarbocyclyl where $C_0$-$C_3$alkylene is zero (i.e. a bond) and Het is broadly speaking embraced by $C_0$-$C_3$alkylheterocyclyl, where $C_0$-$C_3$alkylene is zero (i.e. a bond). The preferments expressed below for formula (I) apply even to the corresponding values in formula (It) and references to formula (I) shall be construed as including the corresponding compounds of formula (It).

The invention further relates to methods for the preparation of the compounds of formula (I), the prodrugs, N-oxides, addition salts, quaternary amines, metal complexes, and stereochemically isomeric forms thereof, its intermediates, and the use of the intermediates in the preparation of the compounds of formula (I).

The invention relates to the compounds of formula (I) per se, the prodrugs, N-oxides, addition salts, quaternary amines, metal complexes, and stereochemically isomeric forms thereof, for use as a medicament. The invention further relates to pharmaceutical compositions comprising the aforementioned compounds for administration to a subject suffering from HCV infection. The pharmaceutical compositions may comprise combinations of the aforementioned compounds with other anti-HCV agents.

The invention also relates to the use of a compound of formula (I), or a prodrug, N-oxide, addition salt, quaternary amine, metal complex, or stereochemically isomeric forms thereof, for the manufacture of a medicament for inhibiting HCV replication. Or the invention relates to a method of inhibiting HCV replication in a warm-blooded animal said method comprising the administration of an effective amount of a compound of formula (I), or a prodrug, N-oxide, addition salt, quaternary amine, metal complex, or stereochemically isomeric forms thereof.

As used in the foregoing and hereinafter, the following definitions apply unless otherwise noted.

The term halo is generic to fluoro, chloro, bromo and iodo.

The term "halo$C_{1-6}$alkyl" as a group or part of a group, e.g. in halo-$C_{1-6}$alkoxy, is defined as mono- or polyhalo substituted $C_{1-6}$alkyl, in particular $C_{1-6}$alkyl substituted with up to one, two, three, four, five, six, or more halo atoms, such as methyl or ethyl with one or more fluoro atoms, for example, difluoromethyl, trifluoromethyl, trifluoroethyl. Preferred is trifluoromethyl. Also included are perfluoro$C_{1-6}$alkyl groups, which are $C_{1-6}$alkyl groups wherein all hydrogen atoms are replaced by fluoro atoms, e.g. pentafluoroethyl. In case more than one halogen atom is attached to an alkyl group within the definition of polyhalo$C_{1-6}$alkyl, the halogen atoms may be the same or different.

As used herein "$C_{1-4}$alkyl" as a group or part of a group defines straight or branched chain saturated hydrocarbon radicals having from 1 to 4 carbon atoms such as for example methyl, ethyl, 1-propyl, 2-propyl, 1-butyl, 2-butyl, 2-methyl-1-propyl; "$C_{1-6}$alkyl" encompasses $C_{1-4}$alkyl radicals and the higher homologues thereof having 5 or 6 carbon atoms such as, for example, 1-pentyl, 2-pentyl, 3-pentyl, 1-hexyl, 2-hexyl, 2-methyl-1-butyl, 2-methyl-1-pentyl, 2-ethyl-1-butyl, 3-methyl-2-pentyl, and the like. Of interest amongst $C_{1-6}$alkyl is $C_{1-4}$alkyl.

The term "$C_{2-6}$alkenyl" as a group or part of a group defines straight and branched chained hydrocarbon radicals having saturated carbon-carbon bonds and at least one double bond, and having from 2 to 6 carbon atoms, such as, for example, ethenyl (or vinyl), 1-propenyl, 2-propenyl (or allyl), 1-butenyl, 2-butenyl, 3-butenyl, 2-methyl-2-propenyl, 2-pentenyl, 3-pentenyl, 2-hexenyl, 3-hexenyl, 4-hexenyl, 2-methyl-2-butenyl, 2-methyl-2-pentenyl and the like. Of interest amongst $C_{2-6}$alkenyl is $C_{2-4}$alkenyl.

The term "$C_{2-6}$alkynyl" as a group or part of a group defines straight and branched chained hydrocarbon radicals having saturated carbon-carbon bonds and at least one triple bond, and having from 2 to 6 carbon atoms, such as, for example, ethynyl, 1-propynyl, 2-propynyl, 1-butynyl, 2-butynyl, 3-butynyl, 2-pentynyl, 3-pentynyl, 2-hexynyl, 3-hexynyl and the like. Of interest amongst $C_{2-6}$alkynyl is $C_{2-4}$alkynyl.

$C_{3-7}$cycloalkyl is generic to cyclopropyl, cyclobutyl, cyclopentyl, cyclohexyl and cycloheptyl.

$C_{0-3}$alkylene defines a bond ($C_0$) or bivalent straight and branched chain saturated hydrocarbon radicals having from 1 to 3 carbon atoms such as, for example, methylene, ethylene, 1,3-propanediyl, 1,2-propanediyl, and the like, especially methylene.

$C_{1-6}$alkoxy means $C_{1-6}$alkyloxy wherein $C_{1-6}$alkyl is as defined above.

As used herein before, the term (=O) or oxo forms a carbonyl moiety when attached to a carbon atom, a sulfoxide moiety when attached to a sulfur atom and a sulfonyl moiety when two of said terms are attached to a sulfur atom. Whenever a ring or ring system is substituted with an oxo group, the carbon atom to which the oxo is linked is a saturated carbon.

'Amino' unless the context suggests otherwise, includes $NH_2$, $NHC_1$-$C_6$alkyl or $N(C_1$-$C_6$-alkyl$)_2$, wherein in the definitions of amino each of the $C_1$-$C_6$ alkyl groups is especially $C_1$-$C_3$ alkyl s, or saturated cyclic amines such as pyrrolidinyl, piperidinyl, piperazinyl, 4-$C_1$-$C_6$alkylpiperazinyl, such as 4-methylpiperazinyl, 4-$C_1$-$C_6$alkylcarbonylpiperazinyl and morpholinyl.

'Amido' includes $C(=O)NH_2$, and alkylamido, such as $C(=O)NHC_1$-$C_6$alkyl, $C(=O)N(C_1$-$C_6$alkyl$)_2$ especially $C(=O)NHC_1$-$C_3$alkyl, $C(=O)N(C_1$-$C_3$alkyl$)_2$ or —NH$(C=O)C_1$-$C_6$alkyl, for example —NHC(=O)CH$(CH_3)_3$, including —NH(C=O)$C_1$-$C_3$alkyl.

'$C_0$-$C_3$alkylenearyl' as applied herein is meant to include an aryl moiety such as a phenyl, naphthyl or phenyl fused to a $C_3$-$C_7$cycloalkyl (for example indanyl), which aryl is directly bonded (i.e. $C_0$) or through an intermediate methyl, ethyl, or propyl group as defined for $C_1$-$C_3$alkylene above. Unless otherwise indicated the aryl and/or its fused cycloalkyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro $C_0$-$C_3$alkylcarbocyclyl, $C_0$-$C_3$alkylheterocyclyl, it being understood that the heterocyclic and carbocyclic moieties in the $C_0$-$C_3$alkylcarbocyclyl or $C_0$-$C_3$alkylheterocyclyl substituent may itself be substituted as provided herein, but typically not with a further $C_0$-$C_3$alkylcarbocyclyl or $C_0$-$C_3$alkylheterocyclyl. "Aryl" has the corresponding meaning, i.e. where the $C_0$-$C_3$alkyl linkage is absent.

'$C_0$-$C_3$alkylene$C_3$$C_7$cycloalkyl' as applied herein is meant to include a $C_3$-$C_7$cycloalkyl group such as cyclopropyl, cyclobutyl, cyclopentyl, cyclohexyl or cycloheptyl, which cycloalkyl is directly bonded (i.e. $C_0$alkyl) or through an intermediate methyl, ethyl, propyl or isopropyl group as defined for $C_1$-$C_3$alkylene above. The cycloalkyl group may contain an unsaturated bond. Unless otherwise indicated the cycloalkyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro $C_0$-$C_3$alkylcarbocyclyl, $C_0$-$C_3$alkylheterocyclyl, it being understood that the heterocyclic and carbocyclic moieties in the $C_0$-$C_3$alkylcarbocyclyl or $C_0$-$C_3$alkylheterocyclyl substituent may itself be substituted as provided herein, but typically not with a further $C_0$-$C_3$alkylcarbocyclyl or $C_0$-$C_3$alkylheterocyclyl.

'$C_0$-$C_3$alkylcarbocyclyl' as applied herein is meant to include CO—$C_3$alkylaryl and $C_0$-$C_3$alkyl$C_3$-$C_7$cycloalkyl. Unless otherwise indicated the aryl or cycloalkyl group is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro, $C_0$-$C_3$alkylcarbocyclyl and/or $C_0$-$C_3$alkylheterocyclyl, it being understood that the heterocyclic and carbocyclic moieties in the $C_0$-$C_3$alkylcarbocyclyl or $C_0$-$C_3$alkylheterocyclyl substituent may itself be substituted as provided herein, but typically not with a further $C_0$-$C_3$alkylcarbocyclyl or $C_0$-$C_3$alkylheterocyclyl. "Carbocyclyl" has the corresponding meaning, i.e. where the $C_0$-$C_3$alkyl linkage is absent '$C_0$-$C_3$alkyleneheterocycylyl' as applied herein is meant to include a monocyclic, saturated or unsaturated, heteroatom-containing ring such as piperidinyl, morpholinyl, piperazinyl, pyrazolyl, imidazolyl, oxazolyl, isoxazolyl, thiazinolyl, isothiazinolyl, thiazolyl, oxadiazolyl, 1,2,3-triazolyl, 1,2,4-triazolyl, tetrazolyl, furanyl, thienyl, pyridyl, pyrimidyl, pyridazinyl, or any of such groups fused to a phenyl ring, such as quinolinyl, benzimidazolyl, benzoxazolyl, benzisoxazolyl, benzothiazinolyl, benzisothiazinolyl, benzothiazolyl, benzoxadiazolyl, benzo-1,2,3-triazolyl, benzo-1,2,4-triazolyl, benzotetrazolyl, benzofuranyl, benzothienyl, benzopyridyl, benzopyrimidyl, benzopyridazinyl, benzopyrazolyl etc, which ring is bonded directly i.e. ($C_0$), or through an intermediate methyl, ethyl, propyl, or isopropyl group as defined for $C_1$-$C_3$alkylene above. Any such non-saturated rings having an aromatic character may be referred to as heteroaryl herein. Unless otherwise indicated the hetero ring and/or its fused phenyl moiety is optionally substituted with 1-3 substituents selected from halo, hydroxy, nitro, cyano, carboxy, $C_1$-$C_6$alkyl, $C_1$-$C_6$alkoxy, $C_1$-$C_6$alkoxy$C_1$-$C_6$alkyl, $C_1$-$C_6$alkanoyl, amino, azido, oxo, mercapto, nitro, $C_0$-$C_3$alkylcarbocyclyl, $C_0$-$C_3$alkylheterocyclyl. "Heterocyclyl" and "Heteroaryl" have the corresponding meaning, i.e. where the $C_0$-$C_3$alkyl linkage is absent.

Typically heterocycyl and carbocyclyl moieties within the scope of the above definitions are thus a monocyclic ring with 5 or especially 6 ring atoms, or a bicyclic ring structure comprising a 6 membered ring fused to a 4, 5 or 6 membered ring.

Typical such groups include $C_3$-$C_8$cycloalkyl, phenyl, benzyl, tetrahydronaphthyl, indenyl, indanyl, heterocyclyl such as from azepanyl, azocanyl, pyrrolidinyl, piperidinyl, morpholinyl, thiomorpholinyl, piperazinyl, indolinyl, pyranyl, tetrahydropyranyl, tetrahydrothiopyranyl, thiopyranyl, furanyl, tetrahydrofuranyl, thienyl, pyrrolyl, oxazolyl, isoxazolyl, thiazolyl, imidazolyl, pyridinyl, pyrimidinyl, pyrazinyl, pyridazinyl, tetrazolyl, pyrazolyl, indolyl, benzofuranyl, benzothienyl, benzimidazolyl, benzthiazolyl, benzoxazolyl, benzisoxazolyl, quinolinyl, tetrahydroquinolinyl, isoquinolinyl, tetrahydroisoquinolinyl, quinazolinyl, tetrahydroquinazolinyl and quinoxalinyl, any of which may be optionally substituted as defined herein.

The saturated heterocycle moiety thus includes radicals such as pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 1,4,5,6-tetrahydropyrimidinylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione, whereas the unsaturated heterocycle include radicals with an aromatic character such as furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, indolizinyl, indolyl, isoindolyl. In each case the heterocycle may be condensed with a phenyl ring to form a bicyclic ring system.

The radical Het is a heterocycle as specified in this specification and claims. Examples of Het comprise, for example, pyrrolidinyl, piperidinyl, morpholinyl, thiomorpholinyl, piperazinyl, pyrrolyl, pyrazolyl, imidazolyl, oxazolyl, isoxazolyl, thiazinolyl, isothiazinolyl, thiazolyl, isothiazolyl, oxadiazolyl, thiadiazolyl, triazolyl (including 1,2,3-triazolyl, 1,2,4-triazolyl), tetrazolyl, furanyl, thienyl, pyridyl, pyrimidyl, pyridazinyl, triazinyl, or any of such heterocycles condensed with a benzene ring, such as indolyl, indazolyl (in particular 1H-indazolyl), indolinyl, quinolinyl, tetrahydroquinolinyl (in particular 1,2,3,4-tetrahydroquinolinyl), isoquinolinyl, tetrahydroisoquinolinyl (in particular 1,2,3,4-tetrahydroisoquinolinyl), quinazolinyl, quinoxalinyl, cinnolinyl, phthalazinyl, benzimidazolyl, benzoxazolyl, benzisoxazolyl, benzothiazinolyl, benzisothiazinolyl, benzothiazolyl, benzoxadiazolyl, benzothiadiazolyl, benzo-1,2,3-triazolyl, benzo-1,2,4-triazolyl, benzotetrazolyl, benzofuranyl, benzothienyl, benzopyrazolyl, and the like. Of interest amongst the Het radicals are those which are non-saturated, in particular those having an aromatic character. Of further interest are those Het radicals which are monocyclic.

Each of the Het or $R^8$ radicals mentioned in this and the following paragraph may be optionally substituted with the number and kind of substituents mentioned in the definitions of the compounds of formula (I) or any of the subgroups of compounds of formula (I). Some of the Het or $R^8$ radicals mentioned in this and the following paragraph may be substituted with one, two or three hydroxy substituents. Such hydroxy substituted rings may occur as their tautomeric forms bearing keto groups. For example a 3-hydroxypyridazine moiety can occur in its tautomeric form 2H-pyridazin-3-one. Some examples keto-substituted Het or $R^1$ radicals are 1,3-dihydro-benzimidazol-2-one, 1,3-dihydroindol-2-one, 1H-indole-2,3-dione, 1H-benzo[d]isoxazole, 1H-benzo[d]isothiazole, 1H-quinolin-2-one, 1H-quinolin-4-one, 1H-quinazolin-4-one, 9H-carbazole, and 1H-quinazolin-2-one.

$R^8$ can be a saturated, a partially unsaturated or completely unsaturated 5 or 6 membered monocyclic or 9 to 12 membered bicyclic heterocyclic ring system as specified in this specification and claims. Examples of said monocyclic or bicyclic ring system comprise for example, any of the rings mentioned in the previous paragraph as examples of the radical Het and additionally any of the monocyclic heterocycles mentioned in the previous paragraph condensed with pyridyl or pyrimidinyl such as, for example, pyrrolopyridine (in particular 1H-pyrrolo[2,3]-b]pyridine, 1H-pyrrolo[2,3-c]pyridine), naphtyridine (in particular 1,8-naphtyridine), imidazopyridine (in particular 1H-imidazo[4,5-c]pyridine, 1H-imidazo[4,5-b]pyridine), pyridopyrimidine, purine (in particular 7H-purine) and the like.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar terms, it is meant to include the compounds of formula (I), their prodrugs, N-oxides, addition salts, quaternary amines, metal complexes, and stereochemically isomeric forms. One embodiment comprises the compounds of formula (I) or any subgroup of compounds of formula (I) specified herein, as well as the N-oxides, salts, as the possible stereoisomeric forms thereof. Another embodiment comprises the compounds of formula (I) or any subgroup of compounds of formula (I) specified herein, as well as the salts as the possible stereoisomeric forms thereof.

The compounds of formula (I) have several centers of chirality and exist as stereochemically isomeric forms. The term "stereochemically isomeric forms" as used herein defines all the possible compounds made up of the same atoms bonded by the same sequence of bonds but having different three-dimensional structures which are not interchangeable, which the compounds of formula (I) may possess.

With reference to the instances where (R) or (S) is used to designate the absolute configuration of a chiral atom within a substituent, the designation is done taking into consideration the whole compound and not the substituent in isolation.

Unless otherwise mentioned or indicated, the chemical designation of a compound encompasses the mixture of all possible stereochemically isomeric forms, which said compound may possess. Said mixture may contain all diastereomers and/or enantiomers of the basic molecular structure of said compound. All stereochemically isomeric forms of the compounds of the present invention both in pure form or mixed with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term "stereoisomerically pure" concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms "enantiomerically pure" and "diastereomerically pure" should be understood in a similar way, but then having regard to the enantiomeric excess, and the diastereomeric excess, respectively, of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of the compounds of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes, and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

The term "prodrug" as used throughout this text means the pharmacologically acceptable derivatives such as esters, amides and phosphates, such that the resulting in vivo biotransformation product of the derivative is the active drug as defined in the compounds of formula (I). The reference by Goodman and Gilman (The Pharmacological Basis of Therapeutics, 8$^{th}$ ed, McGraw-Hill, Int. Ed. 1992, "Biotransformation of Drugs", p 13-15) describing prodrugs generally is hereby incorporated. Prodrugs preferably have excellent aqueous solubility, increased bioavailability and are readily metabolized into the active inhibitors in vivo. Prodrugs of a compound of the present invention may be prepared by modifying functional groups present in the compound in such a way that the modifications are cleaved, either by routine manipulation or in vivo, to the parent compound.

Preferred are pharmaceutically acceptable ester prodrugs that are hydrolysable in vivo and are derived from those compounds of formula (I) having a hydroxy or a carboxyl group. An in vivo hydrolysable ester is an ester, which is hydrolysed in the human or animal body to produce the parent acid or alcohol. Suitable pharmaceutically acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl which may be formed at any carboxy group in the compounds of this invention.

An in vivo hydrolysable ester of a compound of the formula (I) containing a hydroxy group includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxy-methoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. Examples of substituents on benzoyl include morpholino and piperazino linked from a ring nitrogen atom via a methylene group to the 3- or 4-position of the benzoyl ring.

For therapeutic use, salts of the compounds of formula (I) are those wherein the counter-ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

As mentioned above, the compounds of formula (I) have several asymmetric centers. In order to more efficiently refer to each of these asymmetric centers, the numbering system as indicated in the following structural formula will be used.

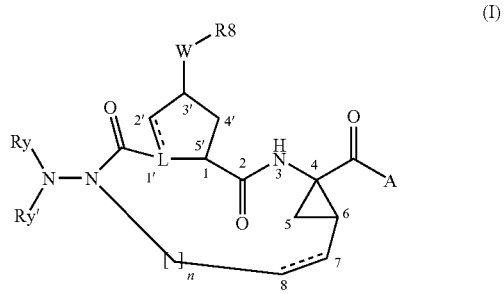

Asymmetric centers are present at positions 1, 4 and 6 of the macrocycle as well as at the carbon atom 3' in the 5-membered ring, carbon atom 2' when the Rq substituent is $C_{1-6}$alkyl, and at carbon atom 1' when L is CH. Each of these asymmetric centers can occur in their R or S configuration.

The stereochemistry at position 1 preferably corresponds to that of an L-amino acid configuration, i.e. that of L-proline.

When L is CH, the 2 carbonyls borne by the cyclopentane ring are preferably trans as depicted below.

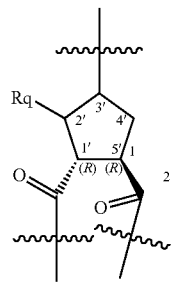

The stereochemistry at position 1 preferably corresponds to that of an L-amino acid configuration, i.e. that of L-proline.

The structure of formula (I) includes a cyclopropyl group as represented in the P1 fragment below:

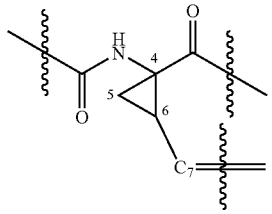

wherein $C_7$ represents the carbon at position 7 and carbons at position 4 and 6 are asymmetric carbon atoms of the cyclopropane ring.

Notwithstanding other possible asymmetric centers at other segments of the compounds of the invention, the presence of these two asymmetric centers means that the compounds can exist as mixtures of diastereomers, such as the diastereomers of compounds of formula (I) wherein the carbon at position 7 is configured either syn to the carbonyl or syn to the amide as shown below.

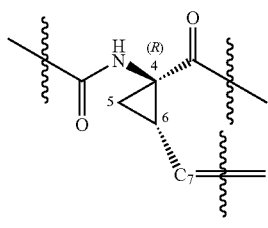

C7 syn to carbonyl

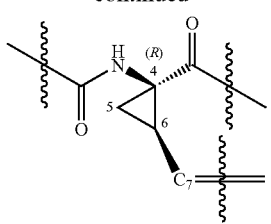

C7 syn to amide

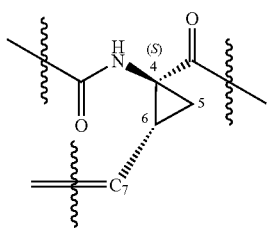

C7 syn to carbonyl

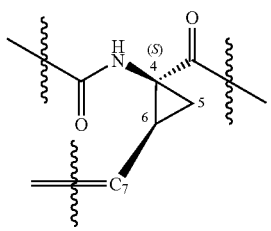

C7 syn to amide

The structure of formula (I) may include as well a proline residue (when L is N). Preferred are the compounds of formula (I) wherein the substituent at the 1 (or 5') position and the substituent —W—$R^8$ (at position 3') are in a trans configuration. Of particular interest are the compounds of formula (I) wherein position 1 has the configuration corresponding to L-proline and the —W—$R^8$ substituent is in a trans configuration in respect of position 1. Preferably the compounds of formula (I) have the stereochemistry as indicated in the structures of formulae (I-a) and (I-b) below:

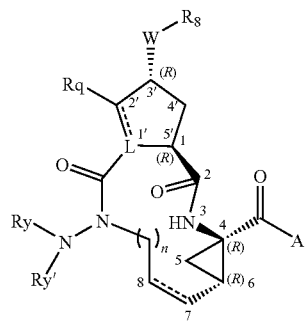

(I-a)

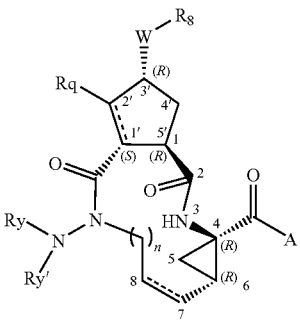

(I-b)

One embodiment of the present invention concerns compounds of formula (I) or of formula (I-a) or of any subgroup of compounds of formula (I), wherein one or more of the following conditions apply:

(a) Rq is hydrogen;

(b) L is nitrogen;

(c) a double bond is present between carbon atoms 7 and 8.

(d) n is 3 or 4

One embodiment of the present invention concerns compounds of formula (I) or of formulae (I-a), (I-b), or of any subgroup of compounds of formula (I), wherein one or more of the following conditions apply:

(a) Rq is hydrogen;

(b) X is CH;

(c) a double bond is present between carbon atoms 7 and 8.

(d) n is 3 or 4

One embodiment of the present invention concerns compounds of formula (I) or of formulae (I-a), (I-b), or of any subgroup of compounds of formula (I), wherein one or more of the following conditions apply:

(a) Rq is methyl;

(b) X is C and bears a double bond to the asterisked carbon;

(c) a double bond is present between carbon atoms 7 and 8.

(d) n is 3 or 4.

One embodiment of the present invention include compounds of formula (I) wherein A is $NHS(=O)_2R^2$, in particular wherein $R^2$ is $C_1$-$C_6$alkyl optionally substituted with $C_3$-$C_7$cycloalkyl, $C_3$-$C_7$cycloalkyl optionally substituted with $C_1$-$C_6$alkyl, for example $R^2$ can be 1-methylcyclopropyl.

One embodiment of the present invention thus provides compounds comprising the partial structure:

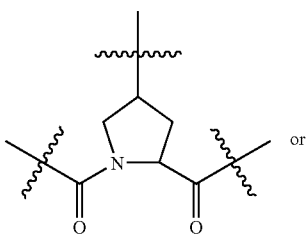

or

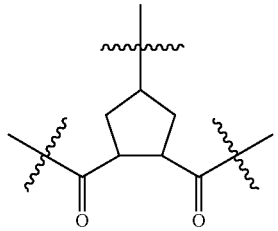

It is to be understood that the above defined subgroups of compounds of formulae (I-a) and (I-b) as well as any other subgroup defined herein, are meant to also comprise any prodrugs, N-oxides, addition salts, quaternary amines, metal complexes and stereochemically isomeric forms of such compounds.

When n is 2, the moiety $—CH_2—$ bracketed by "n" corresponds to a ethanediyl in the compounds of formula (I) or in any subgroup of compounds of formula (I). When n is 3, the moiety $—CH_2—$ bracketed by "n" corresponds to a propanediyl in the compounds of formula (I) or in any subgroup of compounds of formula (I). When n is 4, the moiety $—CH_2—$ bracketed by "n" corresponds to a butanediyl in the compounds of formula (I) or in any subgroup of compounds of formula (I). When n is 5, the moiety $—CH_2—$ bracketed by "n" corresponds to a pentanediyl in the compounds of formula (I) or in any subgroup of compounds of formula (I). When n is 6, the moiety $—CH_2—$ bracketed by "n" corresponds to a hexanediyl in the compounds of formula (I) or in any subgroup of compounds of formula (I). Particular subgroups of the compounds of formula (I) are those compounds wherein n is 4 or 5.

Further subgroups of the compounds of formula (I) are those compounds of formula (I), or any subgroup of compounds of formula (I) specified herein, wherein $R^8$ is phenyl, naphthyl, pyridyl, pyridazinyl, triazolyl, tetrazolyl, quinolinyl, isoquinolinyl, quinazolinyl, pyrimidinyl, [1,8]naphthyridinyl, indolinyl, 1,2,3,4-tetrahydroquinoline, 1,2,3,4-tetrahydroisoquinoline; all optionally substituted with one, two or three substituents selected from $R^9$ in the definitions of the compounds of formula (I), especially any of which $R^8$ groups is, independently, optionally mono, di, or tri substituted with methyl, ethyl, isopropyl, tert-butyl, methoxy, trifluoromethyl, trifluoromethoxy, fluoro, chloro, bromo, $—NRt^{5a}R^{5b}$, $—C(=O)NRt^{5a}Rt^{5b}$, phenyl, methoxyphenyl, cyanophenyl, halophenyl, pyridyl, $C_{1-4}$alkylpyridyl, pyrimidinyl, morpholinyl, piperazinyl, $C_{1-4}$alkylpiperazinyl, pyrrolidinyl, pyrazolyl, $C_{1-4}$alkyl-pyrazolyl, thiazolyl, $C_{1-4}$alkylthiazolyl, cyclopropylthiazolyl, or mono- or di$C_{1-4}$alkyl-aminothiazolyl, where $Rt^{5a}$ and $Rt^{5b}$ are, independently, hydrogen, $C_{3-7}$cycloalkyl, aryl, heterocyclyl, $C_{1-6}$alkyl optionally substituted with halo, $C_{1-6}$alkoxy, cyano, halo$C_{1-6}$alkoxy, $C_{3-7}$cycloalkyl, aryl or with heterocyclyl.

Other subgroups of the compounds of formula (I) are those compounds of formula (I), or any subgroup of compounds of formula (I) specified herein, wherein (a) $R^8$ is phenyl, naphthyl (in particular naphth-1-yl, or naphth-2-yl), quinolinyl (in particular quinolin-4-yl), isoquinolinyl (in particular isoquinolin-1-yl), quinazolinyl (in particular quinazolin-4-yl), pyridyl (in particular 3-pyridyl), pyrimidinyl (in particular pyrimidin-4-yl), pyridazinyl (in particular pyridazin-3-yl and pyridazin-2-yl), [1,8]naphthyridinyl (in particular [1,8]naphthyridin-4-yl);

(a) (b) R$^8$ is triazolyl (in particular triazol-1-yl, triazol-2-yl), tetrazolyl (in particular tetrazol-1-yl, tetrazol-2-yl), 6-oxo-pyridazin-1-yl, pyrazolyl (in particular pyrazol-1-yl), or imidazolyl (in particular imidazol-1-yl, imidazol-2-yl);

(c) R$^8$ is a heterocycle selected from

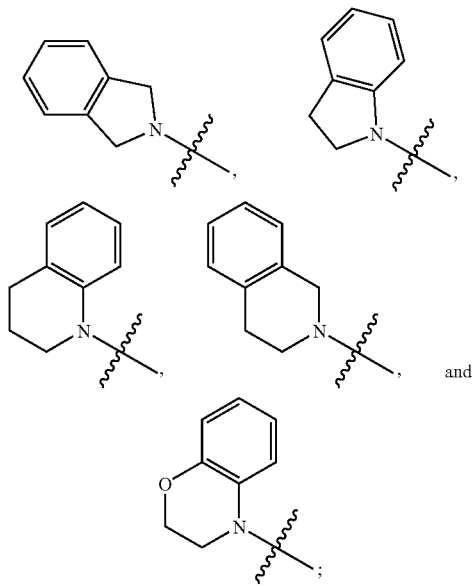

and wherein each of the R$^8$ radicals may be optionally substituted with one, two or three substituents selected from R$^9$ in the definitions of the compounds of formula (I), especially any of which R$^8$ groups is, independently, optionally mono, di, or tri substituted with methyl, ethyl, isopropyl, tert-butyl, methoxy, trifluoromethyl, trifluoromethoxy, fluoro, chloro, bromo, —NRt$^{5a}$Rt$^{5b}$, —C(=O)NRt$^{5a}$Rt$^{5b}$, phenyl, methoxyphenyl, cyanophenyl, halophenyl, pyridyl, C$_{1-4}$alkylpyridyl, pyrimidinyl, morpholinyl, piperazinyl, C$_{1-4}$alkylpiperazinyl, pyrrolidinyl, pyrazolyl, C$_{1-4}$alkyl-pyrazolyl, thiazolyl, C$_{1-4}$alkylthiazolyl, cyclopropylthiazolyl, or mono- or diC$_{1-4}$alkyl-aminothiazolyl, where Rt$^{5a}$ and Rt$^{5b}$ are, independently, hydrogen, C$_{3-7}$cycloalkyl, aryl, heterocyclyl, C$_{1-6}$alkyl optionally substituted with halo, C$_{1-6}$alkoxy, cyano, haloC$_{1-6}$alkoxy, C$_{3-7}$cycloalkyl, aryl or with heterocyclyl.

Embodiments of the invention are compounds of formula (I) or any of the subgroups of compounds of formula (I) wherein W is a direct bond, —O—, —OC(=O)—, or —OC(=O)NH—, or in particular wherein W is —O—.

Preferably W is —O—, and R$^8$ is as specified above in (a). Preferably W is a direct bond, and R$^8$ is as specified above in (b). Preferably Lt is a —OC(=O)—, and R$^8$ is as specified above in (c), or Lt is —OC(=O)NH— and R$^8$ is phenyl which is optionally substituted with 1-3 R$^9$ groups.

Embodiments of the invention are compounds of formula (I) or any of the subgroups of compounds of formula (I) wherein W is —O— and R$^8$ is quinolin-4-yl, isoquinolin-1-yl, quinazolin-4-yl, or pyrimidin-4-yl, either of which is, independently, optionally mono, di, or tri substituted with C$_{1-6}$alkyl, C$_{1-6}$alkoxy, nitro, hydroxy, halo, trifluoromethyl, —NRt$^{5a}$Rt$^{5b}$, —C(=O)NRt$^{5a}$Rt$^{5b}$, C$_{3-7}$cycloalkyl, aryl, Het, —C(=O)OH, or —C(=O)ORt$^{6a}$; wherein aryl or Het are each, independently, optionally substituted with halo, C$_{1-6}$alkyl, C$_{1-6}$alkoxy, amino, mono- or diC$_{1-6}$alkylamino, pyrrolidinyl, piperidinyl, piperazinyl, N-methylpiperazinyl or morpholinyl.

Embodiments of the invention are compounds of formula (I) or any of the subgroups of compounds of formula (I) wherein W is —O— and R$^8$ is quinolin-4-yl, isoquinolin-1-yl, quinazolin-4-yl, or pyrimidin-4-yl, either of which is, independently, optionally mono, di, or tri substituted with methyl, ethyl, isopropyl, tert-butyl, methoxy, trifluoromethyl, trifluoromethoxy, fluoro, chloro, bromo, —NRt$^{5a}$Rt$^{5b}$, —C(=O)NRt$^{5a}$Rt$^{5b}$, phenyl, methoxyphenyl, cyanophenyl, halophenyl, pyridyl, C$_{1-4}$alkylpyridyl, pyrimidinyl, morpholinyl, piperazinyl, C$_{1-4}$alkylpiperazinyl, pyrrolidinyl, pyrazolyl, C$_{1-4}$alkyl-pyrazolyl, thiazolyl, C$_{1-4}$alkylthiazolyl, cyclopropylthiazolyl, or mono- or diC$_{1-4}$alkyl-aminothiazolyl.

Embodiments of the invention are compounds of formula (I) or any of the subgroups of compounds of formula (I) wherein W is —O— and R$^8$ is quinolinyl (in particular quinolin-4-yl), isoquinolinyl (in particular isoquinolin-1-yl), quinazolinyl (in particular quinazolin-4-yl), or pyrimidinyl (in particular pyrimidin-4-yl), either of which is, independently, optionally mono, di, or tri substituted with C$_{1-6}$alkyl, C$_{1-6}$alkoxy, nitro, hydroxy, halo, trifluoromethyl, —NRt$^{5a}$Rt$^{5b}$, —C(=O)NRt$^{5a}$Rt$^{5b}$, C$_{3-7}$cycloalkyl, aryl, Het, —C(=O)OH, or —C(=O)OR$^{6a}$; wherein aryl or Het are each, independently, optionally substituted with halo, C$_{1-6}$alkyl, C$_{1-6}$alkoxy, amino, mono- or diC$_{1-6}$alkylamino, pyrrolidinyl, piperidinyl, piperazinyl, 4-C$_{1-6}$alkylpiperazinyl (e.g. 4-methylpiperazinyl), thiomorpholinyl or morpholinyl; and wherein the morpholinyl, thiomorpholinyl and piperidinyl groups may optionally substituted with one or two C$_{1-6}$alkyl radicals.

Embodiments of the invention are compounds of formula (I) or any of the subgroups of compounds of formula (I) wherein W is —O— and R$^8$ is quinolinyl (in particular quinolin-4-yl), isoquinolinyl (in particular isoquinolin-1-yl), quinazolinyl (in particular quinazolin-4-yl), or pyrimidinyl (in particular pyrimidin-4-yl), either of which is, independently, optionally mono, di, or tri substituted with methyl, ethyl, isopropyl, tert-butyl, methoxy, trifluoromethyl, trifluoromethoxy, fluoro, chloro, bromo, —NRt$^{5a}$Rt$^{5b}$, —C(=O)NRt$^{5a}$Rt$^{5b}$, phenyl, methoxyphenyl, cyanophenyl, halophenyl, pyridyl, C$_{1-4}$alkylpyridyl, pyrimidinyl, piperidinyl, morpholinyl, thiomorpholinyl, piperazinyl, C$_{1-4}$alkylpiperazinyl, pyrrolidinyl, pyrazolyl, C$_{1-4}$alkyl-pyrazolyl, thiazolyl, C$_{1-4}$alkylthiazolyl, cyclopropylthiazolyl, or mono- or diC$_{1-4}$alkyl-aminothiazolyl; and wherein the morpholinyl, thiomorpholinyl and piperidinyl groups may optionally substituted with one or two C$_{1-6}$alkyl (in particular one or two methyl) radicals.

Embodiments of the invention are compounds of formula (I) or any of the subgroups of compounds of formula (I) wherein R$^8$ is quinolinyl, optionally substituted with 1, 2, 3 or 4 (or with 1, 2 or 3) substituents selected from those mentioned as possible substituents on the monocyclic or bicyclic ring systems of R$^8$, as specified in the definitions of the compounds of formula (I) or of any of the subgroups of compounds of formula (I).

Specific embodiments of the invention are those compounds of formula (I) or any of the subgroups of compounds of formula (I) wherein R$^8$ is (d-1) a radical of formula

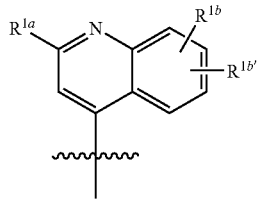

(d-2) a radical of formula

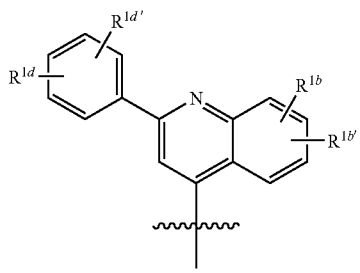

(d-3) a radical of formula

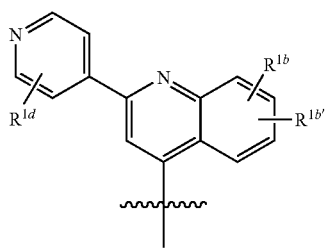

(d-4) a radical of formula

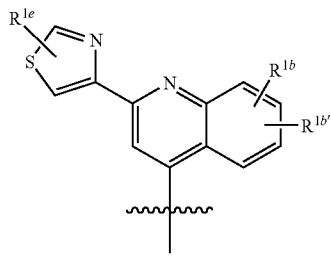

or in particular, (d-4-a) a radical of formula

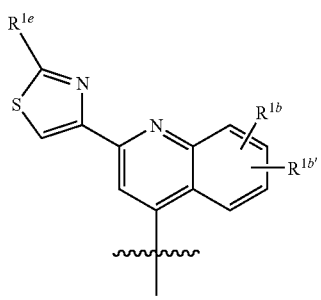

(d-5) a radical of formula

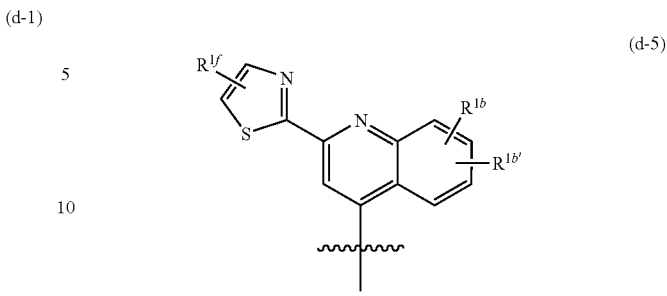

or in particular, (d-5-a) a radical of formula

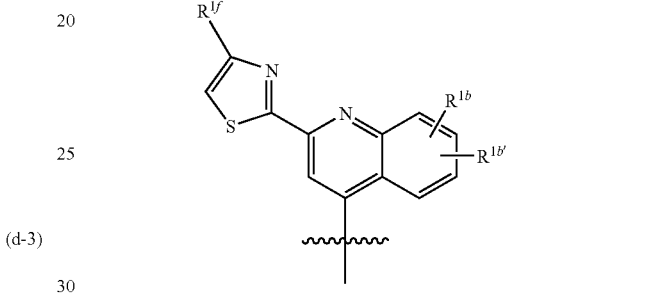

wherein in radicals (d-1)-(d-5), as well as in (d-4-a) and (d-5-a):

each $R^{1a}$, $R^{1b}$, $R^{1b'}$, $R^{1d}$, $R^{1d'}$, $R^{1e}$, $R^{1f}$ are independently any of the substituents selected from those mentioned as possible substituents on the monocyclic or bicyclic ring systems of $R^1$, as specified in the definitions of the compounds of formula (I) or of any of the subgroups of compounds of formula (I);

or, in particular, wherein in radicals (d-1)-(d-5), as well as in (d-4-a) and (d-5-a):

$R^{1b}$ and $R^{1b'}$ may, independently, be hydrogen, $C_{1-6}$alkyl, $C_{1-6}$alkoxy, —$NRt^{5a}Rt^{5b}$ (in particular amino or mono- or di$C_{1-6}$alkylamino), —C(=O)$NR^{5a}R^{5b}$, (in particular aminocarbonyl or mono- or di$C_{1-6}$alkylaminocarbonyl), nitro, hydroxy, halo, trifluoromethyl, —C(=O)OH, or —C(=O)$OR^{6a}$ (in particular $C_{1-6}$alkyl);

wherein each $Rt^{5a}$, $Rt^{5b}$, $Rt^{6a}$ mentioned above or hereinafter independently is as defined in the definitions of the compounds of formula (I) or of any of the subgroups of compounds of formula (I);

or, in particular, wherein in radicals (d-1)-(d-5), as well as in (d-4-a) and (d-5-a):

$R^{1a}$ is hydrogen, $C_{1-6}$alkyl, $C_{1-6}$alkoxy, $C_{1-6}$alkylthio, mono$C_{1-6}$alkylamino, amino, $C_{3-7}$cycloalkyl, aryl, or Het;

more specifically $R^{1a}$ is aryl or Het; of interest are embodiments wherein $R^{1a}$ is phenyl, pyridyl, thiazolyl, pyrazolyl, each substituted as specified in the definitions of the compounds of formula (I) or of any of the subgroups of the compounds of formula (I); in specific embodiments said aryl or Het may each, independently, optionally substituted with $C_{1-6}$alkyl, $C_{1-6}$alkoxy, amino, mono- or di$C_{1-6}$alkylamino; and in particular $R^{1a}$ can be a radical Het; wherein Het may include pyrrolidinyl, piperidinyl, morpholinyl, thiomorpholinyl, piperazinyl, 4-$C_{1-6}$alkylpiperazinyl; and wherein the morpholinyl, thiomorpholinyl and piperidinyl groups may optionally substituted with one or two $C_{1-6}$alkyl radicals;

Embodiments of the invention are compounds of formula (I) or any of the subgroups of compounds of formula (I) wherein $R^{1a}$ is a radical:

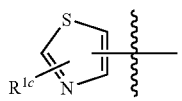
(q)

or, in particular, wherein $R^{1a}$ is selected from the group consisting of:

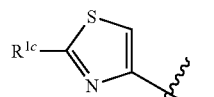
(q-1)

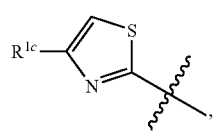
(q-2)

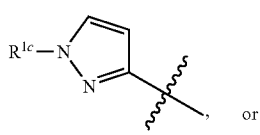
(q-3)

, or

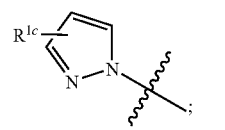
(q-4)
;

wherein each $R^{1c}$ is any of the $R^1$ substituents may be selected from those mentioned as possible substituents on the monocyclic or bicyclic ring systems of $R^1$, as specified in the definitions of the compounds of formula (I) or of any of the subgroups of compounds of formula (I);

specifically each $R^{1c}$ may be hydrogen, halo, $C_{1-6}$alkyl, $C_{1-6}$alkoxy, polyhalo$C_{1-6}$alkyl (in particular trifluoromethyl), —NRt$^{5a}$Rt$^{5b}$ (in particular amino or mono- or di$C_{1-6}$alkylamino), —C(=O)NR$^{5a}$R$^{5b}$, (in particular aminocarbonyl or mono- or di$C_{1-6}$alkylamino-carbonyl), nitro, hydroxy, —C(=O)OH, or —C(=O)OR$^{6a}$ (in particular $C_{1-6}$alkyl), pyrrolidinyl, piperidinyl, morpholinyl, thiomorpholinyl, piperazinyl, 4-$C_{1-6}$alkyl-piperazinyl (in particular 4-methylpiperazinyl); and wherein the morpholinyl and piperidinyl groups may optionally substituted with one or two $C_{1-6}$alkyl radicals;

more specifically each $R^{1c}$ may be hydrogen, halo, $C_{1-6}$alkyl, amino, or mono- or di-$C_{1-6}$alkylamino, pyrrolidinyl, piperidinyl, morpholinyl, thiomorpholinyl, piperazinyl, 4-$C_{1-6}$alkylpiperazinyl; and wherein the morpholinyl and piperidinyl groups may optionally substituted with one or two $C_{1-6}$alkyl radicals;

specifically each $R^{1d}$ and $R^{1d'}$ independently may be hydrogen, $C_{1-6}$alkyl, $C_{1-6}$alkoxy, or halo;

or more specifically each $R^{1d}$ in (d-3) may be hydrogen, $C_{1-6}$alkyl, $C_{1-6}$alkoxy or halo;

specifically $R^{1e}$ may be hydrogen, $C_{1-6}$alkyl, amino, mono- or di$C_{1-6}$alkylamino, pyrrolidinyl, piperidinyl, morpholinyl, thiomorpholinyl, piperazinyl, 4-$C_{1-6}$alkyl-piperazinyl (in particular 4-methylpiperazinyl); and wherein the morpholinyl and piperidinyl groups may optionally substituted with one or two $C_{1-6}$alkyl radicals;

preferably each $R^{1b}$ is $C_{1-6}$alkoxy, more preferably methoxy;

specifically $R^{1f}$ may be hydrogen, $C_{1-6}$alkyl, amino, mono- or di$C_{1-6}$alkylamino, pyrrolidinyl, piperidinyl, piperazinyl, N-methylpiperazinyl, or morpholinyl.

Specific embodiments of the invention are compounds of formula (I) or any of the subgroups of compounds of formula (I) wherein $R^8$ is 7-methoxy-2-phenyl-quinolin-4-yl and W is —O—.

Embodiments of the invention are compounds of formula (I) or any of the subgroups of compounds of formula (I) wherein $R^8$ is (e) isoquinolinyl (in particular 1-isoquinolinyl), optionally substituted with 1, 2, 3 or 4 (or with 1, 2 or 3) substituents selected from those mentioned as possible substituents on the monocyclic or bicyclic ring systems of $R^8$, as specified in the definitions of the compounds of formula (I) or of any of the subgroups of compounds of formula (I).

Specific such embodiments are those wherein $R^8$ is (e-1) a radical of formula:

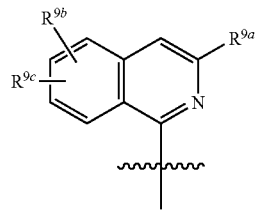
(e-1)

or in particular (e-1-a) a radical of formula:

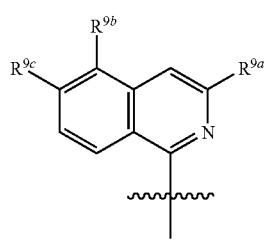
(e-1-a)

wherein $R^{9a}$, $R^{9b}$, $R^{9c}$ independently form one another are any of the substituents selected from those mentioned as possible substituents on the monocyclic or bicyclic ring systems of $R^8$, as specified in the definitions of the compounds of formula (I) or of any of the subgroups of compounds of formula (I); in particular $R^{9a}$ may have the same meanings as $R^{1a}$ as specified above; in particular it may be aryl or Het, either of which is optionally substituted with any of the radicals mentioned as substituents of aryl or of Het as specified definitions of the compounds of formula (I) or of any of the subgroups of compounds of formula (I) (including the number of substituents); specifically said aryl or Het may be substituted with 1, 2 or 3 (in particular with one) radical or radicals $R^{10}$; wherein said $R^{10}$ is any of the radicals mentioned as substituents of Het as specified definitions of the compounds of formula (I) or of any of the subgroups of compounds of formula (I) as defined above; or in particular $R^{10}$ is hydrogen, $C_{1-6}$alkyl, aryl, $C_{3-7}$cycloalkyl, Het, amino optionally mono or disubstituted with $C_{1-6}$alkyl, or aminocarbonyl or mono- or di$C_{1-6}$alkylaminocarbonyl; wherein Het also includes pyrrolidinyl, piperidinyl, piperazinyl, 4-$C_{1-6}$alkylpiperazinyl (e.g. 4-methylpiperazinyl), thiomorpholinyl or morpholinyl; and wherein the morpholinyl, thiomorpholinyl or piperidinyl groups may optionally substituted with one or two $C_{1-6}$alkyl radicals;

$R^{9b}$ may have the same meanings as $R^{1b}$ as specified above; in particular it may be is hydrogen, $C_{1-6}$alkyl, cycloalkyl, aryl, Het, halo (e.g. bromo, chloro or fluoro);

$R^{9c}$ may have the same meanings as $R^{1c}$ as specified above; in particular it may be is hydrogen or $C_{1-6}$alkoxy.

In particular $R^{9a}$ in the isoquinolinyl radical specified under (e-1) or (1-e-a) includes phenyl, pyridyl, thiazolyl, oxazolyl or pyrazolyl either of which is optionally substituted with $R^{10}$ as defined above, in particular optionally substituted with an $R^{10}$ which may be hydrogen, $C_{1-6}$alkyl (e.g. methyl, ethyl, isopropyl, tert-butyl), $C_{1-6}$alkoxy, amino, pyrrolidinyl, piperidinyl, piperazinyl, 4-$C_{1-6}$alkylpiperazinyl (e.g. 4-methylpiperazinyl), thiomorpholinyl or morpholinyl, $C_{1-6}$alkylamino, ($C_{1-6}$alkyl)$_2$amino, aminocarbonyl, or mono- or di$C_{1-6}$alkylaminocarbonyl; and wherein the morpholinyl, thiomorpholinyl and piperidinyl groups may optionally substituted with one or two $C_{1-6}$alkyl radicals.

Preferably $R^{9a}$ in the isoquinolinyl radical specified under (e-1) or (e-1-a) includes any of radicals (q), (q-1), (q-2), (q-3), (q-4) specified above as well as:

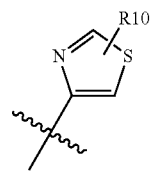
(q-5)

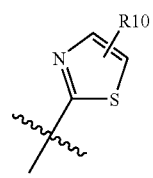
(q-6)

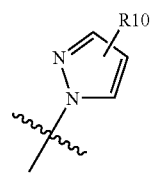
(q-7)

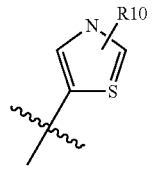
(q-8)

wherein each $R^{10}$ is any of the radicals mentioned as substituents of Het as specified definitions of the compounds of formula (I) or of any of the subgroups of compounds of formula (I) as defined above; or in particular $R^{10}$ is as defined above; especially $R^{10}$ is hydrogen, $C_{1-6}$alkyl (e.g. methyl, ethyl, isopropyl, tert-butyl), amino, pyrrolidinyl, piperidinyl, piperazinyl, 4-$C_{1-6}$alkylpiperazinyl (e.g. 4-methylpiperazinyl), thiomorpholinyl or morpholinyl; $C_{1-6}$alkylamino, ($C_{1-6}$alkyl)$_2$amino, aminocarbonyl, or mono- or di$C_{1-6}$alkylaminocarbonyl; and wherein the morpholine, thiomorpholine and piperidine may optionally substituted with one or two $C_{1-6}$alkyl radicals.

Also preferably $R^{9a}$ in the isoquinolinyl radical specified under (e-1) or (e-1-a) includes:

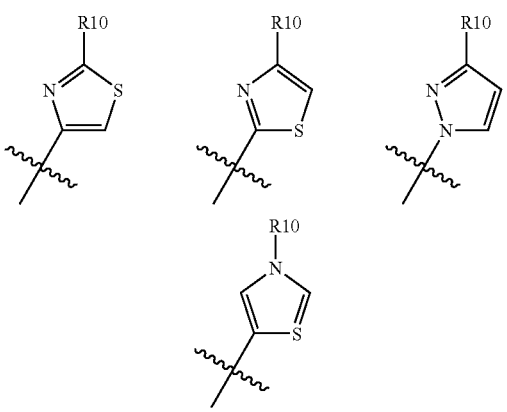

wherein each $R^{10}$ is as defined above, and especially is hydrogen, halo, $C_{1-6}$alkyl (e.g. methyl, ethyl, isopropyl, tert-butyl), amino, pyrrolidinyl, piperidinyl, piperazinyl, 4-$C_{1-6}$alkylpiperazinyl (e.g. 4-methylpiperazinyl), thiomorpholinyl or morpholinyl; $C_{1-6}$alkylamino, ($C_{1-6}$alkyl)$_2$amino, aminocarbonyl, or mono- or di$C_{1-6}$alkylamino-carbonyl;

and wherein the morpholinyl, thiomorpholinyl and piperidinyl groups may optionally substituted with one or two $C_{1-6}$alkyl radicals.

$R^{9b}$ in the isoquinolinyl radical specified under (e-2) may be hydrogen, $C_{1-6}$alkyl, halo (e.g. bromo, chloro or fluoro), especially hydrogen or bromo.

$R^{9b}$ in the isoquinolinyl radical specified under (e-2) may be hydrogen or $C_{1-6}$alkoxy (e.g. methoxy).

Embodiments of the invention are compounds of formula (I) or any of the subgroups of compounds of formula (I) wherein $R^8$ is

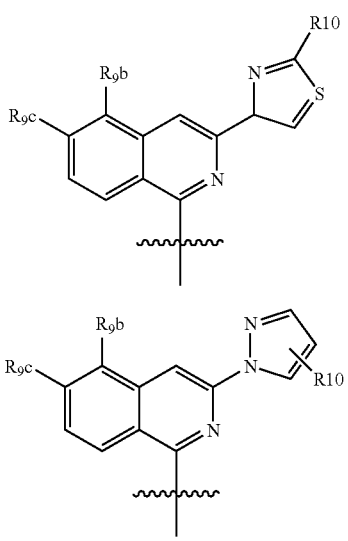

(e-2)

(e-3)

wherein $R^{9b}$ is hydrogen or halo (e.g. bromo) and $R^{9c}$ is hydrogen or $C_{1-6}$alkoxy (e.g. methoxy).

Embodiments of the invention are compounds of formula (I) or any of the subgroups of compounds of formula (I) wherein $R^8$ is (f) quinazolinyl (in particular quinazolin-4-yl), optionally substituted with 1, 2, 3 or 4 (or with 1, 2 or 3) substituents selected from those mentioned as possible substituents on the monocyclic or bicyclic ring systems of $R^8$, as specified in the definitions of the compounds of formula (I) or of any of the subgroups of compounds of formula (I).

Quinazoline embodiments of $R^8$ include a radical (f-1):

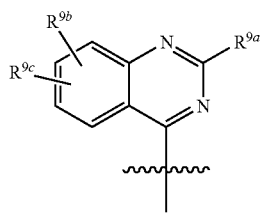

(f-1)

or in particular a radical (f-1-a):

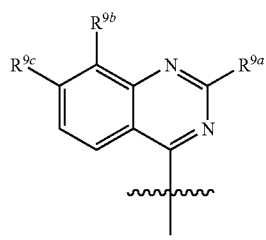

(f-1-a)

wherein $R^{9a}$, $R^{9b}$ and $R^{9c}$ have the meanings stated above in relation to $R^8$ being isoquinlinyl (such as radicals (e-1), e-1-a) etc.).

Wherein specifically $R^{9a}$ is $C_3$-$C_7$cycloalkyl, aryl or Het, any of which is optionally substituted with one, two or three (in particular with one) $R^{10}$; wherein $R^{10}$ is hydrogen, $C_1$-$C_6$alkyl, $C_1$-$C_6$alkoxy, halo such as fluoro, $C_3$-$C_7$cycloalkyl, aryl, Het (preferably mono- or disubstituted with $C_1$-$C_6$alkyl), pyrrolidinyl, piperidinyl, piperazinyl, 4-methyl-piperazinyl, thiomorpholinyl or morpholinyl, aminocarbonyl, mono or di $C_1$-$C_6$alkylaminocarbonyl; wherein the piperidinyl, morpholinyl or thiomorpholinyl may be optionally substituted with one or two $C_1$-$C_6$alkyl radicals; or $R^9$ is $C_1$-$C_6$alkoxy;

$R^{9b}$ is hydrogen, halogen, $C_1$-$C_6$alkyl, especially methyl, $C_3$-$C_7$cycloalkyl, aryl, Het, halo, in particular bromo, chloro or fluoro;

$R^{9c}$ is hydrogen or $C_1$-$C_6$alkoxy;

Favoured embodiments of $R^{9a}$ for quinazolines include aryl or Het, especially wherein $R^{9a}$ is phenyl, pyridyl, thiazolyl, oxazolyl or pyrazolyl either of which is optionally substituted with one, two or three (in particular with one) $R^{10}$ as defined.

A further embodiment of $R^{9a}$ for quinazolines is alkoxy, especially ethoxy and isopropoxy.

Embodiments of $R^{10}$ for quinazoline include hydrogen, methyl, ethyl, isopropyl, tert-butyl, alkoxy such as methoxy, halo (including dihalo, such as difluoro), saturated monocyclic amino, pyrrolidinyl, piperidinyl, piperazinyl, 4-$C_{1-6}$alkylpiperazinyl (e.g. 4-methylpiperazinyl), thiomorpholinyl or morpholinyl, $C_{1-6}$alkylamino, ($C_{1-6}$alkyl)$_2$amino, amino carbonyl, mono or di$C_{1-6}$alkylaminocarbonyl, carbocyclyl or $C_{3-7}$cycloalkyl (in particular cyclopropyl).

Preferably $R^{9a}$ in the quinazolinyl radical specified under (f-1) or (f-1-a) includes any of radicals (q), (q-1), (q-2), (q-3), (q-4), (q-5), (q-6), (q-7), (q-8)

specified above as well as:

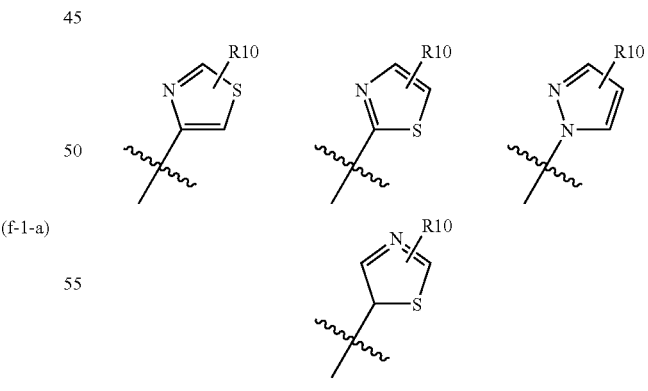

wherein $R^{10}$ is as defined above or in particular hydrogen, $C_{1-6}$alkyl (such as methyl, ethyl, isopropyl, tert-butyl), saturated monocyclic amino, pyrrolidinyl, piperidinyl, piperazinyl, 4-$C_{1-6}$alkylpiperazinyl, N-methylpiperazinyl, thiomorpholinyl or morpholinyl, $C_{1-6}$alkylamino, ($C_{1-6}$alkyl)$_2$amino or amino carbonyl, mono or di$C_{1-6}$alkylaminocarbonyl.

$R^{9a}$ for quinazolines may include:

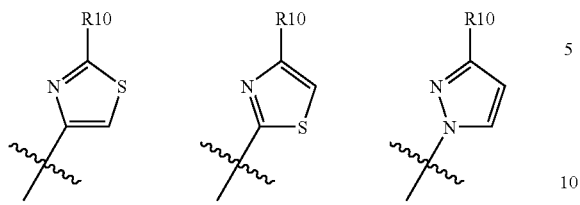

wherein $R^{10}$ is hydrogen, halogen, $C_{1-6}$alkyl (such as methyl, ethyl, isopropyl, tert-butyl), $C_{1-6}$alkylamino, $(C_{1-6}alkyl)_2$ amino, $C_{1-6}$alkylamido, morpholinyl, thiomorpholinyl or piperidin-1-yl, the morpholine and piperidine being optionally substituted with one or two $C_{1-6}$alkyl groups.

Additional $R^{9a}$ embodiments for quinazolines include phenyl substituted with one or two $R^{10}$ groups such as is hydrogen, methyl, ethyl, isopropyl, tert-butyl, methoxy, saturated monocyclic amino, $C_{1-6}$alkylamino, $(C_{1-6}alkyl)_2$amino or $C_{1-6}$alkylamido or halo (in particular fluoro).

Embodiments of $R^{9b}$ for quinazolines include hydrogen, $C_{1-6}$alkyl, halo (e.g. bromo, chloro or fluoro) especially wherein $R^{9b}$ is hydrogen or bromo.

Embodiments of $R^{9c}$ for quinazolines include hydrogen or $C_{1-6}$alkyloxy (in particular methoxy).

Specific embodiments of the compounds of formula (I) or any of the subgroups of compounds of formula (I) are those wherein $R^8$ is:

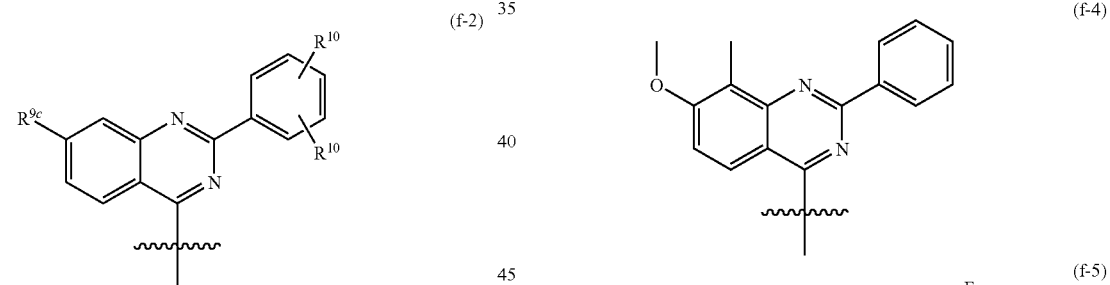

wherein $R^{10}$ and $R^{9c}$ are as specified above and in particular and $R^{9c}$ is hydrogen or $C_{1-6}$alkyloxy (e.g. methoxy) and $R^{10}$ is particularly hydrogen, methoxy or halo such as fluoro or difluoro. Conveniently, when $R^{10}$ is in the para position of the phenyl ring. Further favoured structures are compounds of formula (I) or any other of the subgroups of formula (I) wherein $R^8$ is:

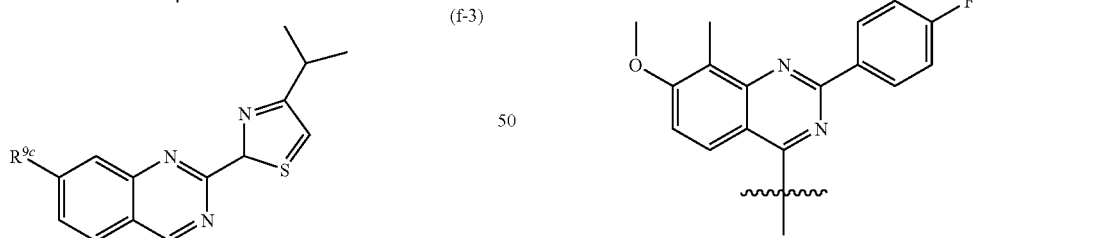

wherein $R^{10}$ and $R^{9c}$ are as specified above and in particular $R^{9c}$ is hydrogen or $C_{1-6}$alkoxy (e.g. methoxy) and $R^{10}$ is particularly hydrogen, methoxy or halo such as fluoro or difluoro. Conveniently $R^{10}$ is in the para position of the phenyl ring.

Particularly favoured compounds of this embodiment are those wherein $R^8$ is according to formulae (f-4), (f-5) or (f-6)

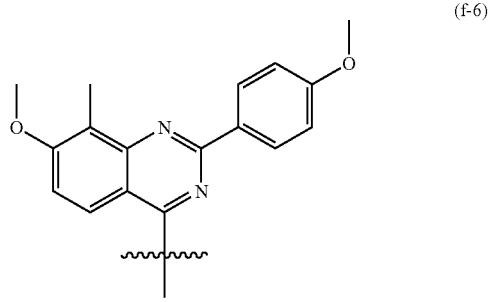

Compounds of the invention are prepared as generally described below and in detail in the experimental part. A convenient intermediate to compounds of formula (I) wherein $R^8$ is an 8-methyl substituted quinazolinyl derivative is the tri-substituted aniline of formula (II):

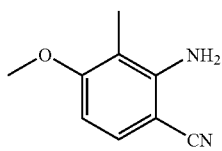
(II)

which aniline derivative constitutes a further aspect of the present invention.

Further useful intermediates for the preparation of compounds of formulae (I) are quinazolinyl derivatives having the general formula (III)

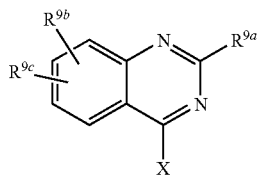
(III)

and in particular formula (III-a),

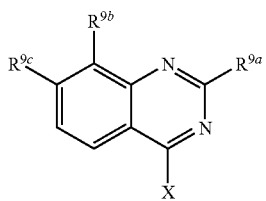
(III-a)

wherein X is OH or a leaving group such as a halide like chloride, bromide or iodide or a derivative of sulphonic acid such as a tosylate, triflate, mesylate or the like, Preferably X is OH. $R^{9a}$, $R^{9b}$ and $R^{9c}$ are as defined above for compounds of formulae (f-1) and (f-1-a). The compounds (III) and (IIIa) are a new compounds and constitutes a further aspect of the present invention.

The various embodiments described above for the quinazolinyl moiety applies also to the compounds of formulae (III) and (IIIa).

Preferred $R^{9a}$ embodiments for compounds of formula (III) and (IIIa) include pyridyl and phenyl optionally substituted with one or two $R^{10}$ groups such as hydrogen, methyl, ethyl, isopropyl, tert-butyl, saturated monocyclic amino, $C_1$-$C_6$alkylamino, ($C_1$-$C_6$alkyl)$_2$amino or $C_1$-$C_6$alkylamido or halo (in particular fluoro) especially when $R^6$ is hydrogen, methyl or bromo. Preferably the substituent is in the para position of the phenyl ring. A favoured structure for $R^{9a}$ is parafluorophenyl.

Specific embodiments of the compounds of formula (III) are those having the structure indicated in formula (III-2) and (III-3):

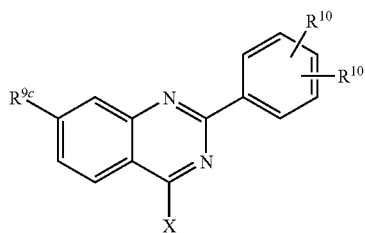
(III-2)

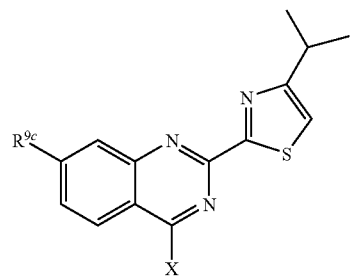
(III-3)

wherein X, $R^{10}$ and $R^{9c}$ are as specified above and in particular $R^{9c}$ is hydrogen or $C_{1-6}$alkoxy (e.g. methoxy) and $R^{10}$ is particularly hydrogen, methoxy or halo such as fluoro or difluoro. Conveniently $R^{10}$ is in the para position of the phenyl ring.

Further favoured structures for compounds of formula (III) are those according to formula (III-2-Me) and (III-3-Me):

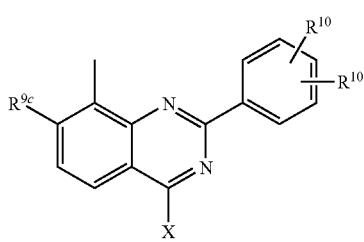
(III-2-Me)

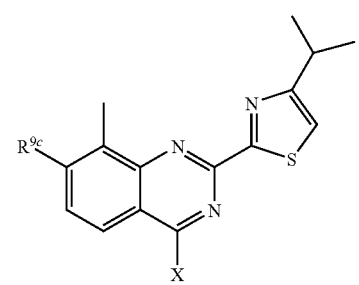
(III-3-Me)

wherein X, $R^{10}$ and $R^{9c}$ are as specified above and in particular $R^{9c}$ is hydrogen or $C_{1-6}$alkoxy (e.g. methoxy) and $R^{10}$ is particularly hydrogen, methoxy or halo such as fluoro or difluoro. Conveniently $R^{10}$ is in the para position of the phenyl ring.

Particularly favoured compounds of formula (III) are those having the formulae (III-4) or (III-5):

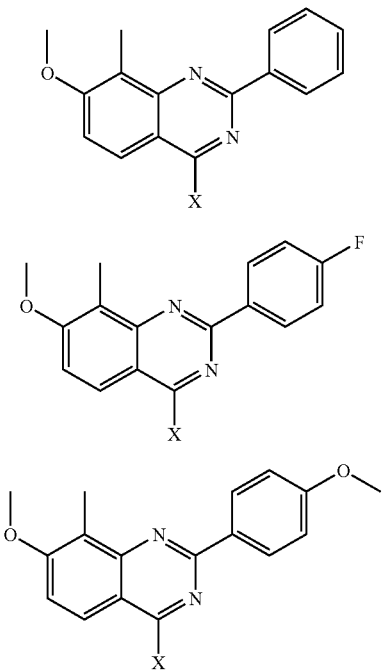

(III-4)

(III-5)

(III-6)

wherein X is as described above.

Embodiments of the invention are compounds of formula (I) or any of the subgroups of compounds of formula (I) wherein Rr is quinazolin-4-yl optionally mono, di, or tri substituted with methyl, ethyl, isopropyl, tert-butyl, methoxy, trifluoromethyl, trifluoromethoxy, fluoro, chloro, bromo, mono- or di$C_1$-$C_6$alkylamino, mono- or di$C_1$-$C_6$alkylaminocarbonyl, phenyl, methoxyphenyl, cyanophenyl, halophenyl, pyridyl, $C_1$-$C_4$alkylpyridyl, pyrimidinyl, morpholinyl, piperazinyl, $C_1$-$C_4$alkylpiperazinyl, pyrrolidinyl, pyrazolyl, $C_1$-$C_4$alkylpyrazolyl, thiazolyl, $C_1$-$C_4$alkylthiazolyl, cyclopropyl-thiazolyl, or mono- or di$C_{1-4}$alkylaminothiazolyl.

Preferred amongst the subgroups of compounds of the embodiments wherein $R^8$ is a radical (d-1)-(d-5), (e-1)-(e-3), (f-1)-(f-3) as specified above, are those compounds within these subgroups wherein is W is —O—.

Embodiments of the invention are compounds of formula (I) or any of the subgroups of compounds of formula (I) wherein $R^8$ is:

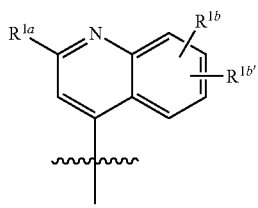

wherein $R^{1a}$ is hydrogen, $C_{1-6}$alkyl, $C_{1-6}$alkoxy, $C_{1-6}$alkylthio, mono$C_{1-6}$alkylamino, amino, $C_{3-7}$cycloalkyl, aryl, or Het; said aryl or Het being each, independently, optionally substituted with $C_{1-6}$alkyl, $C_{1-6}$alkoxy, amino, mono- or di $C_{1-6}$alkylamino; and each $R^{1b}$ and $R^{1b'}$ are, independently, hydrogen, $C_{1-6}$alkyl, $C_{1-6}$alkoxy, —NRt$^{5a}$Rt$^{5b}$, —C(=O)NR$^{5a}$R$^{5b}$, nitro, hydroxy, halo, trifluoromethyl, —C(=O)OH, or —C(=O)OR$^{6a}$.

Embodiments of the invention are compounds of formula (I) or any of the subgroups of compounds of formula (I) wherein $R^{1a}$ is selected from the group consisting of:

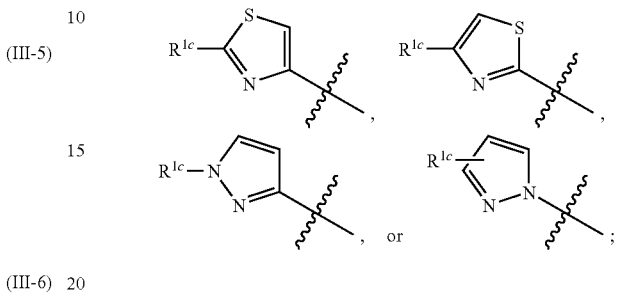

wherein $R^{1c}$ is hydrogen, halo, $C_{1-6}$alkyl, amino, or mono- or di-$C_{1-6}$alkylamino.

Embodiments of the invention are compounds of formula (I) or any of the subgroups of compounds of formula (I) wherein $R^1$ is:

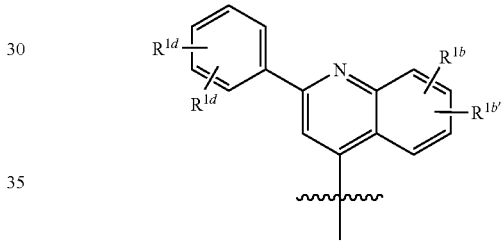

wherein $R^{1d}$ is independently hydrogen, $C_{1-6}$alkyl, $C_{1-6}$alkoxy, or halo; and each $R^{1b}$ and $R^{1b'}$ are, independently, hydrogen, $C_{1-6}$alkyl, $C_{1-6}$alkoxy, —NRt$^{5a}$Rt$^{5b}$, —C(=O)NRt$^{5a}$Rt$^{5b}$, nitro, hydroxy, halo, trifluoromethyl, —C(=O)OH, or —C(=O)OR$^{6a}$.

Further embodiments of the invention are compounds of formula (I) or any of the subgroups of compounds of formula (I) wherein $R^1$ is:

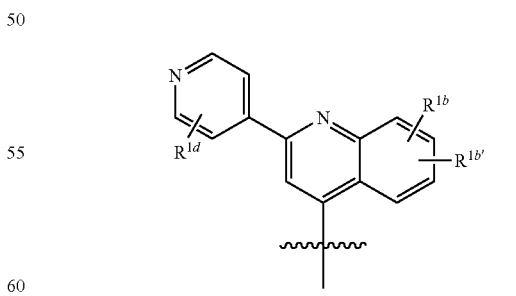

wherein each $R^{1b}$ and $R^{1b'}$ are, independently, hydrogen, $C_{1-6}$alkyl, $C_{1-6}$alkoxy, —NRt$^{5a}$Rt$^{5b}$, —C(=O)NRt$^{5a}$Rt$^{5b}$, nitro, hydroxy, halo, trifluoromethyl, —C(=O)OH, or —C(=O)ORt$^{6a}$ and $R^{1d}$ is hydrogen, $C_{1-6}$alkyl, $C_{1-6}$alkoxy, or halo Embodiments of the invention are compounds of formula (I) or any of the subgroups of compounds of formula (I) wherein $R^8$ is 7-methoxy-2-phenyl-quinolin-4-yl and W is —O—.

Embodiments of the invention are compounds of formula (I) or any of the subgroups of compounds of formula (I) wherein $R^8$ is:

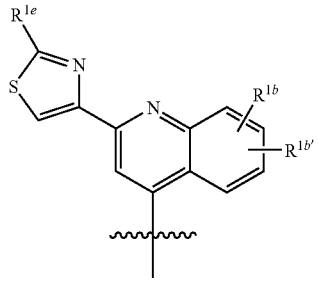

wherein $R^{1e}$ is hydrogen, $C_{1-6}$alkyl, amino, mono- or di $C_{1-6}$alkylamino, pyrrolidinyl, piperidinyl, piperazinyl, N-methylpiperazinyl, or morpholinyl; and each $R^{1b}$ and $R^{1b'}$ are, independently, hydrogen, $C_{1-6}$alkyl, $C_{1-6}$alkoxy, —NRt$^{5a}$Rt$^{5b}$, —C(=O)NRt$^{5a}$Rt$^{5b}$, nitro, hydroxy, halo, trifluoromethyl, —C(=O)OH, or —C(=O)OR$^{6a}$; preferably $R^{1b}$ is $C_{1-6}$alkoxy, most preferably methoxy.

Embodiments of the invention are compounds of formula (I) or any of the subgroups of compounds of formula (I) wherein $R^8$ is:

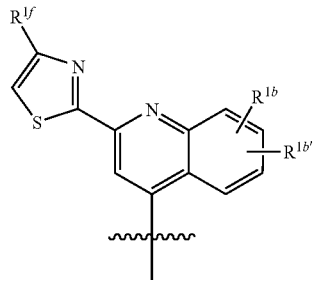

wherein $R^{1f}$ is hydrogen, $C_{1-6}$alkyl, amino, mono- or di $C_{1-6}$alkylamino, pyrrolidinyl, piperidinyl, piperazinyl, N-methylpiperazinyl, or morpholinyl; and each $R^{1b}$ and $R^{1b'}$ are, independently, hydrogen, $C_{1-6}$alkyl, $C_{1-6}$alkoxy, —NRt$^{5a}$Rt$^{5b}$, —C(=O)NRt$^{5a}$Rt$^{5b}$, nitro, hydroxy, halo, trifluoromethyl, —C(=O)OH, or —C(=O)ORt$^{6a}$; preferably $R^{1b}$ is $C_{1-6}$alkoxy, most preferably methoxy.

Preferably $R^8$ is optionally substituted $C_0$-$C_3$alkylenecarbocyclyl or $C_0$-$C_3$alkyleneheterocyclyl, especially wherein the $C_0$-$C_3$alkyl moiety is methylene or preferably a bond. Conveniently the R8 is optionally mono-, di-, or trisubstituted with $R^9$, wherein;

$R^9$ is $C_1$-$C_6$alkyl, $C_1$-$C_6$alkoxy, nitro, hydroxy, halo, trifluoromethyl, amino optionally mono- or di-substituted with $C_1$-$C_6$alkyl, amido optionally mono- or di-substituted with $C_1$-$C_6$alkyl, $C_0$-$C_3$alkyenearyl, $C_0$-$C_3$alkyleneheteroaryl, carboxy, the aryl or heteroaryl being optionally substituted with $R^{10}$; wherein $R^{10}$ is hydrogen, $C_1$-$C_6$alkyl, $C_3$-$C_7$cycloalkyl, $C_3$-$C_7$heterocyclyl, $C_1$-$C_6$alkoxy, amino optionally mono- or disubstituted with $C_1$-$C_6$alkyl, amido optionally mono- or disubstituted with $C_1$-$C_6$alkyl, sulfonyl$C_1$-$C_3$alkyl, nitro, hydroxy, halo, trifluoromethyl, carboxy or heteroaryl.

Embodiments include those wherein $R^9$ is $C_1$-$C_6$alkyl, $C_1$-$C_6$alkoxy, amino optionally mono- or disubstituted with $C_1$-$C_6$alkyl, pyrrolidinyl, piperidinyl, piperazinyl, N-methylpiperazinyl, or morpholinyl, amido optionally substituted with $C_1$-$C_6$alkyl, $C_0$-$C_3$alkylcarbocyclyl, $C_0$-$C_3$alkylheterocyclyl, bromo, chloro or fluoro, aryl or heteroaryl, the aryl or heteroaryl being optionally substituted with $R^{10}$; wherein $R^{10}$ is hydrogen, $C_1$-$C_6$alkyl, $C_3$-$C_7$cycloalkyl, $C_3$-$C_7$heterocyclyl, $C_1$-$C_6$alkoxy, amino optionally mono- or disubstituted with $C_1$-$C_6$alkyl, pyrrolidinyl, piperidinyl, piperazinyl, N-methylpiperazinyl, or morpholinyl, amido optionally mono- or disubstituted with $C_1$-$C_6$alkyl, halo, trifluoromethyl or heteroaryl Embodiments include those in the paragraph above wherein $R^{10}$ is hydrogen, $C_1$-$C_6$alkyl, $C_3$-$C_7$heterocyclyl, $C_1$-$C_6$alkoxy, amino optionally mono- or disubstituted with $C_1$-$C_6$alkyl, pyrrolidinyl, piperidinyl, piperazinyl, N-methylpiperazinyl, or morpholinyl, amido optionally mono- or disubstituted with $C_1$-$C_3$alkyl, $C_1$-$C_3$alkylamido, halo or heteroaryl, especially those wherein $R^{10}$ is methyl, ethyl, isopropyl, tert-butyl, methoxy, chloro, amino optionally mono- or di substituted with $C_1$-$C_3$alkyl, pyrrolidinyl, piperidinyl, piperazinyl, N-methylpiperazinyl, or morpholinyl, amido optionally mono- or disubstituted with $C_1$-$C_3$alkyl, Convenient values for $R^8$ include 1-naphthylmethyl, 2-naphthylmethyl, benzyl, 1-naphthyl or 2-naphthyl any of which is unsubstituted, mono, di, or trisubstituted with $R^9$ as defined.

Embodiments of $R^8$ include:

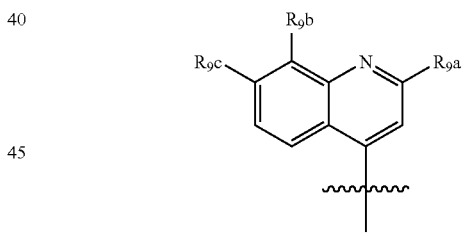

wherein $R^{9a}$ is aryl or heteroaryl either of which is optionally substituted with $R^{10}$;

wherein $R^{10}$ is hydrogen, $C_1$-$C_6$alkyl, $C_0$-$C_3$alkylcycloalkyl, $C_0$-$C_3$alkylheterocyclyl, amino optionally mono or disubstituted with $C_1$-$C_6$alkyl, pyrrolidinyl, piperidinyl, piperazinyl, N-methylpiperazinyl, or morpholinyl, amido optionally mono or disubstituted with $C_1$-$C_6$alkyl;

$R^{9b}$ is hydrogen, $C_1$-$C_6$alkyl, $C_0$-$C_3$alkylenecarbocyclyl, $C_0$-$C_3$alkylheterocyclyl, bromo, chloro or fluoro;

$R^{9c}$ is hydrogen or $C_1$-$C_6$alkoxy.

Embodiments of $R^{9a}$ include phenyl, pyridyl, thiazolyl, oxazolyl or pyrazolyl either of which is optionally substituted with $R^{10}$ as defined, especially wherein $R^{10}$ is hydrogen, methyl, ethyl, isopropyl, tert-butyl, halo (including dihalo, such as difluoro) saturated monocyclic amino, $C_1$-$C_6$alkylamino, ($C_1$-$C_6$alkyl)$_2$amino, $C_1$-$C_6$alkylamido or carbocyclyl.

Favoured $R^{9a}$ include

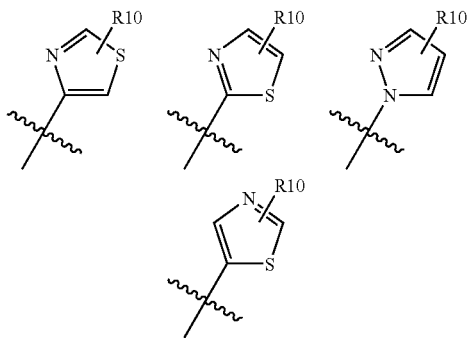

wherein $R^{10}$ is hydrogen, methyl, ethyl, isopropyl, tert-butyl, saturated monocyclic amino, $C_3$-$C_7$cycloalkyl (such as cyclopropyl) $C_1$-$C_6$alkylamino, ($C_1$-$C_6$alkyl)$_2$amino or $C_1$-$C_6$alkylamido.

Favoured $R^{9a}$ include

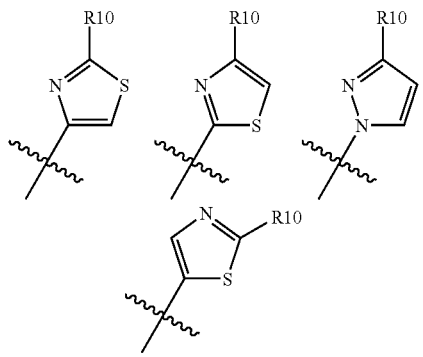

wherein $R^{10}$ is hydrogen, methyl, ethyl, isopropyl, tert-butyl, cyclopropyl, $C_1$-$C_6$alkylamino, ($C_1$-$C_6$alkyl)$_2$amino $C_1$-$C_6$alkylamido, morpholin-4-yl or piperidin-1-yl, the morpholine and piperidine optionally substituted with $C_1$-$C_3$alkyl.

Embodiments of $R^{9b}$ include hydrogen, $C_1$-$C_3$alkyl, bromo, chloro or fluoro, especially, especially methyl, hydrogen or bromo.

Embodiments of $R^{9c}$ include hydrogen or methoxy.

Embodiments of $R^8$ include:

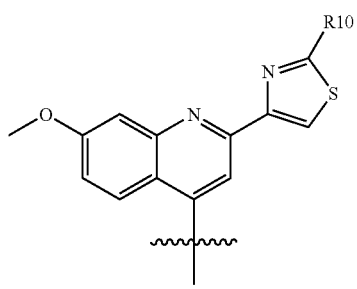

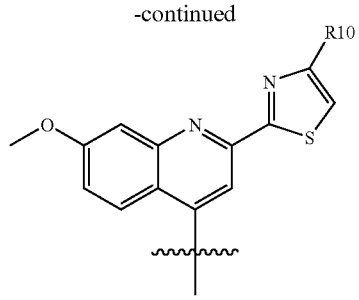

wherein $R^{10}$ is hydrogen, isopropyl, isopropylamino, dimethylamino, propanoylamino, cyclopropyl.

Embodiments of $R^8$ include isoquinolines:

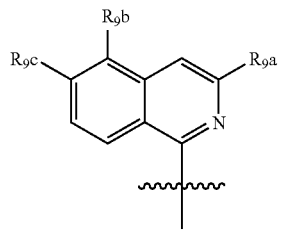

wherein $R^{9a}$ is carbocyclyl or heterocyclyl either of which is optionally substituted with $R^{10}$; wherein $R^{10}$ is hydrogen, $C_1$-$C_6$alkyl, $C_0$-$C_3$alkylcycloalkyl, $C_0$-$C_3$alkylheterocyclyl, amino optionally mono or disubstituted with $C_1$-$C_6$alkyl, pyrrolidinyl, piperidinyl, piperazinyl, N-methylpiperazinyl, or morpholinyl, amido optionally mono or disubstituted with $C_1$-$C_6$alkyl;

$R^{9b}$ is hydrogen, $C_1$-$C_6$alkyl, $C_0$-$C_3$alkylcarbocyclyl, $C_0$-$C_3$alkylheterocyclyl, bromo, chloro or fluoro;

$R^{9c}$ is hydrogen or $C_1$-$C_6$alkoxy.

Embodiments of $R^{9a}$ for isoquinoline include phenyl, pyridyl, thiazolyl, oxazolyl or pyrazolyl either of which is optionally substituted with $R^{10}$ as defined, especially wherein $R^{10}$ is hydrogen, methyl, ethyl, isopropyl, tert-butyl, amino, saturated monocyclic amino, $C_1$-$C_6$alkylamino, ($C_1$-$C_6$alkyl)$_2$amino or $C_1$-$C_6$alkylamido or saturated cyclic amino.

Favoured embodiments of $R^{9a}$ for isoquinolines include:

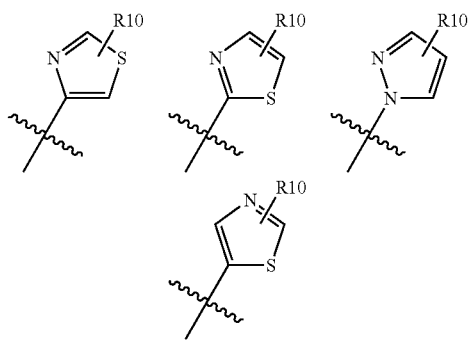

wherein $R^{10}$ is hydrogen, methyl, ethyl, isopropyl, tert-butyl, saturated monocyclic amino, $C_1$-$C_6$alkylamino, ($C_1$-$C_6$alkyl)$_2$amino or $C_1$-$C_6$alkylamido.

Favoured embodiments of $R^{9a}$ for isoquinolines include:

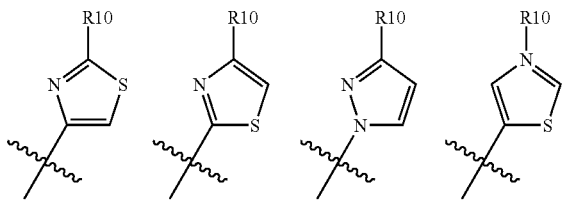

wherein $R^{10}$ is hydrogen, halogen, methyl, ethyl, isopropyl, tert-butyl, $C_1$-$C_6$alkylamino, $(C_1$-$C_6$alkyl$)_2$amino, $C_1$-$C_6$alkylamido, morpholin-4-yl or piperidin-1-yl, the morpholine and piperidine optionally substituted with $C_1$-$C_3$alkyl.

Embodiments of $R^{9b}$ for isoquinoline include hydrogen, $C_1$-$C_3$alkyl, bromo, chloro or fluoro, especially hydrogen or bromo.

Embodiments of $R^{9c}$ for isoquinoline include hydrogen or methoxy.

Isoquinoline embodiments of $R^8$ include

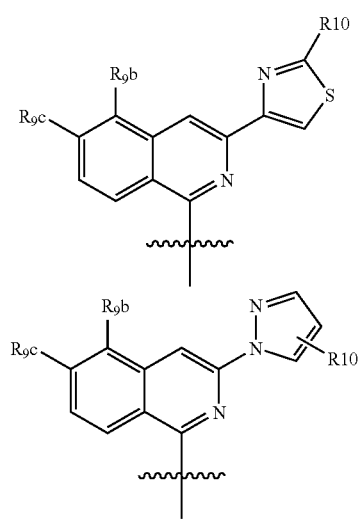

wherein $R^{9b}$ is hydrogen or bromo and $R^{9c}$ is hydrogen or methoxy.

Embodiments of the invention are compounds of formula (I) or any of the subgroups of compounds of formula (I) wherein W is —O—(C=O)—NR$^{5a}$— or in particular wherein W is —O—(C=O)—NH— and $R^8$ is aryl as defined above; or $R^8$ is phenyl optionally substituted with 1, 2 or three substituents selected from those mentioned as possible substituents of the radical aryl as in the definitions of the compounds of formula (I) or of any of the subgroups of compounds of formula (I); specifically $R^8$ is a radical of formula:

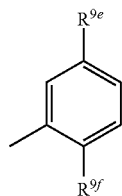

wherein
$R^{9e}$ is hydrogen, $C_{1-6}$alkyl, polyhalo$C_{1-6}$alkyl or halo;
$R^{9f}$ is —C(=O)OR$^{10}$, halo, Het or aryl; wherein Het and aryl are as defined herein and
$R^{10}$ is H or $C_{1-6}$alkyl, preferably $R^{10}$ is methyl or ethyl;

In particular, $R^{9e}$ may be hydrogen, fluoro or trifluoromethyl.

In particular, $R^{9f}$ may be —COOC$_{1-6}$alkyl (e.g. —C(=O)OEt), phenyl, thiazolyl, 1-piperidinyl or 1-pyrazolyl, the phenyl, piperidinyl and pyrazolyl groups being optionally substituted with $C_{1-6}$alkyl, in particular with methyl.

Other embodiments of the invention are compounds of formula (I) or any of the subgroups of compounds of formula (I) wherein W is —O—(C=O)—NR$^{5a}$— or, in particular, wherein W is —O—(C=O)—NH— and $R^8$ is a radical of formula:

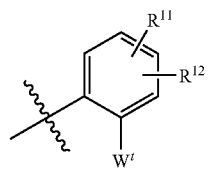

wherein $R^{10}$ and $R^{11}$ independently from one another are hydrogen, halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, $C_{1-6}$alkoxy-carbonyl, amino, azido, mercapto, $C_{1-6}$alkylthio, polyhalo$C_{1-6}$alkyl, aryl or Het; especially $R^{10}$ and $R^{11}$ independently from one another are hydrogen, halo, nitro, carboxyl, methyl, ethyl, isopropyl, t-butyl, methoxy, ethoxy, isopropoxy, t-butoxy, methylcarbonyl, ethylcarbonyl, isopropylcarbonyl, t-butyl-carbonyl, methoxycarbonyl, ethoxycarbonyl, isopropoxycarbonyl, t-butoxycarbonyl, methylthio, ethylthio, isopropylthio, t-butylthio, trifluoromethyl, or cyano;

$W^t$ is aryl or Het, or $W^t$ is —COOR$^1$, wherein $R^{10}$ is H or $C_{1-6}$alkyl, preferably methyl or ethyl.

Embodiments of $W^t$ include phenyl, naphth-1-yl, naphth-2-yl, pyrrol-1-yl, 3-pyridyl, pyrimidin-4-yl, pyridazin-3-yl, pyridazin-2-yl, 6-oxo-pyridazin-1-yl, 1,2,3-triazol-2-yl, 1,2,4-triazol-3-yl, tetrazol-1-yl, tetrazol-2-yl, pyrazol-1-yl, pyrazol-3-yl, imidazol-1-yl, imidazol-2-yl, thiazol-2-yl, pyrrolidin-1-yl, piperidin-1-yl, furan-2-yl, thien-3-yl, morpholin-4-yl; all optionally substituted with one or two substituents selected from $C_{1-6}$alkyl, polyhalo$C_{1-6}$alkyl (such as trifluoromethyl) and $C_{1-6}$alkoxycarbonyl.

Embodiments of $R^8$ for carbamates include:

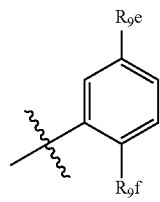

wherein $R^{9e}$ is hydrogen, $C_1$-$C_3$alkyl halo$C_1$-$C_3$alkyl or halo;

$R^{9f}$ is C(=O)O$R^1$, halo, or optionally substituted $C_3$-$C_7$heterocyclyl or $C_5$-$C_6$aryl;

wherein $R^1$ is $C_1$-$C_3$alkyl, preferably ethyl;

Embodiments of $R^{9e}$ for carbamates include hydrogen, fluoro or trifluoromethyl.

Embodiments of $R^{9f}$ for carbamates include C(=O)OEt, phenyl, thiazolyl, 1-piperidinyl or 1-pyrazolyl, the phenyl, piperidinyl and pyrazolyl being optionally substituted with methyl.

Carbamate embodiments of —W—$R^8$ include

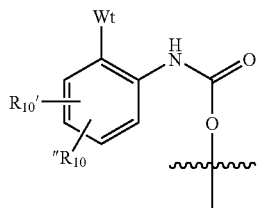

wherein $R^{10'}$ and $R^{10''}$ are independently from one another are hydrogen, halo, hydroxy, nitro, cyano, carboxyl, $C_{1-6}$alkyl, $C_{1-6}$alkoxy, $C_{1-6}$alkoxy$C_{1-6}$alkyl, $C_{1-6}$alkylcarbonyl, $C_{1-6}$alkoxy-carbonyl, amino, azido, mercapto, $C_{1-6}$alkylthio, polyhalo$C_{1-6}$alkyl, aryl or Het, especially hydrogen, halo, nitro, carboxyl, methyl, ethyl, isopropyl, t-butyl, methoxy, ethoxy, isopropoxy, t-butoxy, methylcarbonyl, ethylcarbonyl, isopropylcarbonyl, t-butyl-carbonyl, methoxycarbonyl, ethoxycarbonyl, isopropoxycarbonyl, t-butoxycarbonyl, methylthio, ethylthio, isopropylthio, t-butylthio, trifluoromethyl, or cyano;

Wt is aryl or Het, or COO$R^1$, where $R^1$ is H or $C_1$-$C_6$ alkyl, such as ethyl or methyl.

Embodiments of Wt include phenyl, naphth-1-yl, naphth-2-yl, pyrrol-1-yl, 3-pyridyl, pyrimidin-4-yl, pyridazin-3-yl, pyridazin-2-yl, 6-oxo-pyridazin-1-yl, 1,2,3-triazol-2-yl, 1,2,4-triazol-3-yl, tetrazol-1-yl, tetrazol-2-yl, pyrazol-1-yl, pyrazol-3-yl, imidazol-1-yl, imidazol-2-yl, thiazol-2-yl, pyrrolidin-1-yl, piperidin-1-yl, furan-2-yl, thien-3-yl, morpholin-4-yl; all optionally substituted with one or two substituents selected from $C_{1-6}$alkyl, halo$C_{1-6}$alkyl, such as trifluoromethyl, or $C_{1-6}$alkoxycarbonyl Embodiments of the invention are compounds of formula (I) or any of the subgroups of compounds of formula (I) wherein W is a direct bond and $R^8$ is selected from the group consisting of 1H-pyrrole, 1H-imidazole, 1H-pyrazole, furan, thiophene, oxazole, thiazole, isoxazole, isothiazole, pyridine, pyridazine, pyrimidine, pyrazine, phthalazine, quinoxaline, quinazoline, quinoline, cinnoline, 1H-pyrrolo[2,3]-b]pyridine, 1H-indole, 1H-benzoimidazole, 1H-indazole, 7H-purine, benzothiazole, benzoxazole, 1H-imidazo[4,5-c]pyridine, 1H-imidazo[4,5-b]pyridine, 1,3-dihydro-benzimidazol-2-one, 1,3-dihydro-benzimidazol-2-thione, 2,3-dihydro-1H-indole, 1,3-dihydro-indol-2-one, 1H-indole-2,3-dione, 1H-pyrrolo[2,3-c]pyridine, benzofuran, benzo[b]thiophene, benzo[d]isoxazole, benzo[d]isothiazole, 1H-quinolin-2-one, 1H-quinolin-4-one, 1H-quinazolin-4-one, 9H-carbazole, and 1H-quinazolin-2-one.

Further embodiments of the invention are compounds of formula (I) or any of the subgroups of compounds of formula (I) wherein W is a direct bond and $R^8$ is selected from the group consisting of pyrrolidine, 4,5-dihydro-1H-pyrazole, pyrazolidine, imidazolidin-2-one, pyrrolidin-2-one, pyrrolidine-2,5-dione, piperidine-2,6-dione, piperidin-2-one, piperazine-2,6-dione, piperazin-2-one, piperazine, morpholine, thiomorpholine, pyrazolidin-3-one, imidazolidine-2,4-dione, piperidine, tetrahydrofuran, tetrahydropyran, 1,4-dioxane, and 1,2,3,6-tetrahydropyridine.

Embodiments of the invention are compounds of formula (I) or any of the subgroups of compounds of formula (I) wherein W is a direct bond and $R^8$ is optionally substituted tetrazolyl as depicted below:

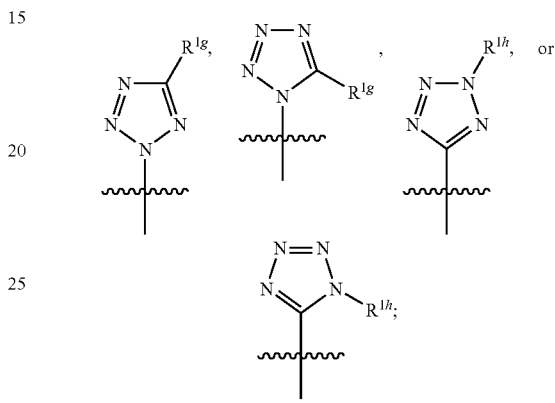

wherein $R^{1g}$ is hydrogen, $C_{1-6}$alkoxy, hydroxy, —NR$t^{5a}$R$t^{5b}$, —C(=O)R$t^7$, —SO$_p$R$t^8$, $C_{3-7}$cycloalkyl, aryl, Het, or $C_{1-6}$alkyl optionally substituted with $C_{3-7}$cycloalkyl, aryl, or Het;

$R^{1h}$ is hydrogen, —NR$t^{5a}$R$t^{5b}$, $C_{3-7}$cycloalkyl, aryl, Het, or $C_{1-6}$alkyl optionally substituted with $C_{3-7}$cycloalkyl, aryl, or Het; and R$t^{5a}$, R$t^{5b}$, R$t^7$, and R$t^8$ are as defined above.

Embodiments of the invention are compounds of formula (I) or any of the subgroups of compounds of formula (I) wherein W is a direct bond and $R^8$ is optionally substituted triazolyl as depicted below:

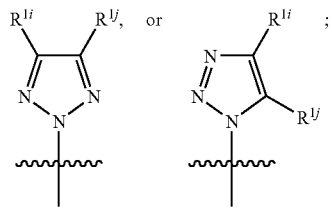

wherein $R^{1i}$ and $R^{1j}$ are each, independently, selected from the group consisting of hydrogen, halo, —C(=O)NR$t^{5a}$R$t^{5a}$, —C(=O)R$t^7$, $C_{3-7}$cycloalkyl, aryl, Het, and $C_{1-6}$alkyl optionally substituted with —NR$^{5a}$R$^{5b}$, or aryl; or alternatively, $R^{1i}$ and $R^{1j}$ taken together with the carbon atoms to which they are attached, form a cyclic moiety selected from the group consisting of aryl and Het.

Further preferred substituents for $R^8$ when W is a direct bond, include pyridazinone and derivatives thereof as shown below:

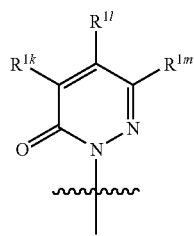

wherein $R^{1k}$, $R^{1l}$ and $R^{1m}$ are independently selected from the group consisting of hydrogen, azido, halo, $C_1$-$C_6$alkyl, —$NRt^{5a}Rt^{5b}$, $C_{3-7}$cycloalkyl, aryl, and Het; or alternatively, $R^{1k}$ and $R^{1l}$ or $R^{1l}$ and $R^{1m}$ taken together with the carbon atoms to which they are attached, form a phenyl moiety, which in turn may be optionally substituted with azido, halo, $C_1$-$C_6$alkyl, —$NRt^{5a}Rt^{5b}$, $C_{3-7}$cycloalkyl, aryl or Het.

Preferred embodiments of the invention include those wherein Ry and Ry' are the same $C_1$-$C_6$ alkyl moiety, notably methyl.

Embodiments of the invention are compounds of formula (I) or any of the subgroups of compounds of formula (I) wherein (a) A is —$NHRt^{5c}$, in particular wherein $Rt^{5c}$ is $C_{1-6}$alkyl, aryl, Het, $C_{1-6}$alkoxy, —O-aryl, or —O-Het;

(b) A is —$ORt^6$, in particular wherein $Rt^6$ is $C_{1-6}$alkyl, such as methyl, ethyl, or tert-butyl and most preferably where $Rt^6$ is hydrogen;

(c) A is —$NHS(=O)_2Rt^8$, in particular wherein $Rt^8$ is $C_{1-6}$alkyl, $C_3$-$C_7$cycloalkyl, or aryl, e.g. wherein $Rt^8$ is methyl, cyclopropyl, or phenyl;

(d) A is —$C(=O)ORt^6$, —$C(=O)Rt^7$, —$C(=O)NR^{5a}R^{5b}$, or —$C(=O)NHR^{5c}$, wherein $Rt^{5a}$, $Rt^{5b}$, $Rt^{5c}$, $Rt^6$, or $Rt^7$ are as defined above, and A preferably is —$C(=O)NHRt^{5c}$ wherein $Rt^{5c}$ is cyclopropyl;

(e) A is —$NHS(=O)_2NR^{5a}R^{5b}$, in particular wherein $Rt^{5a}$ and $Rt^{5b}$ are, each independently, hydrogen, $C_{3-7}$cycloalkyl or $C_{1-6}$alkyl, e.g. $NHS(=O)_2N(C_{1-3}alkyl)_2$.

Further embodiments of the invention are compounds of formula (I) or any of the subgroups of compounds of formula (I) wherein A is —$NHRt^{5c}$, and $Rt^{5c}$ is a Het group selected from

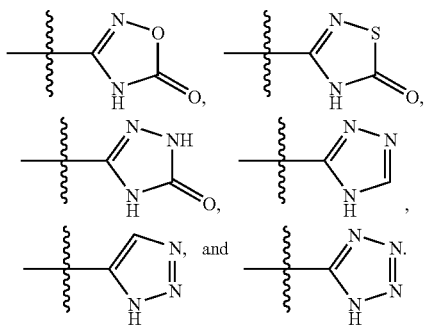

Further embodiments of the invention are compounds of formula (I) or any of the subgroups of compounds of formula (I) wherein $R^2$ is —$NHRt^{5c}$, and $Rt^{5c}$ is a $C_{1-6}$alkyl substituted with —$C(=O)ORt^6$.

In a preferred embodiment, compounds of formula (I) wherein the bond between $C_7$ and $C_8$ is a double bond, which are compounds of formula (I-c), may be prepared as outlined in the following reaction scheme:

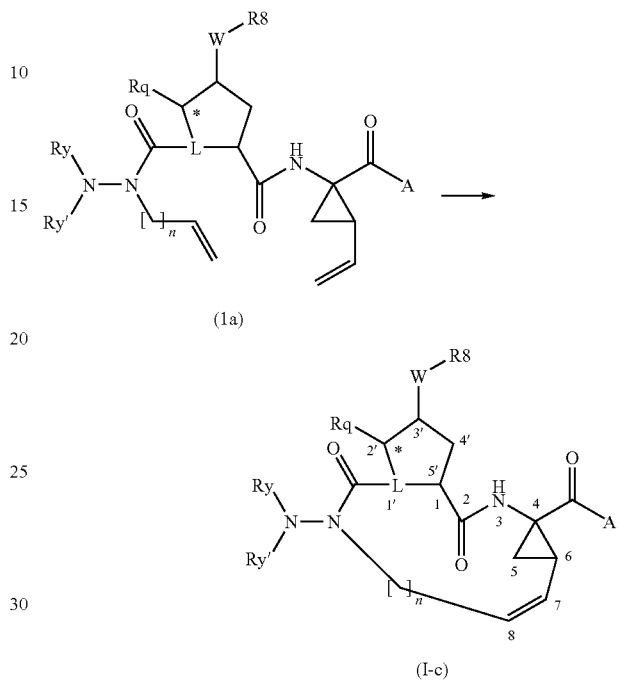

Formation of the macrocycle can be carried out via an olefin metathesis reaction in the presence of a suitable metal catalyst such as e.g. the Ru-based catalyst reported by Miller, S. J., Blackwell, H. E., Grubbs, R. H. J. Am. Chem. Soc. 118, (1996), 9606-9614; Kingsbury, J. S., Harrity, J. P. A., Bonitatebus, P. J., Hoveyda, A. H., J. Am. Chem. Soc. 121, (1999), 791-799; and Huang et al., J. Am. Chem. Soc. 121, (1999), 2674-2678; for example a Hoveyda-Grubbs catalyst.

Compounds of formula (I) wherein the link between C7 and C8 in the macrocycle is a single bond, i.e. compounds of formula (I-d), can be prepared from the compounds of formula (I-c) by a reduction of the C7-C8 double bond in the compounds of formula (I-c).

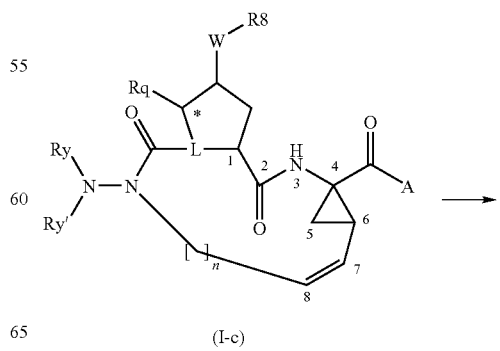

-continued

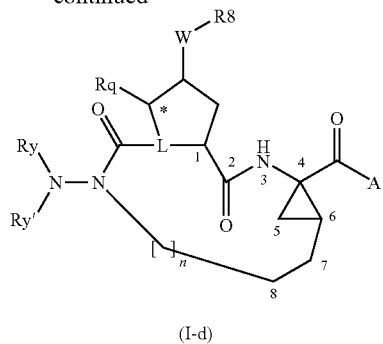

(I-d)

The R[1] group can be connected to the P1 building block at any stage of the synthesis, i.e. before or after the cyclization, or before or after the cyclization and reduction as described herein above. The compounds of formula (I) wherein A represents —NHSO$_2$R[2], said compounds being represented by formula (I-k-1), can be prepared by linking the R[1] group to P1 by forming an amide bond between both moieties. Similarly, the compounds of formula (I) wherein A represents —OR[1], i.e. compounds (I-k-2), can be prepared by linking the A group to P1 by forming an ester bond. In one embodiment, the —OR[1] groups are introduced in the last step of the synthesis of the compounds (I) as outlined in the following reaction schemes:

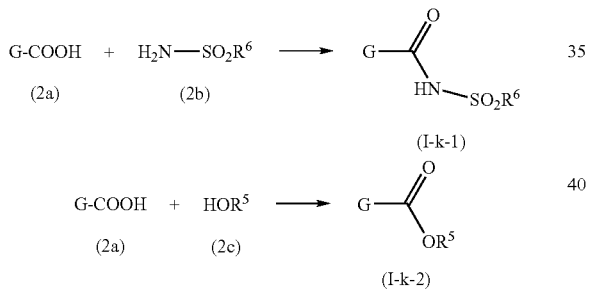

wherein G represents a group:

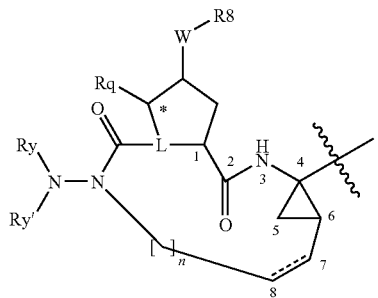

Intermediate (2a) can be coupled with the amine (2b) by an amide forming reaction such as any of the procedures for the formation of an amide bond described hereinafter. Intermediate (2a) can be coupled with the alcohol (2c) by an ester forming reaction. For example, (2a) and (2c) are reacted together with removal of water either physically, e.g. by azeotropical water removal, or chemically by using a dehydrating agent.

Intermediate (2a) can also be converted into an activated form, e.g. an acid chloride (G-CO—Cl) or a mixed acid anhydride (G-CO—O—CO—R, R being e.g. C$_{1-4}$alkyl or benzyl), and subsequently reacted with the alcohol (2c).

The compounds of formula (I) can also be prepared by reacting an intermediate (4a) with intermediate (4b) as outlined in the following reaction scheme wherein the various radicals have the meanings specified above:

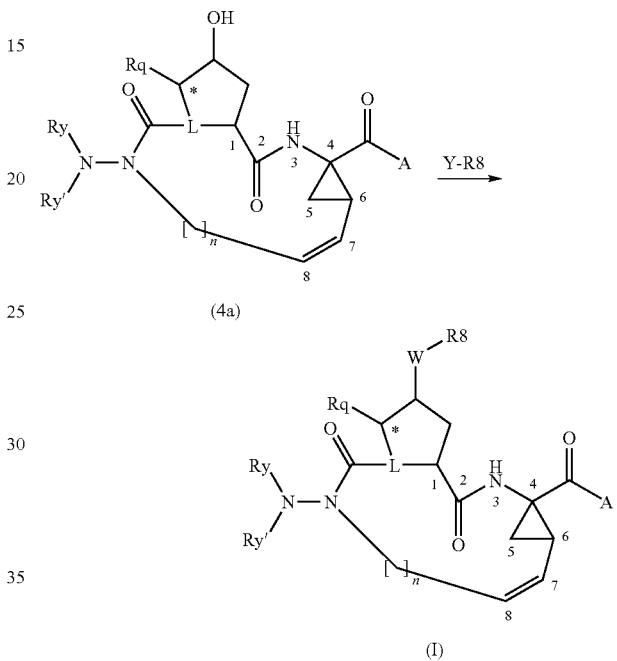

wherein Y represents hydroxy or a leaving group such as a halide, e.g. bromide or chloride, or an arylsulfonyl group, e.g. mesylate, triflate or tosylate and the like.

In one embodiment, the reaction of (4a) with YR[8] is an O-arylation reaction and Y represents a leaving group. This reaction can be conducted following the procedures described by E. M. Smith et al. (J. Med. Chem. (1988), 31, 875-885). In a particular embodiment, starting material (4a) is reacted with YR[8] in the presence of a base and the resulting alcoholate is reacted with the arylating agent YR[8], wherein Y is a suitable leaving group.

Alternatively, the reaction of (4a) with YR[8] can also be conducted via a Mitsunobu reaction (Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706).

Synthesis of the compounds of the present invention can be performed by different chemical strategies in solution or solid phase or a combination of both. The suitably protected individual building blocks can first be prepared and subsequently coupled together or precursors of the building blocks can be coupled together and modified at a later stage of the preparation of the compounds of the invention.

Coupling of the acid function of one compound to an amino function of another compound, for example coupling of two amino acid derivatives, can be carried out using standard peptide coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxysuccinic imido ester) method, Woodward reagent K-method, carbonyldiimidazole method, phosphorus reagents or oxidation-reduction methods. Some of these methods (especially the carbodiimide method) can be enhanced by adding 1-hydroxybenzotriazole or 4-DMAP.

Descriptions of coupling procedures are found in general textbooks on peptide chemistry, for example, M. Bodanszky, "Peptide Chemistry", 2nd rev ed., Springer-Verlag, Berlin, Germany, (1993) hereafter simply referred to as Bodanszky, the contents of which are hereby incorporated by reference. Examples of suitable coupling agents are N,N'-dicyclohexylcarbodiimide, 1-hydroxybenzotriazole in the presence of N,N'-dicyclohexylcarbodiimide or N-ethyl-N'-[(3-dimethylamino)propyl]carbodiimide. A practical and useful coupling agent is the commercially available (benzotriazol-1-yloxy) tris-(dimethylamino) phosphonium hexafluorophosphate, either by itself or in the present of 1-hydroxybenzotriazole or 4-DMAP. Another practical and useful coupling agent is commercially available 2-(1H-benzotriazol-1-yl)-N,N,N',N'-tetramethyluronium tetrafluoroborate. Still another practical and useful coupling agent is commercially available O-(7-azabenzotriazol-1-yl)-N,N,N',N'-tetramethyluronium hexafluorophosphate.

The coupling reaction is conducted in an inert solvent, e.g. dichloromethane, acetonitrile or dimethylformamide. An excess of a tertiary amine, e.g. diisopropylethylamine, N-methylmorpholine, N-methylpyrrolidine or 4-DMAP is added to maintain the reaction mixture at a pH of about 8. The reaction temperature usually ranges between 0° C. and 50° C. and the reaction time usually ranges between 15 min and 24 h.

Functional groups of constituent amino acids or other building blocks generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), hereafter referred to simply as Greene, the disclosures of which are hereby incorporated by reference.

The alpha-amino group of an amino acid to be coupled is typically protected. Any protecting group known in the art can be used. Examples of such groups include: 1) acyl groups such as formyl, trifluoroacetyl, phthalyl, and p-toluenesulfonyl; 2) aromatic carbamate groups such as benzyloxycarbonyl (Cbz or Z) and substituted benzyloxycarbonyls, and 9-fluorenylmethyloxycarbonyl (Fmoc); 3) aliphatic carbamate groups such as tert-butyloxycarbonyl (Boc), ethoxycarbonyl, diisopropylmethoxycarbonyl, and allyloxycarbonyl; 4) cyclic alkyl carbamate groups such as cyclopentyloxycarbonyl and adamantyloxycarbonyl; 5) alkyl groups such as triphenylmethyl and benzyl; 6) trialkylsilyl such as trimethylsilyl; and 7) thiol containing groups such as phenylthiocarbonyl and dithiasuccinoyl. The preferred amino protecting group is either Boc or Fmoc. Many amino acid derivatives are commercially available.

The alpha-amino protecting group is cleaved according to procedures well known in the art. When the Boc group is used, the methods of choice are trifluoroacetic acid, neat or in dichloromethane, or HCl in dioxane or in ethyl acetate. The resulting ammonium salt is then neutralized either prior to the coupling or in situ with basic solutions such as aqueous buffers, or tertiary amines in dichloromethane or acetonitrile or dimethylformamide. When the Fmoc group is used, the reagents of choice are piperidine or substituted piperidine in dimethylformamide, but any secondary amine can be used. The deprotection is carried out at a temperature between 0° C. and room temperature usually 20-22° C.

Once the synthesis of the compounds of the invention is completed any protecting groups are removed in whatever manner is dictated by the choice of protecting groups. These procedures are well known to those skilled in the art.

The compounds of the present invention may be prepared in general by methods known to those skilled in the art. The schemes below illustrates synthetic routes to the compounds of this invention. Other equivalent schemes, which will be readily apparent to the ordinary skilled organic chemist, may alternatively be used to synthesize various parts of the molecule as illustrated by the general schemes below, and the preparative examples that follows.

Synthesis and Introduction of the P2 Substituent

The desired $R^8$ group on the cyclic P2 scaffold can be introduced by various methods at any convenient stage of the synthesis. Scheme 1 exemplifies the introduction of a P2 substituent, $R^8$, by way of a Mitsunobu reaction. Mitsunobu, 1981, Synthesis, January, 1-28; Rano et al., Tetrahedron Lett., 1995, 36, 22, 3779-3792; Krchnak et al., Tetrahedron Lett., 1995, 36, 5, 6193-6196; Richter et al., Tetrahedron Lett., 1994, 35, 27, 4705-4706)

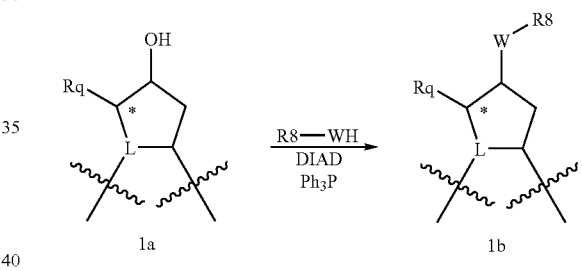

Scheme 1

Treatment of the appropriate cyclic hydroxy substituted P2 scaffold (1a) with the desired alcohol, thiol or amine, $R^8$—WH, in the presence of triphenylphosphine and an activating agent like diethyl azodicarboxylate (DEAD), diisopropyl azodicarboxylate (DIAD) or the like, provides the alkylated compound (1b). The hydroxy group may alternatively be transformed into any other suitable leaving group such as a derivative of sulphonic acid like a tosylate, mesylate or triflate or the like by subjection of the alcohol to the appropriate sulphonylating conditions, like treatment with the anhydride or halide of the desired acid in a solvent like pyridine or using the desired sulphonic acid and triphenylphosphine in the presence of DEAD in a solvent like toluene, or the hydroxy group can be converted to a halide by treatment of the alcohol with a suitable halogenating agent, for example the bromide can be prepared by using a reagent such as phosphorus tribromide or the like. The achieved leaving group can then be replaced by a desired nucleophile $R^8$—W to give the alkylated derivative (1b)

A reversed strategy can alternatively be used wherein the hydroxy compound (1a) is used as nucleophile and is treated with a base such as sodium hydride or potassium t-butoxide or the like, in a solvent like dimethylformamide (DMF) followed by reaction of the resulting alkoxide with an alkylating agent $R^8$-Lg, wherein Lg is a suitable leaving group such as a halide like chloride, bromide or iodide or a derivative of sulphonic acid or the like, provides the desired substituted derivative. An example applied to a proline derivative is described by E. M. Smith et al. in J. Med. Chem. (1988), 31, 875-885.

Alcohol (1a) can alternatively be treated with a formylating agent such as phosgene, triphosgene, a carbonyl diester or carbonyl diimidazole or the like, optionally in the presence of a suitable base such as triethyl amine, pyridine or sodium hydrogencarbonate or the like, thus providing the corresponding formyl derivative which upon reaction with an amine, $R^8NH_2$, in the presence of a base like sodium hydrogencarbonate or triethylamine, provides carbamates i.e. W is —OC(=O)NH—, whereas reaction of alcohol (1a) with an acylating agent, $R^8$—C(=O)—X, like an acid anhydride or acid halide for instance the acid chloride, to provide esters, i.e. W is —OC(=O)—. Another route to compounds wherein the P2-substituent is linked to the scaffold via a carbamate is to react alcohol 1a with the isocyanate of the P2-substituent in the presence of a base such as potassium t-butoxide.

The $R^8$ group in compounds of the present invention may also be linked directly to the cyclic scaffold, i.e. W is a bond. The $R^8$ group can then be introduced by a replacement reaction as shown in scheme 2 below, exemplified with a triazole derivative as $R^8$ group.

Scheme 2

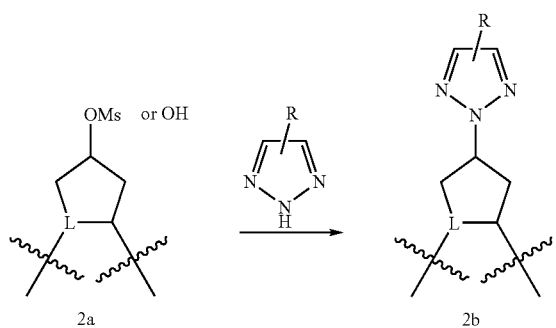

Transformation of the hydroxy group on the cyclic scaffold (2a) into a suitable leaving group such as a derivative of sulphonic acid like a mesylate, triflate, tosylate or the like followed by reaction with the desired $R^8$ group provides the substituted compound (2b). Alternatively the heterocyclic $R^8$ group can be introduced by performing a Mitsunobu reaction as previously described wherein the hydroxy group of the cyclic scaffold is reacted with a nitrogen of the heterocyclic $R^8$ group.

Compounds wherein a tetrazole derivative is attached via a carbon atom of the heterocyclic ring are conveniently prepared by building up the tetrazole moiety directly on the cyclic P2 scaffold. This can be achieved for instance by transforming the hydroxy group of the P2 precursor into a cyano group followed by reaction with an azide reagent like sodium azide. Triazole derivatives can also be built up directly on the cyclic P2 scaffold for example by transforming the hydroxy group of the P2 precursor into an azide group followed by a 3+2 cycloaddition reaction of the afforded azide and a suitable alkyne derivative.

Structurally diverse tetrazoles for use in the above described substitution or Mitsunobu reactions can be prepared by reacting commercially available nitrile compounds with sodium azide. Triazole derivatives can be prepared by reaction of an alkyne compound and trimethylsilyl azide. Useful alkyne compounds are available either commercially or they can be prepared for instance according to the Sonogashira reaction i.e. reaction of a primary alkyne, an aryl halide and triethylamine in the presence of $PdCl_2(PPh)_3$ and CuI as described for example in A. Elangovan, Y.-H. Wang, T.-I. Ho, Org. Lett., (2003), 5, 1841-1844. The heterocyclic substituent can also be modified when attached to the P2 building block either before or after coupling of the P2 building block to the other building blocks.

These methods and further alternatives for the preparation of compounds wherein W is a bond and $R^8$ is an optionally substituted heterocycle are extensively described in WO2004/072243.

Introduction of the $R^8$ group attached via an amine, amide, urea or sulphonamide, can be performed on aminosubstituted cyclic scaffolds which are commercially available or can be prepared for example from the corresponding hydroxy derivative. The hydroxy group of a desired hydroxy derivative can be transformed into an azide group for example by transforming the hydroxy group into a suitable leaving group as described above, followed by substitution of the leaving group with azide or by the use of an azide transfer agent like diphenylphosphoryl azide (DPPA). Reduction of the azide by catalytic hydrogenation or any other suitable reduction method provides the amine. The amino derivative can then be reacted in a displacement reaction with an alkylating agent of the general formula $R^8$-Lg wherein $R^8$ is as described above and Lg is a leaving group, to form compounds of general formula I, or P2 building blocks for use in the preparation of compounds of general formula I, wherein W is —NH—. Reaction of the aminosubstituted cyclic scaffold with an acid of the general formula $R^8$—C(=O)OH under standard amide coupling conditions like with a coupling agent such as O-(7-azabenzotriazol-1-yl)-N,N,N',N'-tetramethyluronium hexafluorophosphate (HATU), PyBOP® or the like in the presence of a base such as diisopropylamine (DIPEA) or N-methylmorpholine (NMM) in a solvent like dimethylformamide, provides compounds wherein the $R^8$ substituent is linked via an amide bond, whereas reaction of the amino derivative with an appropriate derivative of sulphonic acid, $R^8$—S(=O)$_2$-Lg where Lg is a leaving group for example chloride, in the presence of a base, provides sulphonamides. Compounds wherein the linkage between the cyclic scaffold and the $R^8$ group is constituted of a urea group can for example be achieved by treatment of amino proline analogue with a formylating agent, for example phosgene, to afford the corresponding chlorocarbamate followed by reaction with the desired amine. Alternatively, the amino derivative can be reacted with the carbamoyl chloride or isocyanate of the desired $R^8$ group for the formation of the urea linkage. A reversed approach in which a leaving group of the cyclic scaffold is directly replaced by a desired amino derivative $R^8$—NH$_2$, may also be used for the preparation of compounds wherein W is N.

Substituted heterocyclic P2 building blocks wherein the $R^8$ substitutent is linked to the P2 scaffold via a methylene bridge, i.e. W is —CH$_2$— in general formula I can be prepared as shown in Scheme 3, which illustrates the technique on a moiety where L is N, q is 0 and k is 1, according to the procedures described by J. Ezquerra et al., Tetrahedron, 1993, 38, 8665-8678 and C. Pedregal et al. Tetrahedron Lett., 1994, 35, 2053-2056.

Scheme 3

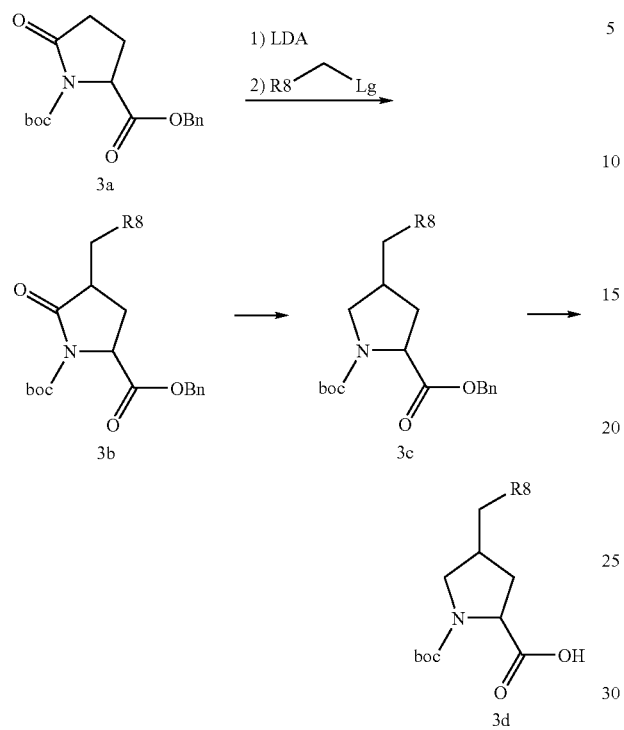

Treatment of suitably acid protected pyrrolidone or piperidinone such as commercially available Boc-pyroglutamic acid (3a) with a strong base such as lithium diisopropylamide in a solvent like tetrahydrofuran followed by addition of an alkylating agent $R^8$—$CH_2$-Lg where Lg is a suitable leaving group such as a halide like chloride or bromide, followed by reduction of the amide and deprotection of the ester gives the desired compound (3d).

It will be apparent that the above methods to introduce the $R^8$ group to the cyclic P2 scaffold can be performed at any convenient stage of the synthesis of compounds according to the present invention. For example the $R^8$ substituent can be introduced to a suitable cyclic scaffold prior to introduction of the other components of the compound or a hydroxy protected cyclic scaffold can be used throughout the synthesis and the $R^8$ group introduced as the last step of the synthesis.

Various alcohols $R^8$—OH, and alkylating agents $R^8$—X are described in WO 00/09543 and WO00/59929. An example of the synthesis wherein $R^8$ is a substituted quinoline derivative is shown in Scheme 4.

Friedel-Craft acylation of a suitable substituted aniline (4a), available either commercially or in the literature, using an acylating agent like acetyl chloride or the like in the presence of boron trichloride and aluminium trichloride in a solvent like dichloromethane provides acetophenone derivative (4b). Coupling of (4b) to a heterocyclic carboxylic acid (4c) under basic conditions, such as in pyridine, in the presence of an activating agent for the carboxylate group, for instance $POCl_3$, followed by ring closure and dehydration under basic conditions like potassium tert-butoxide in tert-butanol provides quinoline derivative (4e). Quinoline derivative (4e) can be coupled in a Mitsunobu reaction to an alcohol as described above, or the hydroxy group can be displaced by a suitable leaving group such as a halide like chloride, bromide or iodide, by treatment of quinoline (4e) with an appropriate halogenating agent for example phosphoryl chloride or the like.

A variety of carboxylic acids with the general structure (4c) can be used in Scheme 4. These acids are available either commercially or in the literature. An example of the preparation of 2-(substituted)-amino-carboxy-aminothiazole derivatives, following the procedure by Berdikhina et al. Chem. Heterocycl. Compd. (Engl. Transl.) (1991), 427-433, is shown below.

Scheme 4

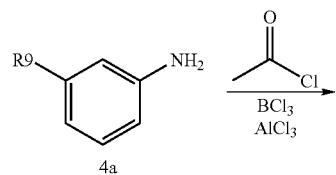

Scheme 5

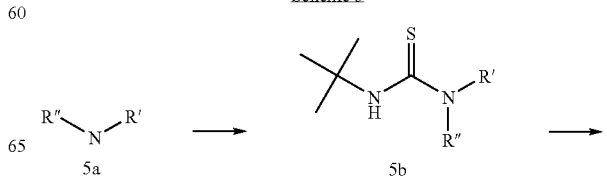

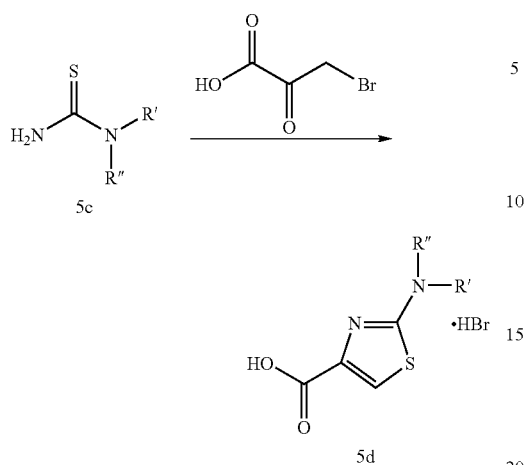

R' is $C_1$-$C_6$alkyl; R" is $C_1$-$C_6$alkyl or H

Thiourea (5c) with different alkyl substituents R' and R" can be formed by reaction of the appropriate amine (5a) with tert-butylisothiocyanate in the presence of a base like diisopropylethylamine in a solvent like dichloromethane followed by removal of the tert-butyl group under acidic conditions. Alternatively, thiourea (5c) can be formed by reaction of the amine (5a) with thiocarbonyldiimidazole and subsequently with a saturated solution of ammonia in methanol. Subsequent condensation of the afforded thiourea derivative (5c) with 3-bromopyruvic acid provides the acid (5d).

4-Substituted thiazole-2-carboxylic acids to be used in the reaction with the amine 4b in scheme 4 can be prepared as illustrated in scheme 5A.

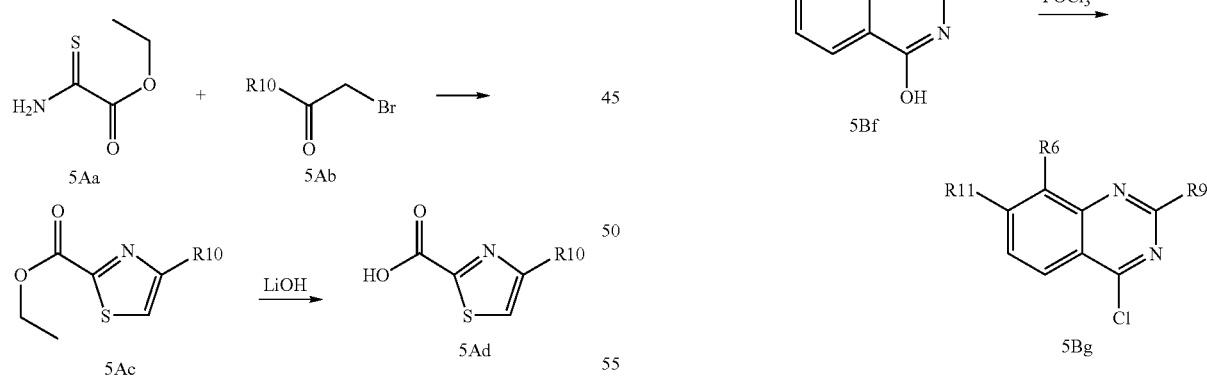

Condensation of ethyl thiooxamate (5Aa) with a desired α-bromoketone (5Ab) followed by ester hydrolysis effected by treatment with a base such as lithium hydroxide provides the thiazole carboxylic acid (5Ad). α-Bromoketones (5Ab) are commercially available or they can be prepared by α-bromination of the corresponding ketone.

An example of the synthesis of substituted quinazoline derivatives to be used as P2-substituents is shown in Scheme 5B.

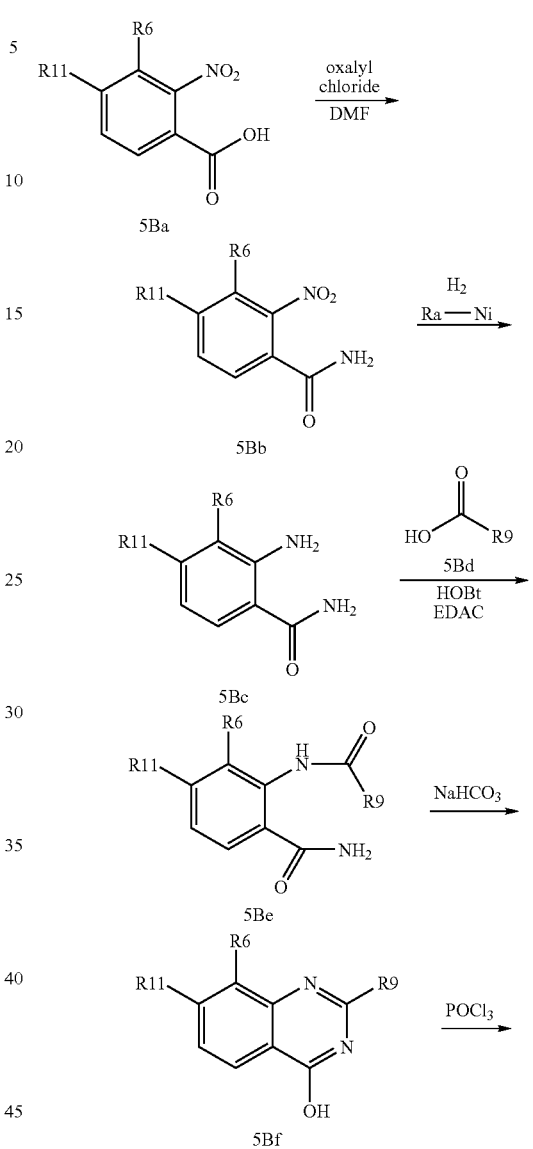

Transformation of a nitro substituted benzoic acid derivative (5Ba) to the corresponding benzamide for example by subjection of the acid to Vilsmeyer conditions followed by reduction of the nitro group using conditions like catalytic hydrogenation over Raney-nickel gives the corresponding amine (5Bc). The afforded amine can subsequently be coupled to a heterocyclic carboxylic acid (2d) under peptide coupling conditions, such as with HOBt and EDAC or any other suitable coupling agents well known in the art. Ring closure and dehydration can thereafter be effected by treatment with a base such as sodium hydrogencarbonate which provides the quinazoline derivative (5Bf). The quinazoline derivative (5Bf) can then be coupled to the hydroxy group of a P2 scaffold in a Mitsunobu reaction as described above, or the hydroxy group of the quinazoline can be displaced by a suitable leaving group such as a halide like chloride, bromide or iodide, by treatment of quinazolinol (5Bf) with an appropriate halogenating agent for example phosphoryl chloride or the like.

Synthesis and Introduction of P1 Building Blocks.

Amino acids and building blocks useful for the preparation of P1 fragments are available either commercially or in the literature, see for example WO 00/09543 from Boehringer-Ingelheim, WO2005/046712 from BMS and WO2005/030796 from Schering Corporation.

Scheme 6 shows an example of the preparation of a sulphonamide derivative to be used as a P1 fragment.

Scheme 6

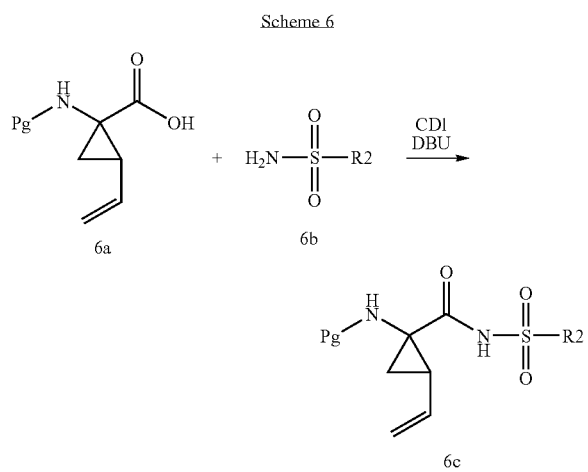

The sulphonamide group can be introduced on a suitably protected amino acid (6a) by treatment of the amino acid with a coupling agent, for example N,N'-carbonyldiimidazole (CDI) or the like, in a solvent like THF followed by reaction with the desired sulphonamide (6b) in the presence of a strong base such as 1,8-diazabicyclo[5.4.0]undec-7-ene (DBU). Alternatively the amino acid can be treated with the desired sulphonamide (6b) in the presence of a base like diisopropyl ethylamine followed by treatment with a coupling agent like PyBOP® to effect the introduction of the sulphonamide group. Removal of the amino protecting group by standard methods and subsequent coupling to a P2 moiety or precursor thereof.

P1 units comprising a sulfamid function, i.e. $R^2$ is NRaRb in general formula X, can be prepared according to the general scheme 6 above by using a sulfamide derivative in the coupling with amino acid 6a. These sulfamides can be prepared as illustrated in scheme 7 below.

Scheme 7

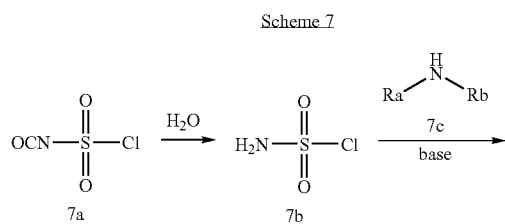

-continued

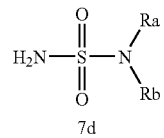

Sulfamoylchloride (7b) can be achieved by treatment of chloroisocyanate (7a) with water in a solvent like THF. Subsequent reaction with a desired amine (7c) in the presence of a base such as triethylamine gives the sulfamide derivative (7d).

P1 building blocks for the preparation of compounds according to general formula I wherein A is OH, $NHR^3$ or NRaRb can be prepared by reacting amino acid (6a) with the appropriate amine or alcohol respectively under standard conditions for amide or ester formation.

A general example of the coupling of a P1 building block to the acid function of the P2 scaffold is shown in scheme 8.

Scheme 8

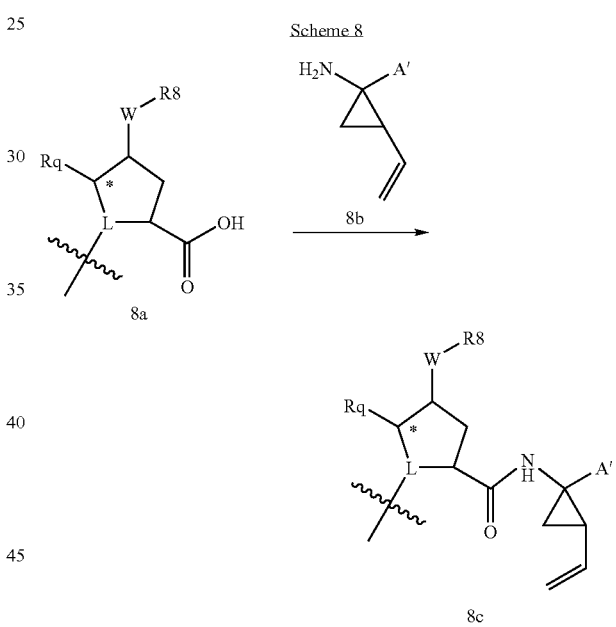

Coupling of the P1 building block (8b), prepared as described above, to the acid function of the P2 moiety using standard methods for amide bond formation, like using a coupling agent as HATU in the presence of a base such as diisopropylamine in a solvent like dimethylformamide, gives the amide (8c).

Alternatively, the sulphonamide group can be introduced at a later stage of the synthesis, for example as the last step. In this case A' in scheme 8 is an appropriately protected carboxylic acid, for example a methyl ester, and appropriately deprotected, for example with aqueous lithium hydroxide, prior to coupling of the sulphonamide group.

Compounds according to formula 1 wherein the P1 part comprises a keto amide function can be prepared according to the procedures described in WO2005/028502 and WO2005/030796. An example is shown in scheme 9.

Scheme 9

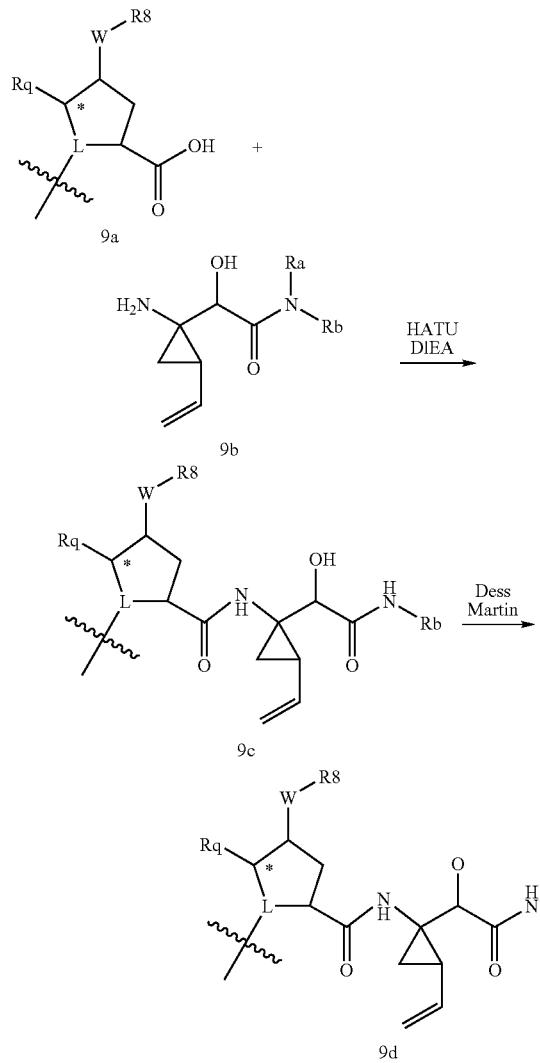

W and R8 are as defined or
W is O and R8 is a hydroxy protecting group

Coupling of the acid (9a) with an amino derivative (9b) using standard peptide coupling conditions such as treatment with any commercially available coupling reagents for example HATU or PyBOP or the like in the presence of a base like DIPEA or NMM provides the amide (9c). Oxidation of the hydroxy group by any suitable oxidation method like using Dess Martin periodinane, affords diketo amide (9d).

Aminoderivatives (9b) wherein Ra is H are described in Org. letters, 2, (2000), 2769-2772 or they can be prepared according to the procedure described in J. Med. Chem., 37, (1994) 2918-2929, which is exemplified in scheme 10.

Scheme 10

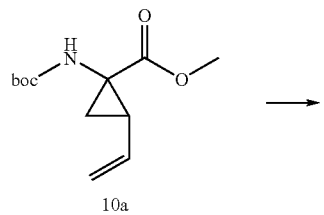

Reduction of a suitably protected amino acid derivative (10a) by reaction with a suitable hydride reagent such as LiBH$_4$ yields the corresponding aldehyde. Conversion of the aldehyde to the cyanohydrine effected for example by treatment with potassium cyanide or acetone cyanohydrine followed by acidic hydrolysis and subsequent treatment with di-tert-butyl dicarbonate provides the α-hydroxy acid (10b). Coupling of the acid with a desired amine using standard peptide conditions then gives the amide (10d).

Introduction of a Urea Linked Hydrazine to a Heterocyclic P2 Scaffold

The hydrazine moiety group linked via a urea functionality to the P2 scaffold, can be introduced as depicted in scheme 11, which illustrates the technique with a variant in wherein P2 is a 5-membered ring.

Scheme 11

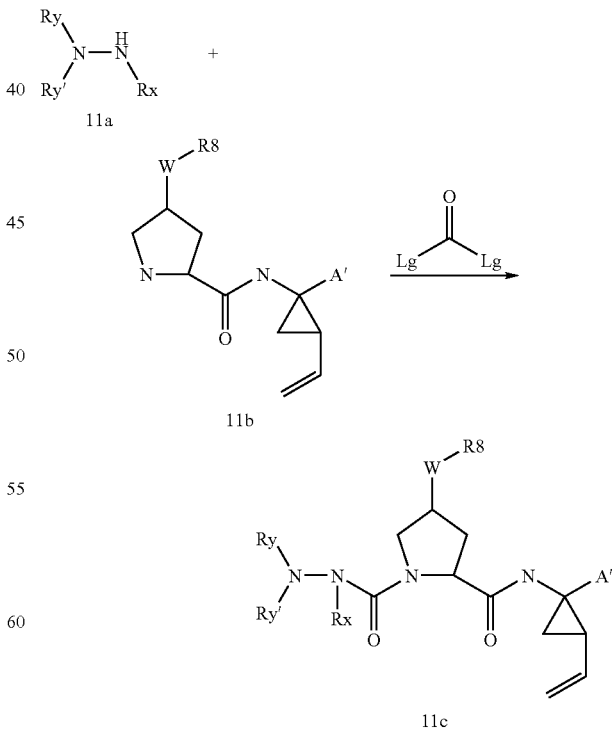

W and R8 are as defined or W is O and R8 is a hydroxy protecting group
Rx is an ω-unsaturated 5-8 membered alkylene chain
A' is a protected carboxylic acid, substituted amide or sulphone amide or HCR4R4'.

Reaction of hydrazine derivative (11a) with a formylating agent such as p-nitrophenyl chloroformate, carbonyl diimidazole, phosgene or the like in the presence of a base like sodium hydrogencarbonate followed by addition of the P2 building block (1b) provides the urea derivative (11c).

Suitably trialkylated hydrazine derivatives to be used in scheme 11 can be prepared by alkylation of a desired N,N-dialkyl hydrazine using any convenient alkylation method. These methods are extensively described in the literature and a typical example is shown in scheme 12.

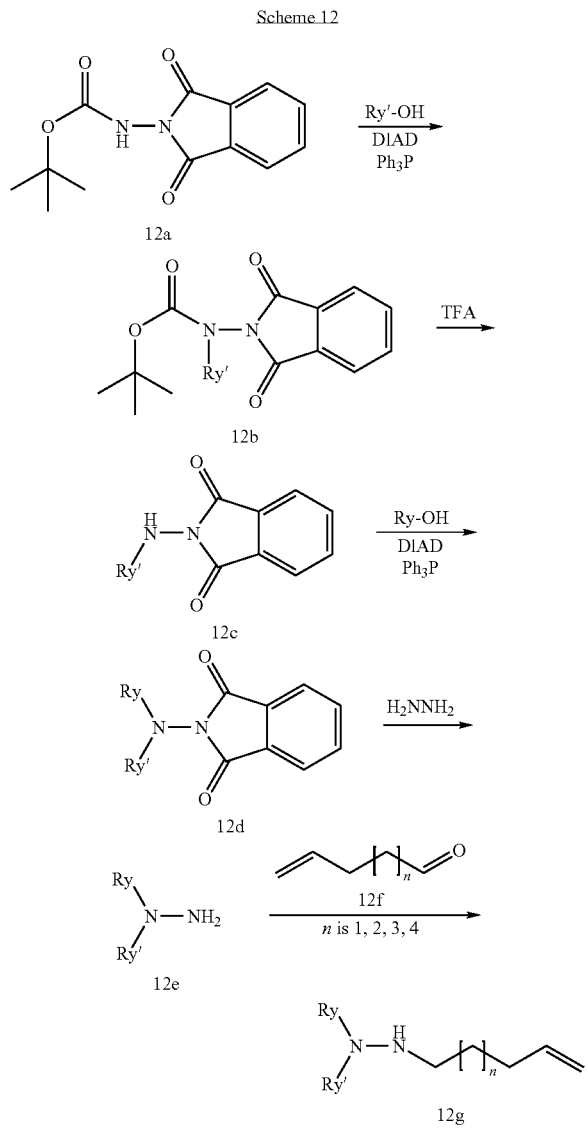

Reaction of a suitably protected hydrazine derivative, for example (1,3-dioxo-1,3-dihydro-isoindol-2-yl)-carbamic acid tert-butyl ester (12a), which is easily prepared for example from commercially available 2-amino-isoindole-1,3-dione, with a desired alcohol, Ry-OH, under Mitsunobu conditions provides N-alkylated hydrazine compound (12b). Removal of the boc group by standard methods, like acidic treatment followed by introduction of a desired Ry group effected for example by a Mitsunobu reaction provides the dialkylated derivative (12d). Removal of the phtalimido group effected by treatment with hydrazine or a derivative thereof like hydrazine hydrate or hydrazine acetate provides the primary hydrazine (12e) which can be alkylated by performing a reductive amination reaction with the appropriate ω-unsaturated aldehyde (12f) using a reducing agent such as NaCNBH$_4$. Aldehydes (12f) are conveniently prepared by oxidation of the corresponding alcohol by a suitable oxidation method like for example with N-methyl morpholine oxide and tetrapropylammonium perruthenate in a solvent like dichloromethane. which yields the alkylated hydrazine derivative (12e).

Synthesis of Compounds Containing a Carbocyclic P2 Unit

A typical route to compounds containing a saturated carbocyclic P2 scaffold i.e. L is CH in general formula 1, is shown in Scheme 14.

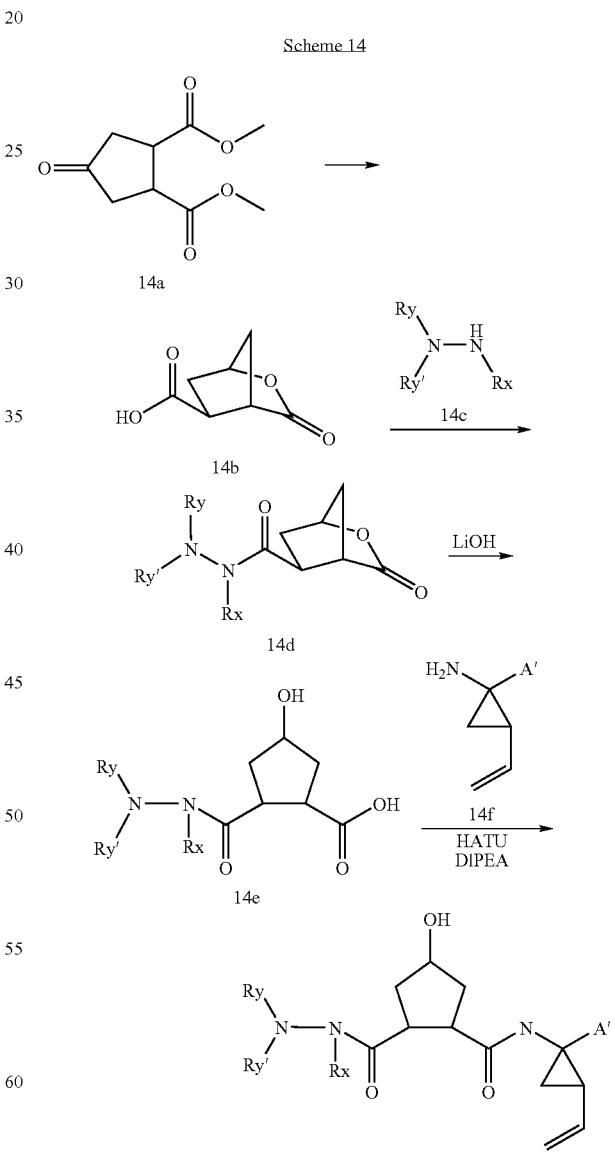

Rx is an ω-unsaturated 5-8 membered alkyl chain.
A' is a protected carboxylic acid, substituted amide or sulphone amide'.

The saturated cycloalkyl scaffold (14b) can be prepared, for example, from 3,4-bis(methoxycarbonyl)cyclopentanone (14a), described by Rosenquist et al. in Acta Chem. Scand. 46 (1992) 1127-1129 by reduction of the keto group with a reduction agent like sodium borohydride in a solvent like methanol followed by hydrolysis of the esters and finally ring closure in acetic anhydride in the presence of pyridine. The provided bicyclic acid (14b) can then be coupled to the amine function of the desired hydrazine derivative (14c) using conventional peptide coupling conditions like with HATU and diisopropyl amine in a solvent like dimethyl formamide to give (14d). Lactone opening of (14d) with for example lithium hydroxide provides the acid (14e) which subsequently can be coupled to the amino group of a P1 building block or a precursor of a desired P1 fragment (14f), using conventional peptide coupling conditions. Introduction of the $R^8$-group of the carbocycle can then be performed for example by a Mitsunobu reaction with the appropriate alcohol as described above or by any other suitable method previously described.

Scheme 15 shows an alternative route towards compounds of formula I comprising a saturated P2 scaffold where the building blocks are introduced in the reversed order, i.e. the P1 fragment is introduced before the hydrazine moiety.

(15e) using the peptide coupling conditions as described above provides the hydrazide derivative (15f).

An unsaturated P2 scaffold useful for the preparation of compounds of formula I can be prepared as illustrated in scheme 16.

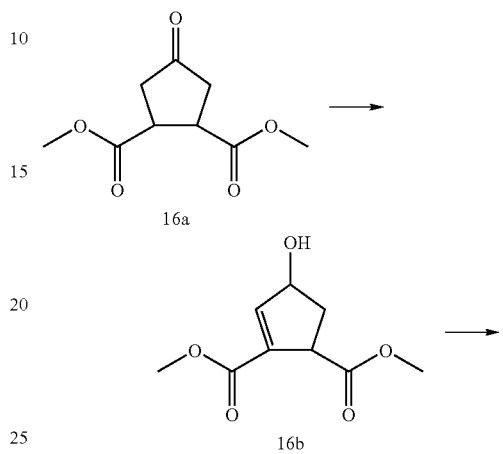

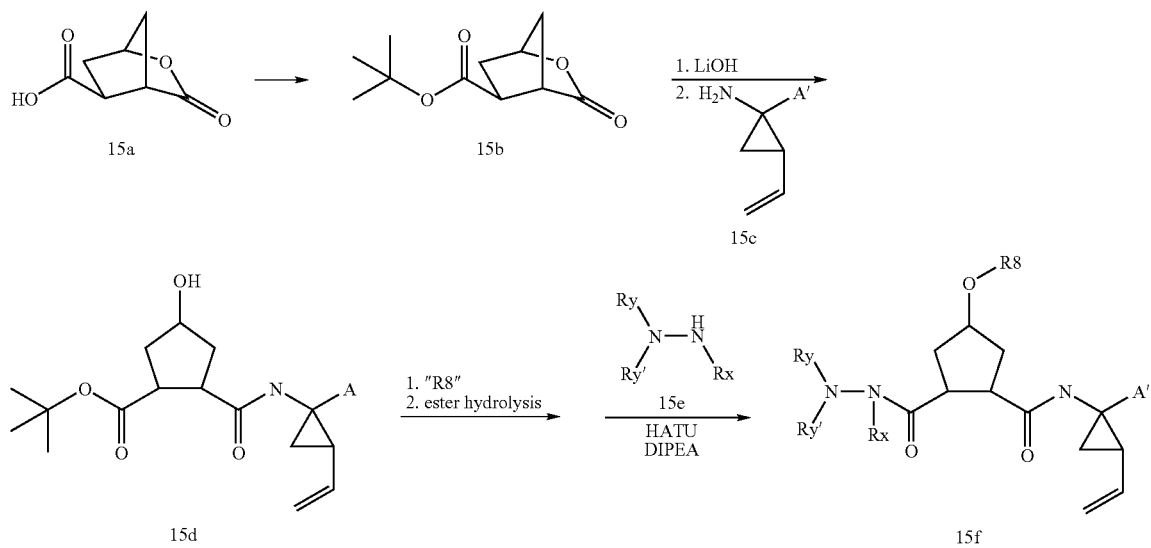

Rx is an ω-unsaturated 5 to 8 membered alkyl chain.
A' is a protected carboxylic acid, substituted amide or sulphone amide.

Protection of the acid group of (15a) for example as the tert-butyl ester by treatment with di-tert-butyl dicarbonate in the presence of a base like dimethylaminopyridine and triethylamine in a solvent like dichloromethane provides ester (15b). Lactone opening using for example lithium hydroxide and subsequent coupling of a P1 building block (15c) as described in scheme 12 or directly by the amine group of the P1 fragment provides (15d). Introduction of the $R^8$-group as described above followed by removal of the acid protecting group by subjection of the ester to acidic conditions like trifluoroacetic acid and triethylsilane in a solvent like methylene chloride and finally coupling of the hydrazine moiety -continued

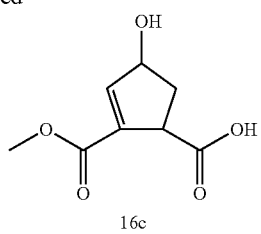

A bromination-elimination reaction of 3,4-bis(methoxy-carbonyl)cyclopentanone (15a) as described by Dolby et al. in J. Org. Chem. 36 (1971) 1277-1285 followed by reduction of the keto functionality with a reduction agent like sodium borohydride provides the unsaturated hydroxy compound (15b). Selective ester hydrolysis using for example lithium hydroxide in a solvent like a mixture of dioxane and water provides hydroxy substituted monoester derivative (15c).

A P2 scaffold wherein Rq is other than hydrogen, such as a methyl, can be prepared as shown in scheme 17.

compound (17f). The tert-butyl ester (17e) can be prepared by treatment of the corresponding commercially available acid (17d) where k' is 1 to 3 with di-tert-butyl dicarbonate in the presence of a base like dimethylaminopyridine. Cyclisation of (17f) by an olefin metathesis reaction performed as described above provides cyclopentene derivative (17g). Stereoselective epoxidation of (17g) can be carried out using the Jacobsen asymmetric epoxidation method to furnish the epoxide (17h). Finally, addition of a base like DBN (1,5-diazabicyclo-[4.3.0]non-5-ene) yields the alcohol (17i).

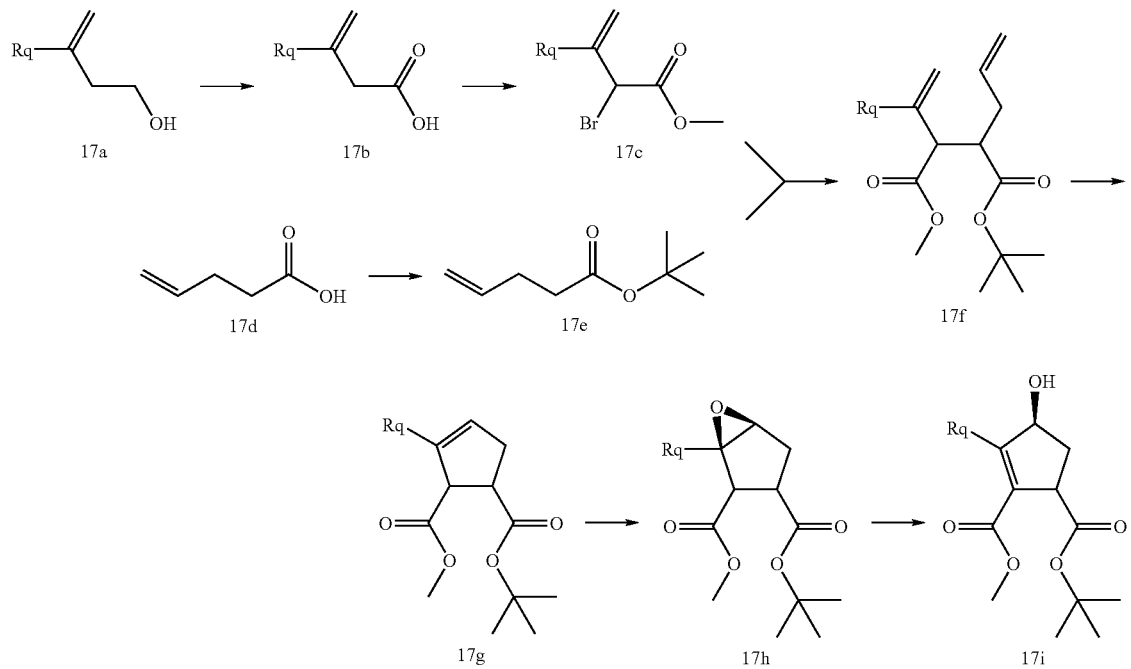

Scheme 17

Oxidation of commercially available 3-methyl-3-buten-1-ol (17a) by the use of an oxidation agent like pyridinium chlorochromate followed by treatment with acetyl chloride, bromine and methanol provides the α-bromo ester (17c). The afforded ester (17c) can then be reacted with the enolate of (17e), achieved for example by treatment of the corresponding tert-butyl ester with a base such as lithium diisopropyl amide in a solvent like tetrahydrofuran, to give the alkylated Optionally the double bond of compound (17i) can be reduced for example by catalytic hydrogenation using a catalyst like palladium on carbon which provides the corresponding saturated compound.

The afforded cyclic scaffolds can then be used, as described above, to complete the synthesis of compounds of formula 1. An example is shown in scheme 18.

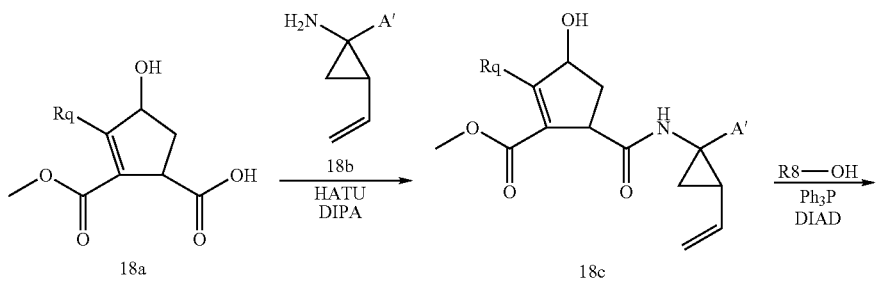

Scheme 18

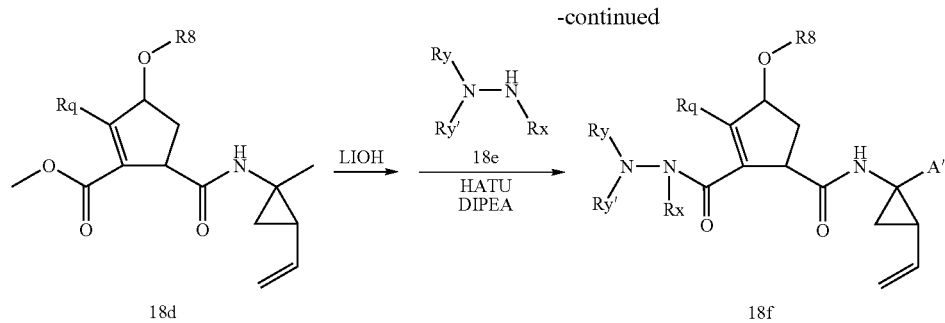

18d

Rx is an ω-unsaturated 5 to 8 membered alkylene chain.
A' is a protected carboxylic acid, substituted amide or sulphone amide.

The amino group of a P1-building block or a suitable precursor thereof (18b) can be coupled to the acid of the cyclopentene derivative (18a) using standard amide coupling conditions such as using HATU in the presence of a base like diisopropyl phenylamine or the like, followed by introduction of the $R^8$-substituent for example by Mitsunobu conditions as described above to provide (18d). Hydrolysis of the remaining ester and subsequent amide coupling of a desired P3 or P3-P4 building block (18e) optionally followed by manipulations of the P1 part provides cyclopentene containing compounds (18f) according to general formula VI. When $R^7$, $R^{7'}$ and A' contain functional groups, these are optionally suitably protected by methods recognized by persons skilled in the art, see for example Bodanzky or Greene cited above.

Macrocyclization

The macrocycle present in the compounds of the invention is typically formed by an olefin metatehsis reaction (macrocyclization). The substituent W—$R^8$ of the cyclic P2 scaffold can be introduced by any of the previously described strategies before or after formation of the macrocycle.

A typical route to macrocyclic urea compounds is shown in Scheme 19.

Scheme 19

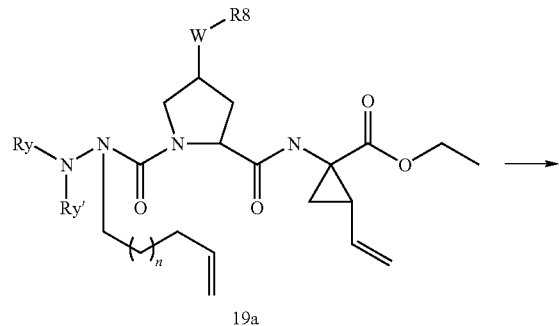

19a

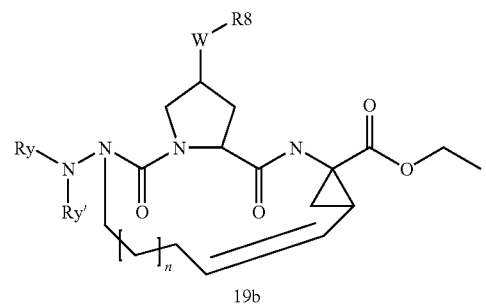

19b n = 1, 2, 3, 4
W-R8 is as defined or W is O and R8 is a hydroxy protecting group Compound (19a), prepared as described above, can be transformed into a macrocyclic compound by performing an olefin metathesis reaction. A Ru-based catalyst such as the one reported by Miller, S. J., Blackwell, H. E.; Grubbs, R. H. J. Am. Chem. Soc. 118, (1996), 9606-9614, Kingsbury, J. S., Harrity, J. P. A., Bonitatebus, P. J., Hoveyda, A. H., J. Am. Chem. Soc. 121, (1999), 791-799 and Huang et al., J. Am. Chem. Soc. 121, (1999), 2674-2678 can be used to effect the metathesis reaction. It will also be recognized that catalysts containing other transition metals such as Mo can be used for this reaction. Optionally the double bond is reduced using standard hydrogenation methods well known in the art thus giving the corresponding saturated macrocyclic derivative.

The macrocyclisation described in Scheme 19 can also be applied to compounds comprising a saturated or unsaturated carbocyclic P2 scaffold as exemplified in scheme 20.

Scheme 20

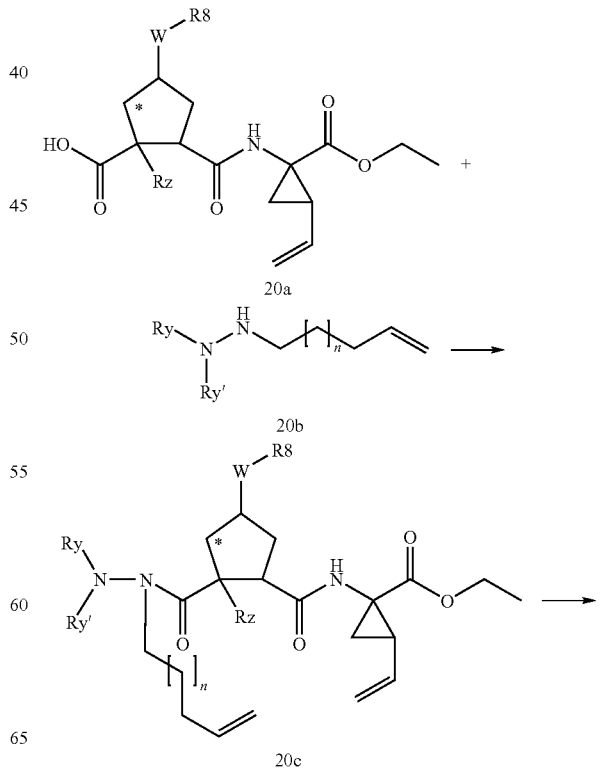

-continued

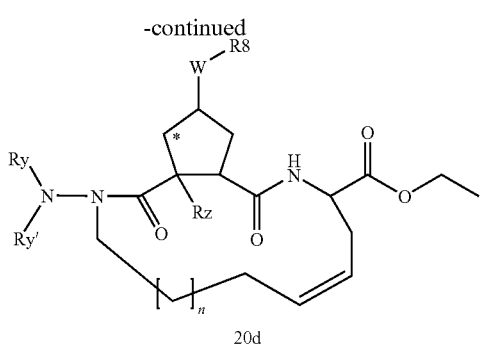

20d

W-R8 is as defined or W is O and R8 is a hydroxy protecting group
n is 1, 2, 3 or 4

Coupling of the hydrazine derivative (20b) to a P2-P1 building block (21a), prepared as desired above, using standard peptide coupling conditions such as with HATU in the presence of a suitable base for instance diisopropylamine provides intermediate (20c). Ring closure of (20c) by an olefin metathesis reaction as described in scheme 19 gives the macrocyclic compound (20d).

Alternatively, the N-alkylation of the hydrazine moiety can be performed after the macrocyclisation step as outlined in scheme 21.

Coupling of a suitably protected, for example boc protected, alkenyl hydrazine (21a) with a P2 building block followed by a ring closing metathesis reaction as described above in schemes, provides macrocyclic compound (21b). Removal of the boc group by standard methods such as treatment with TFA in dichloromethane followed by alkylation with a suitable alkylating agent such as an alkyl halide for example methyl iodide in the presence of a base like sodium hydride provides the dilakylated compound (21f). N-alkylated carbazates (21a) are conveniently prepared for instance by reaction of commercially available tert-butylcarbazate with a desired co-unsaturated aldehyde in a reductive amination reaction.

When intermediates in the above described schemes contain a functional group(s), these are suitably protected where appropriate and subsequently deprotected by methods recognized by persons skilled in the art. For an extensive description see for example Bodanzky or Greene cited above.

A number of specific synthesis routes to prepare the compounds of formula (I) or particular subgroups of compounds of formula (I) are outlined in the following schemes in somewhat more detail.

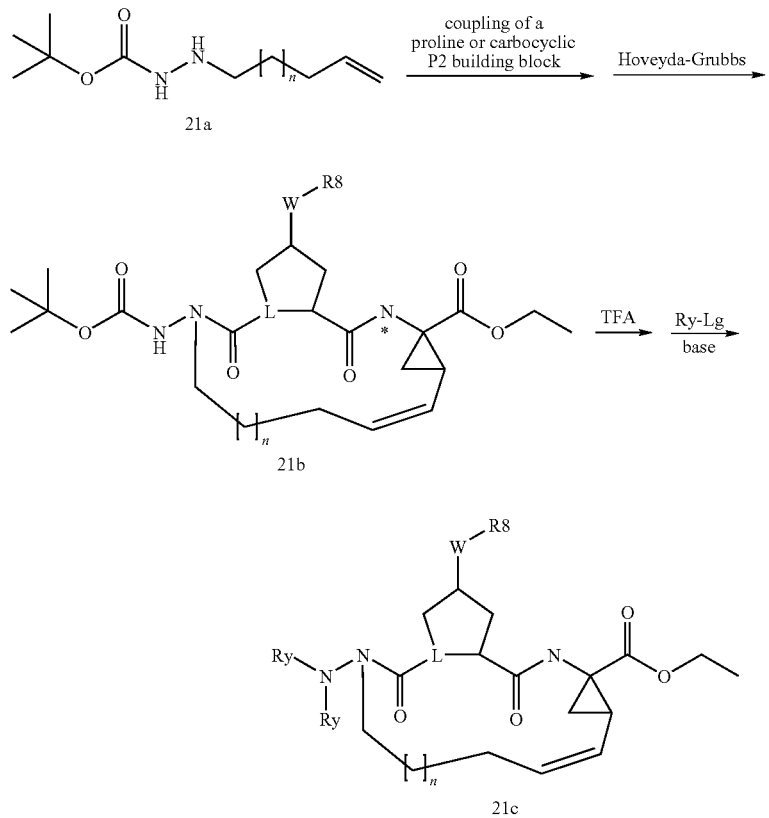

n is 1, 2, 3 or 4
W-R8 is as defined or
W is O and R8 is a hydroxy protecting group Scheme 30

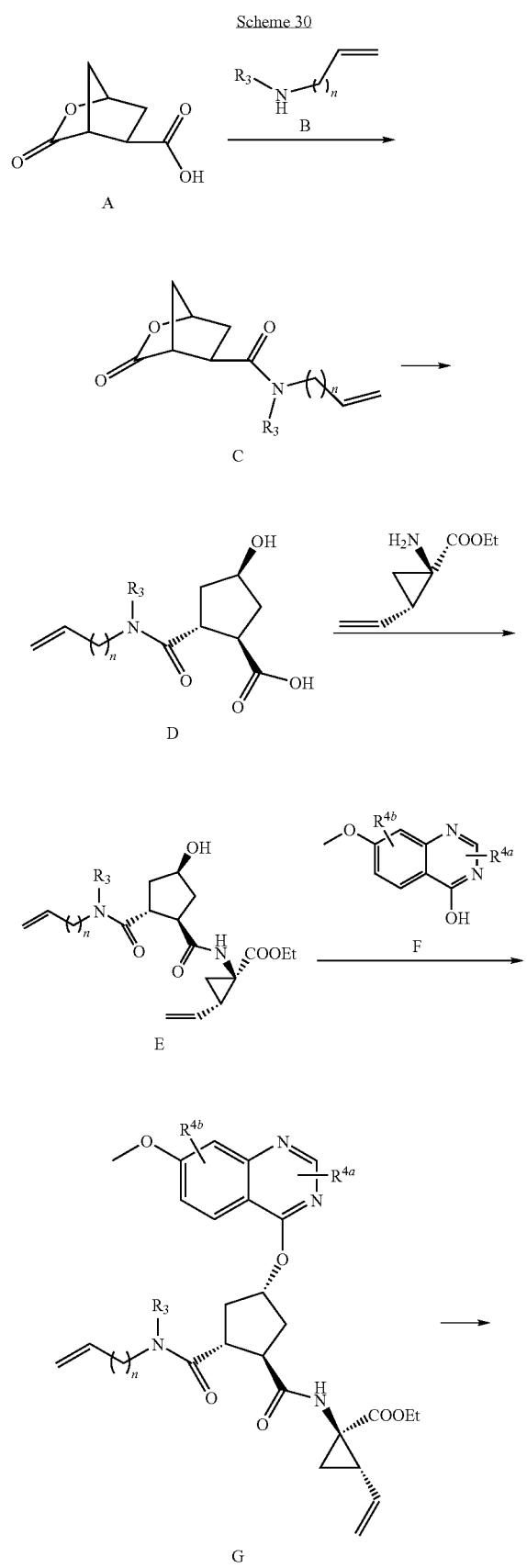

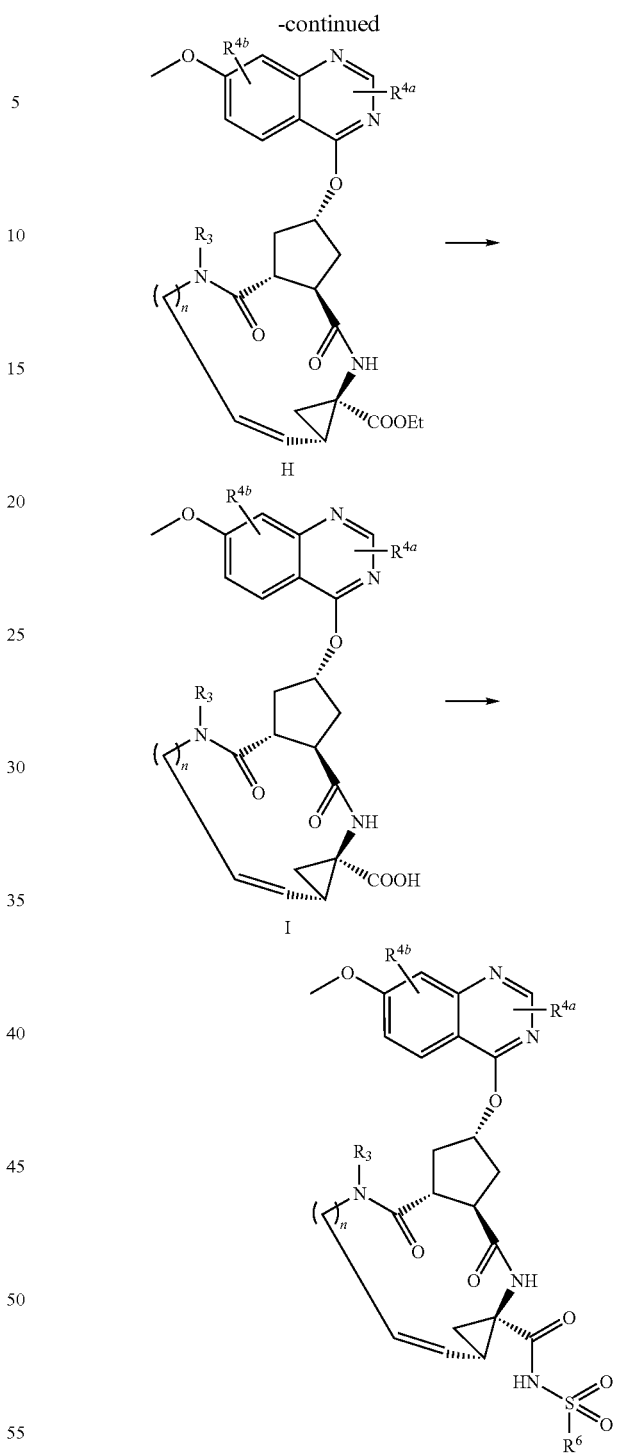

Compounds of the present invention can be synthesized, as shown in Scheme 30, from compounds of Formula A, B and F. The lactone A is coupled with an $C_{3-10}$alkenylamine of structure B, in the presence of peptide coupling agent, such as HATU or EDCI/HOAt in presence of a base, such as DIPEA, to form a compound of Formula C. The subsequent lactone opening and coupling with 1-(amino)-2-(vinyl)cyclopropane-carboxylic acid ethyl ester in the presence of peptide coupling agent, such as HATU or EDCI/HOAt in presence of a base, such as DIPEA, affords a compound of Formula E. Compounds E can be coupled to an quinazoline of Formula F using a Mitsunobu type reaction. The resulting diolefin G can be submitted to ring closure using an olefin metathesis catalyst, such as the Hoveyda-Grubbs catalysts, or Bis(tricyclohexyl-phosphine)[(phenylthio)methylene]ruthenium (IV) dichloride, Bis(tricyclohexyl-phosphine)-3-phenyl-1H-inden-1-ylideneruthenium (IV) dichloride (Neolyst M1®), in an appropriate solvent such as 1,2-dichloroethane, dichloromethane or toluene, to form a compound of Formula H, which can be hydrolyzed to the corresponding acid of Formula I. The acid of formula I is coupled with $R^6SO_2NH_2$, in presence of peptide coupling agent, such as CDI or EDAC, and in presence of a base such as 1,8-diazabicyclo[5.4.0]undec-7-ene (DBU) or DMAP to provide a compound of Formula J.

-continued

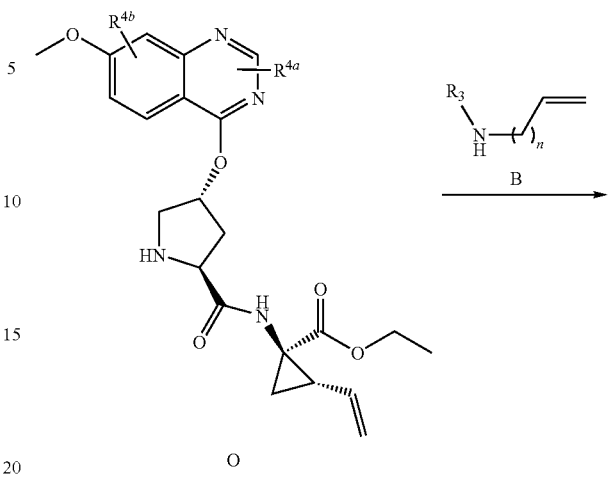

Scheme 31

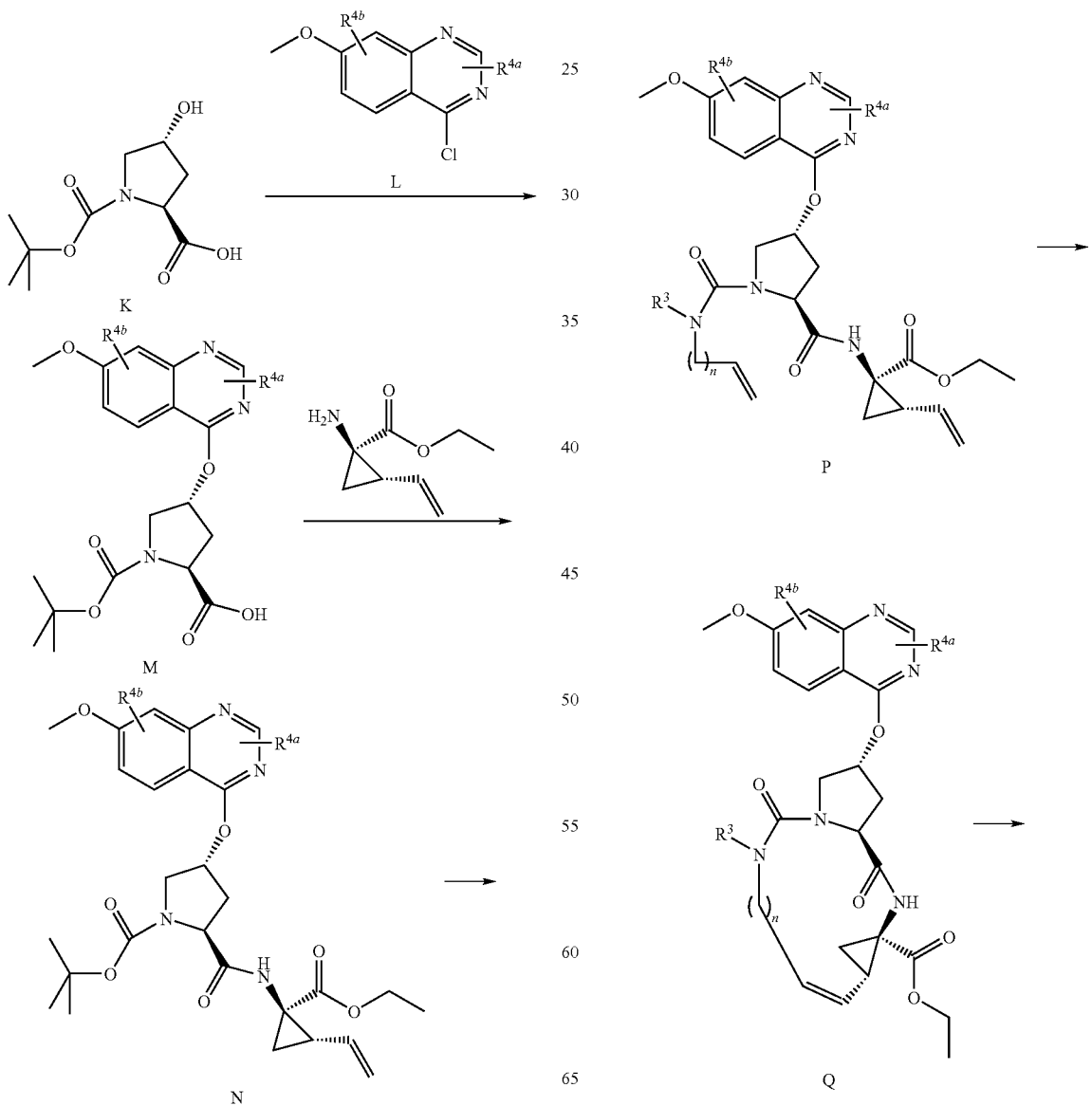

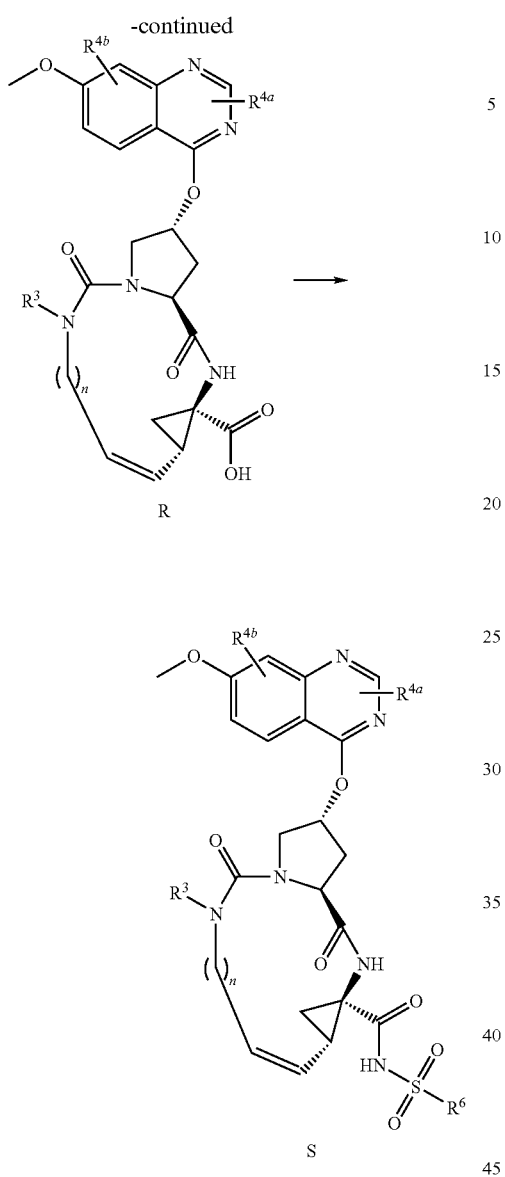

(Neolyst M1®), in an appropriate solvent such as 1,2-dichloroethane, dichloromethane or toluene, to form a compound of Formula Q, which can be hydrolyzed to the corresponding acid of Formula R. The acid of formula R is coupled with $R^6SO_2NH_2$, in presence of peptide coupling agent, such as CDI or EDAC, and in presence of a base such as 1,8-diazabicyclo[5.4.0]undec-7-ene (DBU) or DMAP to provide a compound of Formula S.

An alternative method for the synthesis of compound of Formula Q is outlined in the Scheme 32 below.

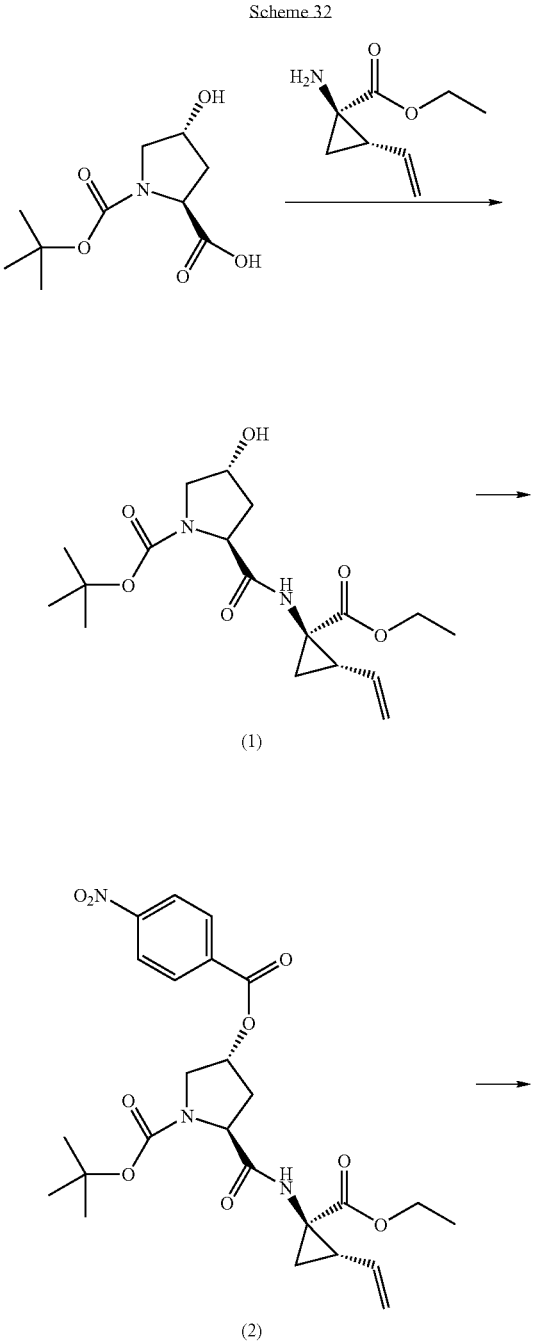

In Scheme 31, a compound of Formula K is reacted with a chlorooquinazoline L in presence of a base, such as NaH or tBuOK, to form a compound of Formula M. The resulting acid M can be treated with 1-(amino)-2-(vinyl)cyclopropanecarboxylic acid ethyl ester in the presence of peptide coupling agent, such as HATU or EDCI/HOAt and in presence of a base, such as DIPEA, to give a product of Formula N. The deprotection of the Boc moiety of the compound of Formula N can be realized by treatment with an acid, such as TFA, in a solvent such as methylene chloride to provide the free amine of Formula O, Subsequently, the urea of Formula P can be prepared from the compound of Formula O by treatment with phosgene, or an equivalent of phosgene, and an amine of Formula B, in presence of a base, such as $NaHCO_3$. The resulting diolefin P can be submitted to ring closure using an olefin metathesis catalyst, such as the Hoveyda-Grubbs catalysts or Bis(tricyclohexylphosphine)[(phenylthio)-methylene]ruthenium (IV) dichloride, Bis(tricyclohexylphosphine)-3-phenyl-1H-inden-1-ylideneruthenium (IV) dichloride

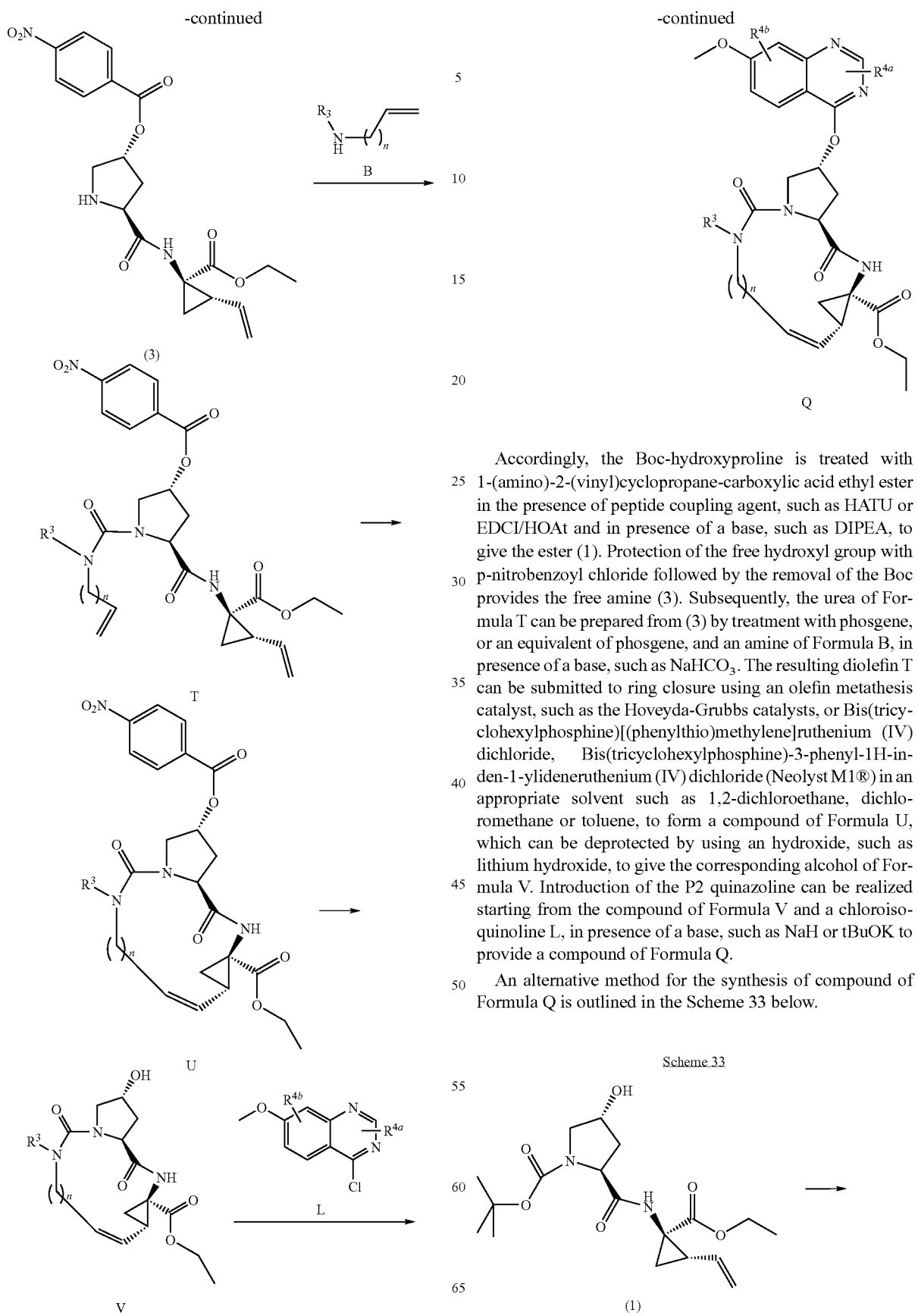

Accordingly, the Boc-hydroxyproline is treated with 1-(amino)-2-(vinyl)cyclopropane-carboxylic acid ethyl ester in the presence of peptide coupling agent, such as HATU or EDCl/HOAt and in presence of a base, such as DIPEA, to give the ester (1). Protection of the free hydroxyl group with p-nitrobenzoyl chloride followed by the removal of the Boc provides the free amine (3). Subsequently, the urea of Formula T can be prepared from (3) by treatment with phosgene, or an equivalent of phosgene, and an amine of Formula B, in presence of a base, such as $NaHCO_3$. The resulting diolefin T can be submitted to ring closure using an olefin metathesis catalyst, such as the Hoveyda-Grubbs catalysts, or Bis(tricyclohexylphosphine)[(phenylthio)methylene]ruthenium (IV) dichloride, Bis(tricyclohexylphosphine)-3-phenyl-1H-inden-1-ylideneruthenium (IV) dichloride (Neolyst M1®) in an appropriate solvent such as 1,2-dichloroethane, dichloromethane or toluene, to form a compound of Formula U, which can be deprotected by using an hydroxide, such as lithium hydroxide, to give the corresponding alcohol of Formula V. Introduction of the P2 quinazoline can be realized starting from the compound of Formula V and a chloroisoquinoline L, in presence of a base, such as NaH or tBuOK to provide a compound of Formula Q.

An alternative method for the synthesis of compound of Formula Q is outlined in the Scheme 33 below.

-continued

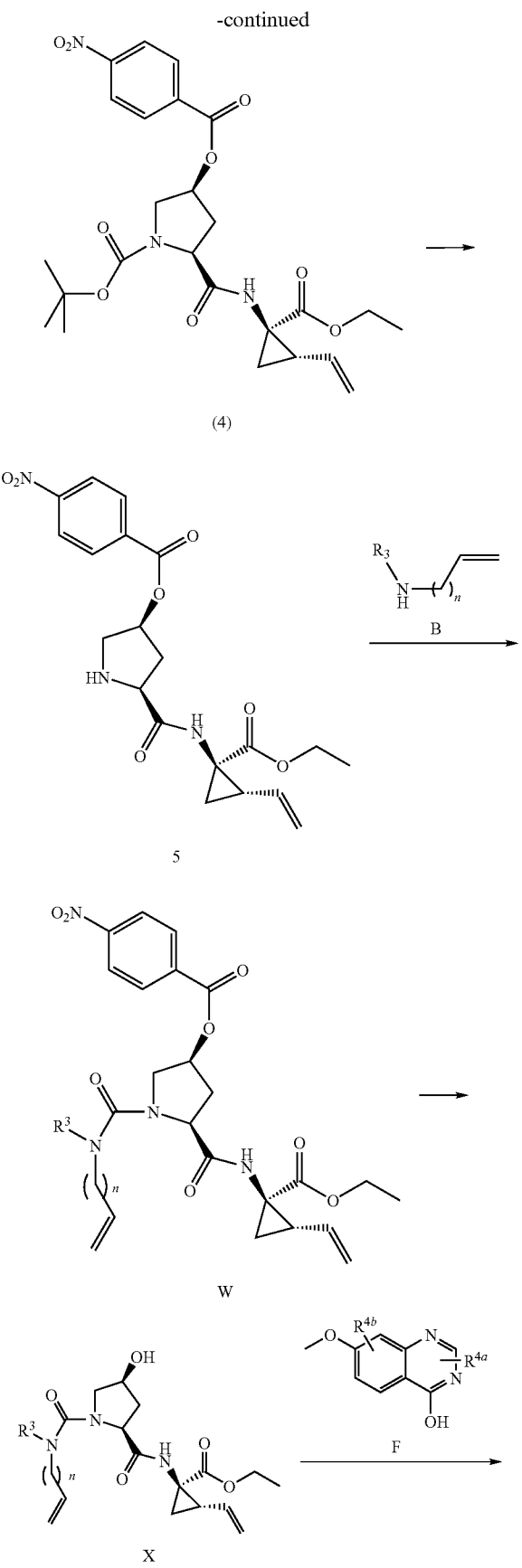

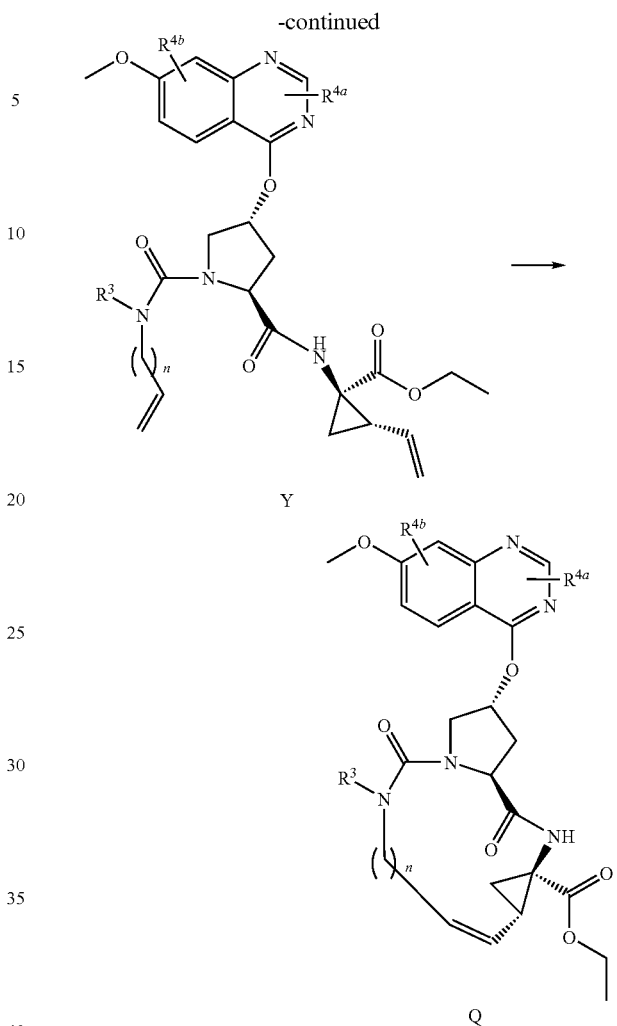

Accordingly, the proline derivative (1) is protected with p-nitrobenzoic acid followed by the removal of the Boc to give free amine (5). Subsequently, the urea of Formula W can be prepared from (5) by treatment with phosgene, or an equivalent of phosgene, and an amine of Formula B, in presence of a base, such as NaHCO$_3$. The compound of Formula W can be deprotected by using an hydroxide, such as lithium hydroxide, to give the corresponding alcohol of Formula X. Introduction of the P2 isoquinoline can be realized starting from the compound of Formula X and a hydroxyisoquinoline F, using a Mitsunobu reaction, to provide a compound of Formula Y. The resulting diolefin Y can be submitted to ring closure using an olefin metathesis catalyst, such as the Hoveyda-Grubbs catalyst or the like, in an appropriate solvent such as 1,2-dichloroethane, dichloromethane or toluene, to form a compound of Formula Q.

In the above schemes 28-33 (only) $R^3$ corresponds to the present NRyRy', X corresponds to L, $R^{4a}$ corresponds to $R^9$, $R^{4b}$ and $R^{4b'}$ correspond to other R8 substituents, $R^5$ corresponds to $R^1$ and $R^6$ corresponds to $R^3$, as defined above for the compounds of formula (I) or of any of the subgroups thereof. Although schemes 28-33 are illustrated with a compound comprising a quinazolyl ether as W—R8 it will be readily apparent that the corresponding methodology is applicable to other —W—R8 values.

The reactions of the schemes above may be conducted in a suitable solvent in the presence of a base such as an alkali metal carbonate or hydroxide, e.g. sodium, potassium or cesium carbonate; or an organic base such as a trialkylamine, e.g. triethylamine. Suitable solvents for this reaction are for example ethers, e.g. THF, dioxane; halogenated hydrocarbons, e.g. dichloromethane, $CHCl_3$, toluene, polar aprotic solvents such as DMF, DMSO, DMA and the like.

Compounds of formula (I) may be converted into each other following art-known functional group transformation reactions, comprising those described hereinafter.

A number of the intermediates used to prepare the compounds of formula (I) are known compounds or are analogs of known compounds, which can be prepared following modifications of art-known methodologies readily accessible to the skilled person. A number of preparations of intermediates are given hereafter in somewhat more detail.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) may be obtained as racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound may be synthesized by stereospecific methods of preparation. These methods may advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylactically act against, to stabilize or to reduce viral infection, and in particular HCV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections and their associated diseases treatable using the compounds and methods of the present invention include those infections brought on by HCV and other pathogenic flaviviruses such as Yellow fever, Dengue fever (types 1-4), St. Louis encephalitis, Japanese encephalitis, Murray valley encephalitis, West Nile virus and Kunjin virus. The diseases associated with HCV include progressive liver fibrosis, inflammation and necrosis leading to cirrhosis, end-stage liver disease, and HCC; and for the other pathogenic flaviviruses the diseases include yellow fever, dengue fever, hemorraghic fever and encephalitis. A number of the compounds of this invention moreover are active against mutated strains of HCV. Additionally, many of the compounds of this invention show a favorable pharmacokinetic profile and have attractive properties in terms of bioavailability, including an acceptable half-life, AUC (area under the curve) and peak values and lacking unfavourable phenomena such as insufficient quick onset and tissue retention.

The in vitro antiviral activity against HCV of the compounds of formula (I) was tested in a cellular HCV replicon system based on Lohmann et al. (1999) Science 285:110-113, with the further modifications described by Krieger et al. (2001) Journal of Virology 75: 4614-4624 (incorporated herein by reference), which is further exemplified in the examples section. This model, while not a complete infection model for HCV, is widely accepted as the most robust and efficient model of autonomous HCV RNA replication currently available. Compounds exhibiting anti-HCV activity in this cellular model are considered as candidates for further development in the treatment of HCV infections in mammals. It will be appreciated that it is important to distinguish between compounds that specifically interfere with HCV functions from those that exert cytotoxic or cytostatic effects in the HCV replicon model, and as a consequence cause a decrease in HCV RNA or linked reporter enzyme concentration. Assays are known in the field for the evaluation of cellular cytotoxicity based for example on the activity of mitochondrial enzymes using fluorogenic redox dyes such as resazurin. Furthermore, cellular counter screens exist for the evaluation of non-selective inhibition of linked reporter gene activity, such as firefly luciferase. Appropriate cell types can be equipped by stable transfection with a luciferase reporter gene whose expression is dependent on a constitutively active gene promoter, and such cells can be used as a counter-screen to eliminate non-selective inhibitors.

Due to their antiviral properties, particularly their anti-HCV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a HCV infection, and for the prophylaxis of these infections. In general, the compounds of the present invention may be useful in the treatment of warm-blooded animals infected with viruses, in particular flaviviruses such as HCV.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the HCV infection.

The present invention also relates to the use of the present compounds or any subgroup thereof in the manufacture of a medicament for the treatment or the prevention of viral infections, particularly HCV infection.

The present invention furthermore relates to a method of treating a warm-blooded animal infected by a virus, or being at risk of infection by a virus, in particular by HCV, said method comprising the administration of an anti-virally effective amount of a compound of formula (I), as specified herein, or of a compound of any of the subgroups of compounds of formula (I), as specified herein.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of previously known anti-HCV compound, such as, for instance, interferon-$\alpha$ (IFN-$\alpha$), pegylated interferon-$\alpha$ and/or ribavirin, and a compound of formula (I) can be used as a medicine in a combination therapy. The term "combination therapy" relates to a product containing mandatory (a) a compound of formula (I), and (b) optionally another anti-HCV compound, as a combined preparation for simultaneous, separate or sequential use in treatment of HCV infections, in particular, in the treatment of infections with HCV. Thus, to combat or treat HCV infections, the compounds of formula (I) may be co-administered in combination with for instance, interferon-$\alpha$ (IFN-$\alpha$), pegylated interferon-$\alpha$ and/or ribavirin, as well as therapeutics based on antibodies targeted against HCV epitopes, small interfering RNA (Si RNA), ribozymes, DNAzymes, antisense RNA, small molecule antagonists of for instance NS3 protease, NS3 helicase and NS5B polymerase.

Accordingly, the present invention relates to the use of a compound of formula (I) or any subgroup thereof as defined above for the manufacture of a medicament useful for inhibiting HCV activity in a mammal infected with HCV viruses, wherein said medicament is used in a combination therapy, said combination therapy preferably comprising a compound of formula (I) and (pegylated) IFN-$\alpha$ and/or ribavirin, and optionally an anti-HIV compound. For example in drugs prone to rapid metabolism by Cyp3A4, co-dosing with the HIV protease inhibitors such as ritonavir can allow lower dosage regimes to be administered.

DETAILED DESCRIPTION OF THE EMBODIMENTS

Various embodiments of the invention will now be described by way of illustration only with reference to the following non-limiting examples.

EXAMPLE 1

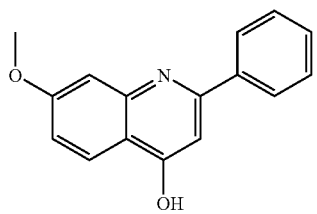

7-Methoxy-2-phenyl-quinolin-4-ol (1)

To a stirred round bottled flask with toluene (100 mL) ethyl benzoyl acetate (18.7 g, 97 mmol) and m-anisidine (12 g, 97 mmol) was added. 4 M HCl in dioxane (0.5 mL) was added and the reaction mixture was refluxed for 6 h (140° C.). The mixture was co-evaporated with toluene. To the crude mixture diphenyl ether (50 mL) was added and the mixture was heated to 280° C. for 2 h. When the theoretical amount ethanol (6 mL) was collected in a Dean Stark trap the heating was stopped and the mixture was cooled to rt. The crude mixture was dissolved in $CH_2Cl_2$ (100 mL) and stirred for 30 min. The formed precipitate was filtered off and dried which gave 1 (4.12 g, 16.4 mmol, 17%): pale yellow powder.

$^1$H (300 MHz, DMSO-$D_6$): δ 3.8 (s, 3H), 6.24 (s, 1H), 6.88-6.96 (dd, 1H, J=9.07 Hz, J=2.47 Hz), 7.19 (d, 1H, J=2.19 Hz), 7.56 (t, 3H, J=2.19 Hz), 7.8 (dd, 2H, J=7.14 Hz, J=2.19 Hz), 8.0 (d, 1H, J=9.06 Hz); $^{13}$C (75.5 MHz, DMSO-$D_6$): δ 55.3, 99.6, 106.9, 113.1, 119.1, 126.4, 127.5, 128.8, 130.2, 134.1, 142.2, 149.4, 161.8, 176.4.

EXAMPLE 2

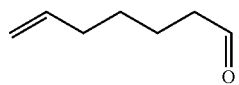

Hept-6-enal (2)

To a solution of hept-6-en-1-ol (1 mL, 7.44 mmol) and N-methylmorpholine N-oxide (1.308 g, 11.17 mmol) in DCM (17 mL) was added ground molecular sieves (3.5 g, 4 Å). The mixture was stirred for 10 min at room temperature under nitrogen atmosphere before tetrapropylammonium perruthenate (TPAP) (131 mg, 0.37 mmol) was added. After stirring for additional 2.5 h the solution was filtered through celite. The solvent was then carefully evaporated and the remaining liquid was purified by flash column chromatography (DCM) to give the volatile aldehyde (620 mg, 74%) as an oil.

EXAMPLE 3

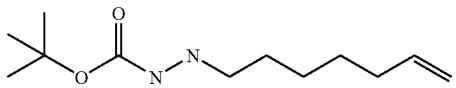

N'-Hept-6-en-(E)-ylidene-hydrazinecarboxylic acid tert-butyl ester (3)

To a solution of compound 2 (68 mg, 0.610 mmol) and tert-butyl carbazate (81 mg, 0.613 mmol) in MeOH (5 mL) was added ground molecular sieves (115 mg, 3 Å). The mixture was stirred for 3 h after which it was filtered through celite and evaporated. The residue was dissolved in dry THF (3 mL) and AcOH (3 mL). $NaBH_3CN$ (95 mg, 1.51 mmol) was added and the solution was stirred over night. The reaction mixture was diluted with saturated $NaHCO_3$ solution (6 mL) and EtOAc (6 mL). The organic phase was washed with brine, saturated $NaHCO_3$, brine, dried over $MgSO_4$ and evaporated. The cyanoborane adduct was hydrolyzed by treatment with MeOH (3 mL) and 2 M NaOH (1.9 mL). The mixture was stirred for 2 h and the MeOH was evaporated. $H_2O$ (5 mL) and DCM (5 mL) were added and the water phase was extracted three times with DCM. The combined organic phases were dried and evaporated. Purification by flash column chromatography (toluene/ethyl acetate 9:1 with 1% triethylamine and toluene/ethyl acetate 6:1 with 1% triethylamine) provided the title compound (85 mg, 61%) as an oil.

EXAMPLE 4

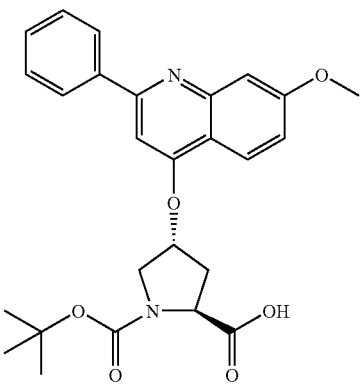

N-Boc-4R-(2-phenyl-7-methoxyquinoline-4-oxo) proline (4)

To a stirred solution of N-Boc-trans-4-hydroxy-L-proline (3.9 g, 16.9 mmol) in DMSO (90 mL) was added potassium tert.butoxide (4.5 g, 40.1 mmol). After 1 hrs 4-chloro-2-phenyl-7-methoxy quinoline (4.5 g, 16.7 mmol) was added and stirred at RT for 12 hrs. The mixture was diluted with water (180 mL), washed with ethyl acetate (1×30 mL) and neutralized with 1N HCl. The solid was filtered, washed with water and dried which gave the title product (4.65 g, 10 mmol)> 95% purity by HPLC. M+H+ 464.2.

EXAMPLE 5

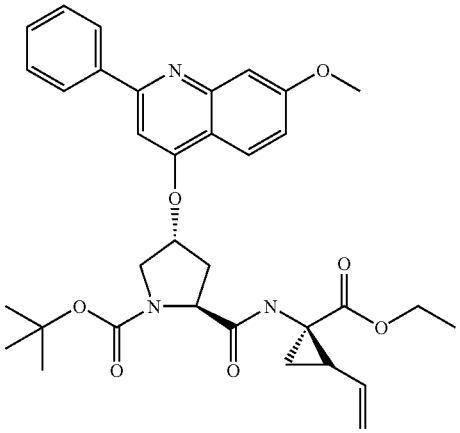

2-(1-Ethoxycarbonyl-2-vinyl-cyclopropylcarbamoyl)-4-(7-methoxy-2-phenyl-quinoline-4-yloxy)-pyrrolidine-1-carboxylic acid tert.butyl ester (5)

To a solution of 1-amino-2-vinyl-cyclopropanecarboxylic acid ethyl ester (41 mg, 0.26 mmol), compound 4 (11 mg, 0.22 mmol), HATU (204 mg, 0.54 mmol) in DMF (4 mL) was added diisopropyethylamine (187 µL, 1.08 mmol). After stirring at RT for 1 hrs, dichloromethane (4 mL) was added. The solution was washed with aqueous NaHCO₃ (sat) and with two portions of water. The organic layer was dried and concentrated. The product was pure enough (>95% by HPLC) to be used in the next step. M+H+ 602.2.

EXAMPLE 6

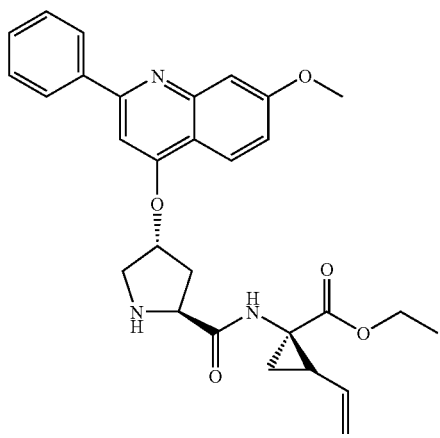

1-{[4-(7-Methoxy-2-phenyl-quinolin-4-yloxy)-pyrrolidine-2-carbonyl]-amino}-2-vinyl-cyclopropanecarboxylic acid ethyl ester (6)

Compound 5 was kept in TFA-DCM 1:2 (3 mL) at RT for 60 min. Toluene (3 mL) was added. The sample was co-evaporated to dryness. Purity by HPLC >95%. M+H+ 502.4.

EXAMPLE 7

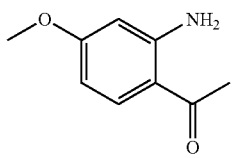

1-(2-Amino-4-methoxyphenyl)ethanone (7)

m-Anisidine (10.0 g, 82 mmol) was dissolved in CH₂Cl₂ (50 mL), and the solution was cooled to −50° C. BCl₃ (1 M in CH₂Cl₂, 82 mL, 82 mmol) was added slowly during 20 min, after which the mixture was stirred at −50° C. for 30 min, followed by sequential addition of AcCl (6.0 mL, 84 mmol) and AlCl₃ (11 g, 82 mmol). The mixture was stirred at −50° C. for 1 h and was then allowed to assume rt. After stirring at rt overnight, the solution was heated at 40° C. for 4 h, after which the mixture was poured over ice. The aqueous mixture was made alkaline with 10% NaOH (w/v) and extracted with EtOAc (4×200 mL). The combined organic phases were washed with brine, dried (MgSO₄), and evaporated to give a black solid, which was purified by flash column chromatography (ether/CH₂Cl₂ 20:80). The resulting solid was recrystallized from ether/hexane to give the title compound as shiny tan leaflets (5.6 g, 42%).

EXAMPLE 8

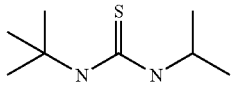

N-(tert-Butyl)-N'-isopropylthiourea (8)

To a solution of tert-butylisothiocyanate (5.0 mL, 39 mmol) in CH₂Cl₂ (200 mL) were added isopropylamine (4.0 mL, 47 mmol) and diisopropylethylamine (DIEA) (6.8 mL, 39 mmol), and the mixture was stirred at rt for 2 h. The reaction mixture was diluted with EtOAc, washed with 10% citric acid (2×), saturated NaHCO₃ (2×), H₂O (2×), and brine (1×). The organic layer was dried (MgSO₄) and evaporated to yield compound 94 (3.3 g, 52%) as a white solid which was used without further purification.

EXAMPLE 9

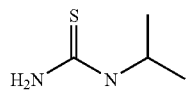

N-Isopropylthiourea (9)

Compound 8 (3.3 g, 20 mmol) was dissolved in conc. HCl (45 mL) and the solution was refluxed for 40 min. The mixture was allowed to cool to rt and then cooled in an ice bath and basified to pH 9.5 with solid and saturated NaHCO$_3$, after which the product was extracted into EtOAc (3×). The combined organic phases were washed with H$_2$O (2×) and brine (1×), dried (MgSO$_4$), and evaporated to yield crude title compound (2.1 g, 90%) which was used without further purification.

EXAMPLE 10

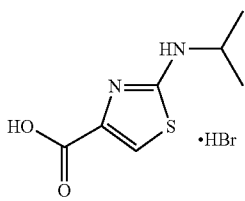

2-(Isopropylamino)-1,3-thiazole-4-carboxylic acid hydrobromide (10)

A suspension of compound 9 (2.1 g, 18 mmol) and 3-bromopyruvic acid (3.0 g, 18 mmol) in dioxane (180 mL) was heated to 80° C. Upon reaching 80° C. the mixture became clear, and soon thereafter the product started to precipitate as a white solid. After 2 h of heating, the reaction mixture was cooled to rt and the precipitate was filtered off and collected. This yielded pure title compound (4.4 g, 94%).

EXAMPLE 11

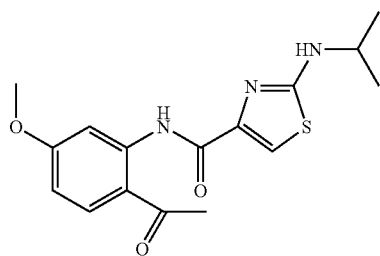

N-(2-Acetyl-5-methoxyphenyl)-2-(isopropylamino)-1,3-thiazole-4-carboxamide (11)

A mixture of compound 10 (4.4 g, 16.5 mmol) and the aniline derivative 7 (2.75 g, 16.5 mmol) in pyridine (140 mL) was cooled to −30° C. (upon cooling, the clear solution became partially a suspension). POCl$_3$ (3.3 mL, 35 mmol) was added slowly over a 5 min period. The mixture was stirred at −30° C. for 1 h, and was then allowed to assume rt. After stirring at rt for 1.5 h the reaction mixture was poured over ice, and the pH was adjusted to about 9-10 using solid and saturated NaHCO$_3$. The crude product was extracted into CH$_2$Cl$_2$ (3×) and the combined organic phases were dried (MgSO$_4$) and evaporated. The crude dark-beige solid was purified by flash column chromatography (hexane/EtOAc 55:45) to give compound 47 (5.6 g, 76%) as a pale yellow solid.

EXAMPLE 12

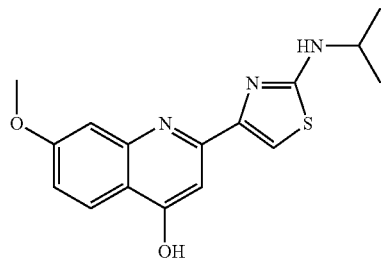

2-[2-(Isopropylamino)-1,3-thiazol-4-yl]-7-methoxyquinolin-4-ol (12)

A solution of t-BuOK (2.42 g, 21 mmol) in anhydrous t-BuOH (40 mL) was heated to reflux. Compound 11 (1.8 g, 5.4 mmol) was added portion-wise over a 5 min period, and the dark red solution formed was stirred at reflux for an additional 20 min. The mixture was cooled to rt, and HCl (4 M in dioxane, 8.0 mL, 32 mmol) was added, after which the reaction mixture was concentrated under vacuum. In order to assure that all of the HCl and dioxane were removed, the crude product was re-dissolved in CH$_2$Cl$_2$ twice and thoroughly evaporated to obtain the slightly impure HCl salt of compound 98 (1.62 g) as a brown solid. The product was dissolved in CH$_2$Cl$_2$ and washed with saturated NaHCO$_3$, after which the aqueous phase was extracted several times with CH$_2$Cl$_2$. The combined organic phases were dried (MgSO$_4$) and evaporated which gave the title compound (1.38 g, 81%) as a light brown solid (>95% pure according to HPLC tests).

$^1$H-NMR (MeOH-d$_4$, 400 MHz): δ 1.30 (d, J=6.0 Hz, 6H), 3.93 (s, 3H), 3.95-4.07 (m, 1H), 6.73 (s, 1H), 6.99 (dd, J=2.4, 9.2 Hz, 1H), 7.26 (d, J=2.4 Hz, 1H), 7.37 (s, 1H), 8.10 (d, J=9.2 Hz, 1H).

EXAMPLE 13

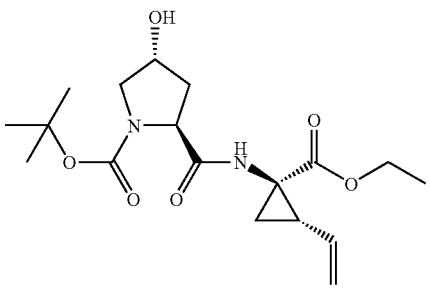

(2S,4R)-2-((1S,2R)1-Ethoxycarbonyl-2-vinyl-cyclopropylcarbamoyl)-4-hydroxy-pyrrolidine-1-carboxylic acid tert-butyl ester (13)

A solution of HATU (6 g), diisopropylethylamine (6.8 mL), (1R,2S)-1-amino-2-vinyl-cyclopropanecarboxylic acid ethyl ester (1.5 g) and BOC-L-hydroxyproline (1.6 g) in dichloromethane was stirred for 1 hrs. The mixture was extracted with DCM-NaHCO₃ (aq) dried and concentrated. HPLC purity ca 90% M+H⁺ 369.1.

EXAMPLE 14

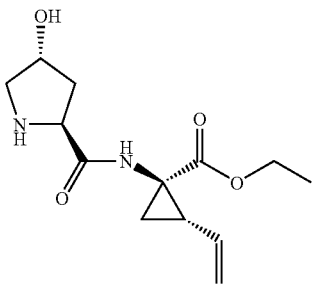

(1S,2R)-1-[(2S,4R)-(4-Hydroxy-pyrrolidine-2-carbonyl)-amino]-2-vinyl-cyclopropanecarboxylic acid ethyl ester (14)

Compound 13 was kept in 30% trifluoroacetic acid in dichloromethane and 1% MeOH for 2 hrs before it was concentrated to dryness. The residue was re-dissolved in dichloromethane and during stirring 1N NaOH was added to pH 10-11. The organic layer was separated and concentrated which gave 1.6 g of the title product. HPLC purity ca. 90% M+H⁺ 269.1.

EXAMPLE 15

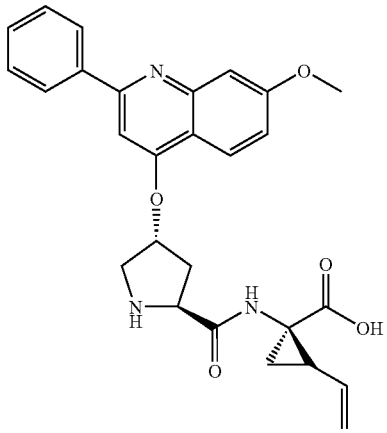

(1R,2S)-1-{[(2S,4R)-4-(7-Methoxy-2-phenyl-quinolin-4-yloxy)-pyrrolidine-2-carbonyl]-amino}-2-vinyl-cyclopropanecarboxylic acid (15)

To a solution of compound 6 (0.067 mmol) in THF-MeOH 2:3 (2 ml) was added 1M LiOH 10 equiv. The solution was kept at 50° C. for 2.5 hrs. After cooling to RT, HOAc 20 eq. was added followed by toluene (2 ml) and then concentrated to dryness. The residue was taken up in DCM and filtered form the salts which gave the title compound (0.07 mmol). Purity >95% by HPLC M+H⁺ 474.

EXAMPLE 16

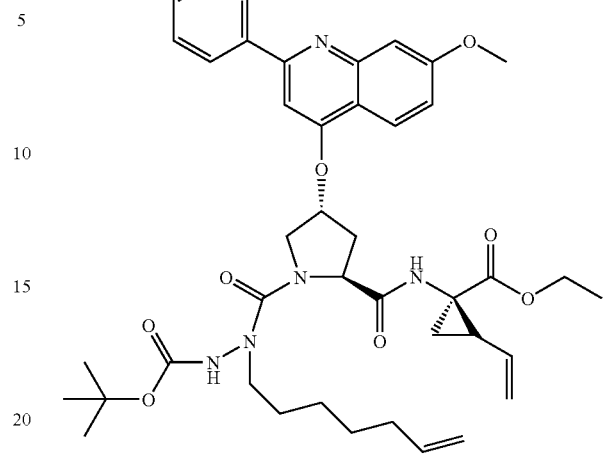

1-{[1-(N'-tert-Butoxycarbonyl-N-hept-6-enyl-hydrazinocarbonyl)-4-(7-methoxy-2-phenyl-quinolin-4-yloxy)-pyrrolidine-2-carbonyl]-amino}-2-vinyl-cyclopropanecarboxylic acid ethyl ester (16)

Compound 15 (200 mg, 0.4 mmol) was dissolved in tetrahydrofuran (10 ml). A tea-spoon of sodium hydrogencarbonate was added, followed by phosgene (1.8 μl, 1.9 M in toluene). The reaction mixture was stirred for 30 min and filtrated. The solvent was evaporated and the crude chloride was re-dissolved in dichloromethane (10 ml). Sodium hydrogencarbonate (1 tea-spoon) and N'-hept-6-enyl-hydrazinecarboxylic acid tert-butyl ester (182 mg, 0.8 mmol). The reaction mixture was stirred at room temp. for 40 h. and then filtrated and purified by silica chromatography (1%→2% methanol in ether) to give pure title product (240 mg, 79%).

EXAMPLE 17

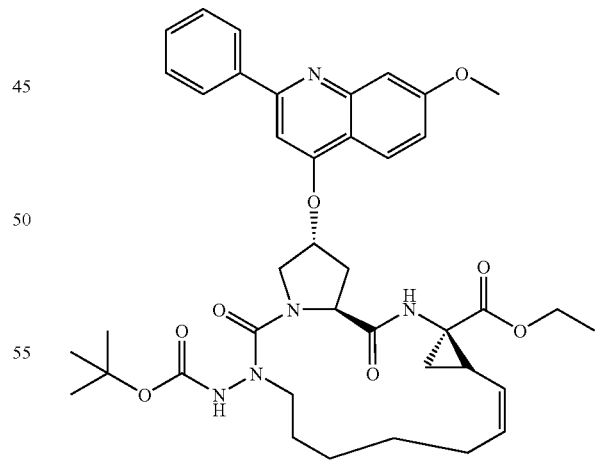

14-tert-Butoxycarbonylamino-18-(7-methoxy-2-phenyl-quinolin-4-yloxy)-2,15-dioxo-3,14,16-triaza-tricyclo[14.3.0.0*4,6*]nonadec-7-ene-4-carboxylic acid ethyl ester (17)

Compound 16 (200 mg, 0.26 mmol) was dissolved in degassed dichloromethane (30 ml). Hoveyda-Grubbs catalyst II generation (16 mg, 0.026 mmol) was then added and the mixture was refluxed under argon atmosphere overnight. The solvent was then evaporated and the crude product was purified by silica chromatography (1% methanol in ether) which gave the title compound (39 mg, 20%). MS (M+H$^+$) 728.2.

EXAMPLE 18

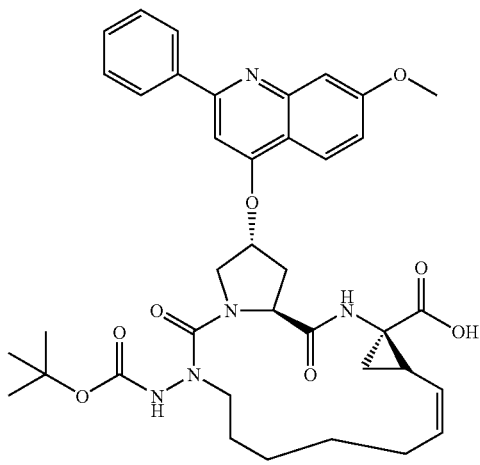

14-tert-Butoxycarbonylamino-18-(7-methoxy-2-phenyl-quinolin-4-yloxy)-2,15-dioxo-3,14,16-triaza-tricyclo[14.3.0.0*4,6*]nonadec-7-ene-4-carboxylic acid (18)

Compound 17 (39 mg, 0.054 mmol) was dissolved in tetrahydrofuran (3.5 ml), water (1.75 ml) and methanol (1.75 ml). Lithium hydroxide (430 µl, 1 M in water) was then added and the reaction was stirred at room temperature for 24 h. The volume was reduced to half and water (10 ml) was added. Acidification (pH=5) followed by extraction with chloroform gave the pure title compound (34 mg, 90%). MS (M+H$^+$) 700.2

EXAMPLE 19

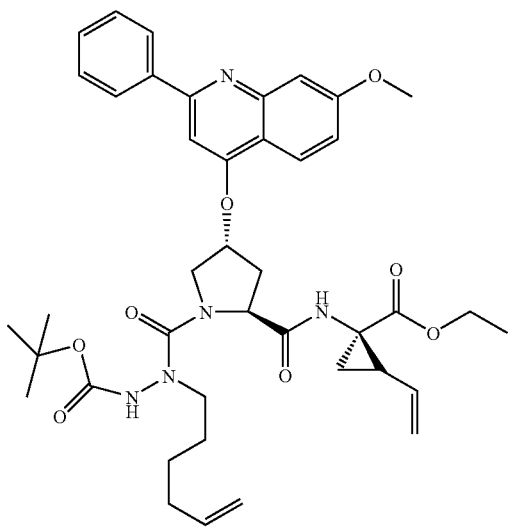

1-{[1-(N'-tert-Butoxycarbonyl-N-hex-5-enyl-hydrazinocarbonyl)-4-(7-methoxy-2-phenyl-quinolin-4-yloxy)-pyrrolidine-2-carbonyl]-amino}-2-vinyl-cyclopropanecarboxylic acid ethyl ester (19)

The title compound was prepared from compound 15 (800 mg, 1.6 mmol) and N'-hex-5-enyl-hydrazinecarboxylic acid tert-butyl ester (620 mg, 2.9 mmol) according to the procedure described in Example 16 which gave the title compound (1 g, 85%). MS (M+H$^+$) 742.37

EXAMPLE 20

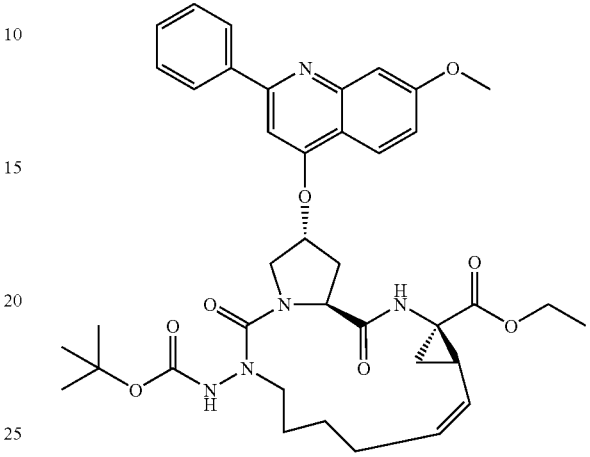

13-tert-Butoxycarbonylamino-17-(7-methoxy-2-phenyl-quinolin-4-yloxy)-2,14-dioxo-3,13,15-triaza-tricyclo[13.3.0.0*4,6*]octadec-7-ene-4-carboxylic acid ethyl ester (20)

Treatment of compound 19 (400 mg, 0.54 mmol) according to the procedure described in example 17 gave a crude product. Purification by silica gel chromatography (1% methanol in ether) gave the title compound (67 mg, 17%). MS (M+H$^+$) 714.29.

EXAMPLE 21

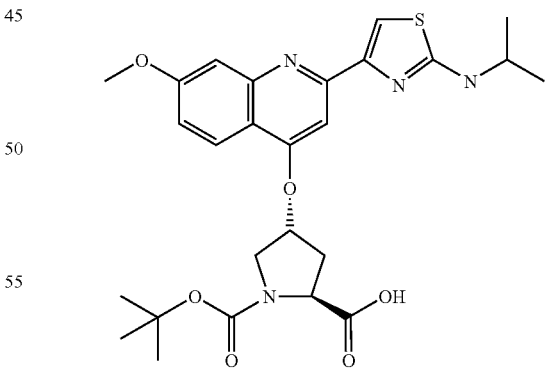

4-[2-(2-Isopropylamino-thiazol-4-yl)-7-methoxy-quinolin-4-yloxy]-pyrrolidine-1,2-dicarboxylic acid 1-tert-butyl ester (21)

To a stirred solution of N-Boc-trans-4-hydroxy-L-proline (221 mg, 0.96 mmol) in DMSO was added potassiumtertbutoxide (320 mg, 2.9 mmol). After 1 h compound 12 (319 mg, 0.96 mmol) was added and the mixture was stirred at 70° C. for 72 hours. The mixture was diluted with water and extracted with ethyl acetate. The product was used without further purification. Yield 429 mg, 85%.

EXAMPLE 22

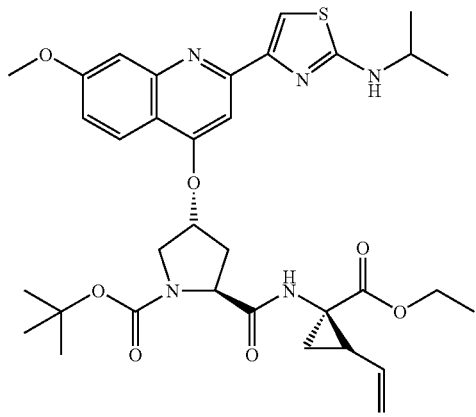

2-(1-Ethoxycarbonyl-2-vinyl-cyclopropylcarbamoyl)-4-[2-(2-isopropylamino-thiazol-4-yl)-7-methoxy-quinolin-4-yloxy]-pyrrolidine-1-carboxylic acid tert-butyl ester (22)

Compound 21 (300 mg, 0.56 mmol) was reacted with 1-amino-2-vinyl-cyclopropanecarboxylic acid ethyl ester (130 mg, 0.84 mmol) as described in Example 5 which gave the title compound (302 mg, 80%).

EXAMPLE 23

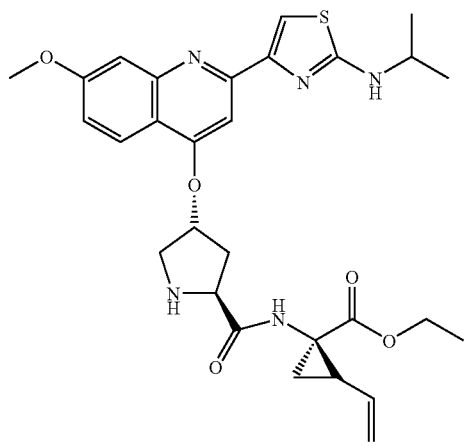

1-({4-[2-(2-Isopropylamino-thiazol-4-yl)-7-methoxy-quinolin-4-yloxy]-pyrrolidine-2-carbonyl}-amino)-2-vinyl-cyclopropanecarboxylic acid ethyl ester (23)

Compound 22 (302 mg, 0.45 mmol) was treated as described in Example 6 which gave the title compound (195 mg, 76%).

EXAMPLE 24

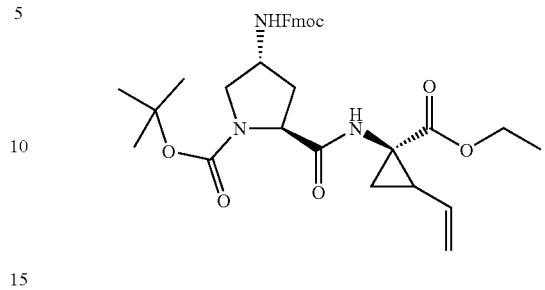

Fmoc-4-amino-2-(1-ethoxycarbonyl-2-vinyl-cyclopropylcarbamoyl)-pyrrolidine-1-carbocyclic acid tert-butyl ester (24)

(2S,4R) Fmoc-4-amino-1-Boc-pyrrolidine-2-carboxylic acid (5.3 g, 11.8 mmol) was dissolved in DCM (100 ml), HATU (4.94 g, 12.99 mmol), DIEA (4.63 ml, 26.57 mmol) and vinylcyclopropylglycine ethyl ester (2.26 g, 11.81 mmol) were added successively. The mixture was stirred for 16 h at room temperature, and was then diluted with DCM (50 ml), washed with citric acid (10% aq), water, NaHCO$_3$ (sat.aq) and water. The organic phase was dried over Na$_2$SO$_4$ and concentrated to afford a beige solid foam (8.11 g) which was subjected to silica gel column chromatography to afford the title compound (7.14 g, 12.11 mmol).

EXAMPLE 25

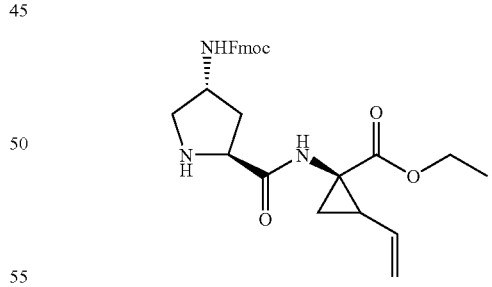

1-[(Fmoc-4-amino-pyrrolidine-2-carbonyl)-amino]-2-vinyl-cyclopropanecarboxylic acid ethyl ester (25)

Compound 24 (3.65 g, 6.04 mmol) was treated with a solution of TFA/DCM (10 ml TFA, 50 ml DCM) for 2.5 h and then concentrated to afford the titled compound (2.99 g, 6.12 mmol).

EXAMPLE 26

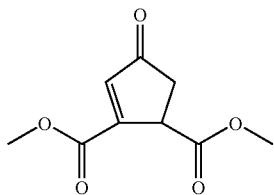

(Rac)-4-oxocyclopent-2-ene-1,2-dicarboxylic acid dimethyl ester (26)

(1R,2S)-4-oxo-cyclopentane-1,2-dicarboxylic acid dimethyl ester (4.8 g, 23.8 mmol) and CuBr$_2$ (11.9 g, 53.2 mmol) were dissolved in dry THF (70 mL) and the mixture was refluxed for two hours at 90° C. The formed CuBr was filtrated off and the organic phase was concentrated. CaCO$_3$ (2.7 g, 27.2 mmol) and DMF (70 mL) were added and the mixture was held at 100° C. for one hour. The dark brown mixture was poured over ice (35 g) and the formed precipitate was filtrated off. The aqueous layer was extracted with ethyl acetate (1×300 mL+3×150 mL). The organic phases were dried, filtrated and concentrated. Purification by flash chromatography (toluene/EtOAc 9:1) gave 2 (2.1 g, 45%) as yellow crystals

EXAMPLE 27

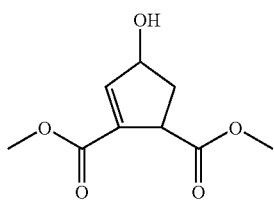

((1S,4R) & (1R,4S))-4-hydroxy-cyclopent-2-ene-1,2-dicarboxylic acid dimethyl ester (27)

To a cold solution (−30° C.) of compound 26 (3.18 g, 16.1 mmol) dissolved in MeOH (23 mL), NaBH$_4$ (0.66 g, 17.5 mmol) was added. After nine minutes the excess of NaBH$_4$ was destroyed by adding brine (80 mL). The mixture was concentrated and extracted with ethyl acetate (4×80 mL). The organic phases were dried, filtrated and concentrated and gave the title compound (3.0 g, 92%) as a yellow oil.

EXAMPLE 28

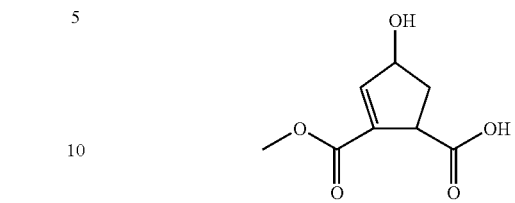

(1S,4R) & (1R,4S)-4-hydroxy-cyclopent-2-ene-1,2-dicarboxylic acid 2-methyl ester (28)

To an ice-cold solution of compound 27 (3.4 g, 22 mmol) dissolved in dioxane and water (1:1, 110 mL), LiOH (0.52 g, 22 mmol) was added. After two and a half hours the mixture was co-evaporated with toluene and methanol. Purification by flash chromatography (toluene/Ethyl acetate 3:1+1% HOAc) gave the title compound (1.0 g, 27%) as yellow-white crystals.

$^1$H-NMR (300 MHz, CD$_3$OD): δ 1.78-1.89 (m, 1H), 2.70-2.84 (m, 1H), 3.56-3.71 (m, 1H), 3.76 (s, 3H), 4.81-4.90 (m, 1H), 6.76-6.81 (m, 1H); $^{13}$C-NMR (75.5 MHz, CDCl$_3$): δ 38.0, 48.0, 52.4, 75.7, 137.0, 146.2, 165.0 178.4.

EXAMPLE 29

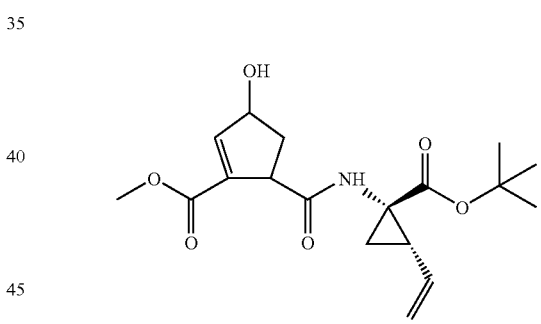

((3S,5R) & (3R,5S))-5-((1R,2S)-1-tert-Butoxycarbonyl-2-vinyl-cyclopropylcarbamoyl)-3-hydroxy-cyclopent-1-enecarboxylic acid methyl ester (29)

To an ice cooled solution of 28 (50 mg, 37 mmol) and (1R,2S)-1-amino-2-vinyl-cyclopropane carboxylic acid tert-butyl ester in DMF (5 mL), DIPEA (47 mmol) and HATU (47 mmol) were added. After two hours the solution was concentrated and purified using column chromatography (toluene/ethyl acetate 3:1). This gave the title compound as a slightly yellow oil (50 mg, 38%).

$^1$H-NMR (300 MHz, CDCl$_3$): δ [(1.38 & 1.42) s, 9H], 1.75-1.83 (m, 1H), 2.00-2.21 (m, 3H), 3.55-3.63 (m, 1H), [(3.77 & 3.82) s, 3H], 4.20-4.38 (m, 1H), 4.65-4.80 (m, 1H), 5.13-5.20 (m, 1H), 5.22-5.38 (m, 1H), 5.60-5.82 (m, 1H), 6.95-6.96 (m, 2H).

EXAMPLE 30

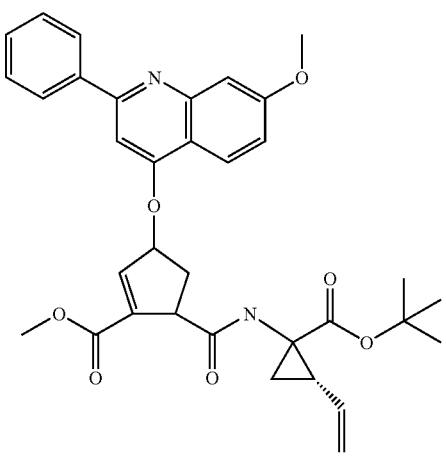

((3R,5R) & (3S,5S))-5-((1R,2S)-1-tert-Butoxycarbonyl-2-vinyl-cyclopropylcarbamoyl)-3-(7-methoxy-2-phenyl-quinolin-4-yloxy)-cyclopent-1-enecarboxylic acid methyl ester (30)

To an ice cooled solution of 29 (41 mg, 116 mmol) in dry THF, 7-methoxy-2-phenyl-quinolin-4-ol (150 mmol) and triphenylphosphine (150 mmol) were added. Then DIAD (160 mmol) was dissolved in THF (2 mL) and added dropwise to the solution. After one hour the mixture was concentrated and purified using flash chromatography (toluene/ethyl acetate 3:1). This gave the title compound as a yellow oil.

¹H-NMR (300 MHz, CDCl₃): δ 1.52-1.57 (m, 1H), 1.58 (m, 9H), 1.80-1.83 (m, 1H), 2.00-2.17 (m, 1H), 2.20-2.38 (m, 1H), 3.20-3.37 (m, 1H), 3.80 (s, 3H), 3.81-3.98 (m, 1H), 3.99 (s, 3H), 5.12-5.20 (m, 1H), 5.22-5.40 (m, 1H), 5.63-5.80 (m, 1H), 6.05-6-20 (m, 1H), 7.00-7.21 (m, 4H), 7.40-7.58 (m, 4H), 8.02-8.18 (m, 3H).

EXAMPLE 31

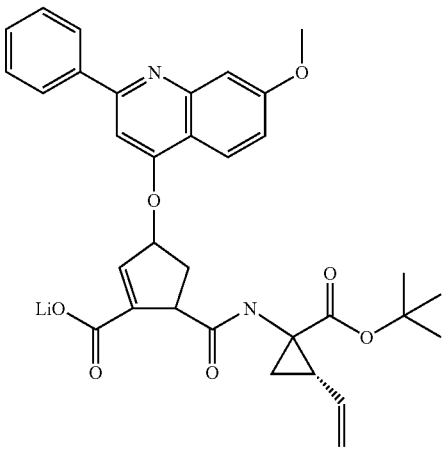

((3R,5R) & (3S,5S))-5-((1R,2S)-1-tert-Butoxycarbonyl-2-vinyl-cyclopropylcarbamoyl)-3-(7-methoxy-2-phenyl-quinolin-4-yloxy)-cyclopent-1-enecarboxylic acid (31)

The methyl ester 30 (35 mg, 59 mmol) was dissolved in dioxane/water (1:1, 4 mL) and LiOH (1.2 mmol) was added. The reaction was stirred over night and then co-concentrated. This gave the title compound (0.32 g, 90%) as a yellow salt.

EXAMPLE 32

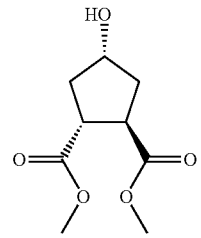

trans-(3R,4R)-Bis(methoxycarbonyl) cyclopentanol (32)

Sodium borohydride (1.11 g, 0.029 mol) was added to a stirred solution of (1R,2S)-4-oxo-cyclopentane 1,2-dicarboxylic acid dimethyl ester (4.88 g, 0.0244 mol) in methanol (300 mL) at 0° C. After 1 h the reaction was quenched with 90 mL brine, concentrated and extracted with ethyl acetate. The organic phases were pooled, dried, filtered and concentrated. The crude product was purified by flash column chromatography (toluene/ethyl acetate 1:1) to give the title compound (3.73 g, 76%) as a yellow oil.

EXAMPLE 33

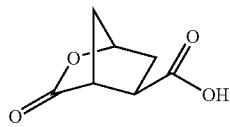

3-Oxo-2-oxa-bicyclo[2.2.1]heptane-5-carboxylic acid (33)

Sodium hydroxide (1M, 74 mL, 0.074 mol) was added to a stirred solution of 30 (3.73 g, 0.018 mol) in methanol (105 mL) at room temperature. After 4 h, the reaction mixture was neutralized with 3M HCl, evaporated and co-evaporated with toluene several times. Pyridine (75 mL) and Ac₂O (53 mL) were added and the reaction mixture was allowed to shake overnight at room temperature. The mixture was then co-evaporated with toluene and purified by flash column chromatography (ethyl acetate+1% acetic acid) to give the title compound (2.51 g, 88%) as a yellow oil.

EXAMPLE 34

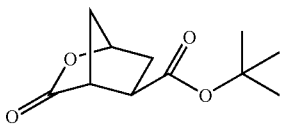

3-Oxo-2-oxa-bicyclo[2.2.1]heptane-5-carboxylic acid tert-butyl ester (34)

DMAP (14 mg, 0.115 mmol) and Boc$_2$O (252 mg, 1.44 mmol) was added to a stirred solution of 33 (180 mg, 1.15 mmol) in 2 mL CH$_2$Cl$_2$ under inert argon atmosphere at 0° C. The reaction was allowed to warm to room temperature and was stirred overnight. The reaction mixture was concentrated and the crude product was purified by flash column chromatography (toluene/ethyl acetate gradient 15:1, 9:1, 6:1, 4:1, 2:1) to give the title compound (124 mg, 51%) as white crystals.

$^1$H-NMR (300 MHz, CD$_3$OD) δ 1.45 (s, 9H), 1.90 (d, J=11.0 Hz, 1H), 2.10-2.19 (m, 3H), 2.76-2.83 (m, 1H), 3.10 (s, 1H), 4.99 (s, 1H); $^{13}$C-NMR (75.5 MHz, CD$_3$OD) δ 27.1, 33.0, 37.7, 40.8, 46.1, 81.1, 81.6, 172.0, 177.7.

EXAMPLE 35

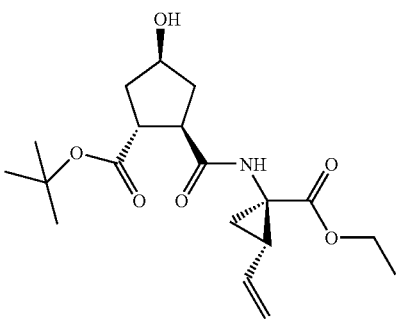

(1R,2R,4S)-2-((1R,2S)-1-Ethoxycarbonyl-2-vinyl-cyclopropylcarbamoyl)-4-hydroxy-cyclopentanecarboxylic acid tert-butyl ester (35)

Compound 34 (56 mg, 0.264 mmol) was dissolved in dioxane/water 1:1 (5 mL) and the mixture was cooled to 0° C. 1 M lithium hydroxide (0.52 mL, 0.520 mmol) was added and the mixture was stirred at 0° C. for 45 minutes, after which the mixture was neutralized with 1M hydrochloric acid and evaporated and coevaporated with toluene. The residue was dissolved in DMF (5 mL) and (1R,2S)-1-amino-2-vinylcyclopropane carboxylic acid ethyl ester hydrochloride (60 mg, 0.313 mmol) and diisopropylethylamine (DIEA) (138 µL, 0.792 mmol) were added and the solution was cooled to 0° C. HATU (120 mg, 0.316 mmol) was added and the mixture was stirred for 0.5 h at 0° C. and for an additional 2 h at room temperature. The mixture was then evaporated and extracted with EtOAc, washed with brine, dried, filtered and concentrated. Purification by flash column chromatography (toluene/EtOAc 1:1) provided the title compound (86 mg, 89%) as a colorless oil.

EXAMPLE 36

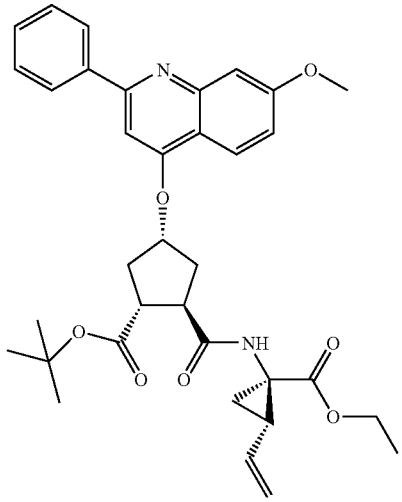

(1R,2R,4R)-2-((1R,2S)-1-Ethoxycarbonyl-2-vinyl-cyclopropylcarbamoyl)-4-(7-methoxy-2-phenyl-quinolin-4-yloxy)-cyclopentanecarboxylic acid tert-butyl ester (36)

Compound 35 (73 mg, 0.199 mmol) was dissolved in dry THF (4 mL) and 2-phenyl-7-methoxy-4-quinolinol (86 mg, 0.342 mmol) and triphenylphosphine (141 mg, 0.538 mmol) were added. The mixture was cooled to 0° C. and DIAD (0.567 mmol) dissolved in 1 mL THF was added dropwise. The mixture was stirred for 48 h at room temperature. The solvent was evaporated and the crude product was purified by flash column chromatography gradient elution (toluene/EtOAc 9:1, 6:1, 4:1) to give the title compound (81 mg, 68%).

EXAMPLE 37

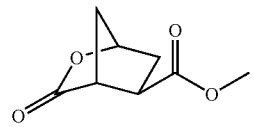

3-Oxo-2-oxa-bicyclo[2.2.1]heptane-5-carboxylic acid methyl ester (37)

Compound 33 (1.014 g, 6.50 mmol) was dissolved in acetone (35 mL) whereafter methyl iodide (13.68 g, 96.4 mmol) and silver(I)oxide (1.61 g, 6.95 mmol) were added. After stirring for 3 h the mixture was filtered through celite and the filtrate was evaporated before purification by flash column chromatography (toluene/ethyl acetate 4:1) was performed yielding the methyl ester (702 mg, 64%) as white crystals.

$^1$H-NMR (300 MHz, CDCl$_3$): δ 1.96 (d, J=10.7 Hz, 1H), 2.21-2.25 (m, 3H), 2.91-2.95 (m, 1H), 3.16 (s, 1H), 3.75 (s, 3H), 4.98 (app. s, 1H).

EXAMPLE 38

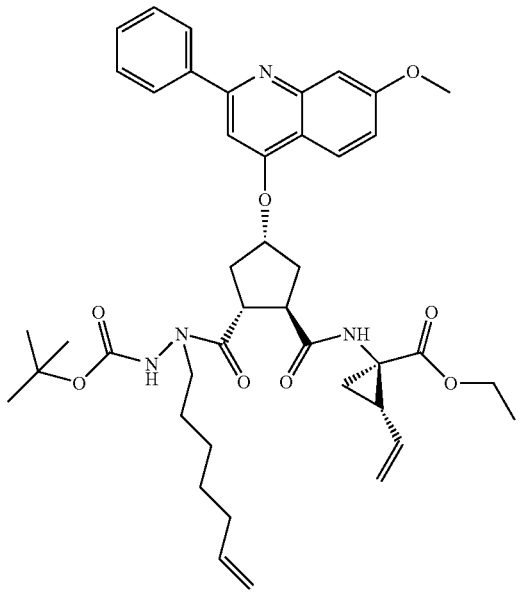

(1R,2S)-1-{[(1R,2R,4R)-2-(N'-tert-Butoxycarbonyl-N-hept-6-enyl-hydrazinocarbonyl)-4-(7-methoxy-2-phenyl-quinolin-4-yloxy)-cyclopentanecarbonyl]-amino}-2-vinyl-cyclopropanecarboxylic acid ethyl ester (38)

Compound 36 (135 mg, 0.225 mmol) and triethylsilane (71 μL, 0.447 mmol) was dissolved in DCM (2 mL) after which trifluoroacetic acid (TFA) (2 mL) was added. The mixture was stirred for 2 h and thereafter co-evaporated with toluene in order to remove the TFA. The residue was dissolved in DMF (3 mL) and 3 (60 mg, 0.263 mmol) and DIEA (118 μL, 0.677 mmol) were added. The temperature was lowered to 0° C. and the coupling reagent O-(7-azabenzotriazol-1-yl)-N,N,N',N'-tetramethyluronium hexafluorophosphate (HATU) (94 mg, 0.247 mmol) was added. The cold solution was allowed to stir for half an hour and then for additional 16 h in room temperature. The solvent was removed by heating the reaction flask in a water bath under diminished pressure. The residue was thereafter dissolved in ethyl acetate and the organic phase was washed three times with brine, dried, filtered and evaporated. Purification by HPLC (MeOH/H$_2$O 90:10 with 0.2% triethylamine) gave 48 (140 mg, 82%) as an oil.

$^1$H-NMR (300 MHz, CDCl$_3$, 40° C.): δ 1.22 (t, J=7.1 Hz, 3H), 1.28-1.42 (m, 6H), 1.46 (s, 9H), 1.52-1.62 (m, 2H), 1.82-1.91 (m, 1H), 1.96-2.16 (m, 3H), 2.18-2.34 (m, 2H), 2.42-2.56 (m, 1H), 2.58-2.72 (m, 1H), 3.42 (app. bs, 3H), 3.66-3.84 (m, 1H), 3.92 (s, 3H), 4.15 (q, J=7.1 Hz, 2H), 4.88-5.02 (m, 2H), 5.07-5.18 (m, 2H), 5.20-5.32 (m, 1H), 5.63-5.84 (m, 2H), 6.62 (bs, 1H), 6.94 (s, 1H), 7.09 (dd, J=2.6, 9.2 Hz, 1H), 7.36-7.51 (m, 4H), 7.99-8.10 (m, 3H); $^{13}$C-NMR (75.5 MHz, CDCl$_3$): δ 14.3, 23.0, 26.4, 26.6, 28.3, 28.6, 33.2, 33.5, 35.6, 37.6, 40.6, 44.7, 47.1, 48.6, 55.5, 61.5, 81.9, 98.4, 107.9, 114.5, 115.6, 118.1, 123.2, 127.6, 128.3, 128.7, 129.1, 133.5, 138.7, 140.7, 151.5, 154.5, 159.2, 160.9, 161.5, 170.5, 174.2, 176.3.

EXAMPLE 39

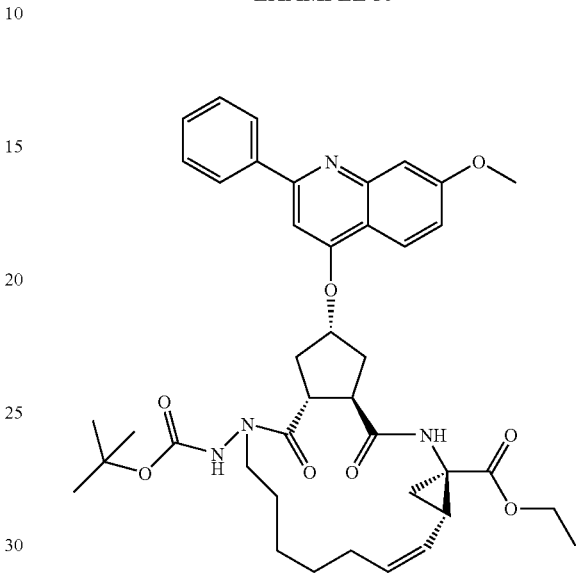

(Z)-(1R,4R,6S,16R,18R)-14-tert-Butoxycarbonylamino-18-(7-methoxy-2-phenyl-quinolin-4-yloxy)-2,15-dioxo-3,14-diaza-tricyclo[14.3.0.0$^{4,6}$]nonadec-7-ene-4-carboxylic acid ethyl ester (39)

A solution of 38 (158 mg, 0.209 mmol) in dry DCM (25 mL) was bubbled with argon for 5 min. To the stirred solution under argon atmosphere was then added a solution of Hoveyda-Grubbs catalyst 2$^{nd}$ generation (11 mg, 0.018 mmol) in dry DCM (5 mL). The mixture was stirred at reflux under argon atmosphere for 16 h. The solvent was evaporated and purification by HPLC (MeOH/H$_2$O 90:10 with 0.2% triethylamine) yielded the target compound (107 mg, 70%) as a colorless solid.

$^1$H-NMR (300 MHz, CD$_3$OD): δ 1.03-1.22 (m, 1H), 1.28 (t, J=7.1 Hz, 3H), 1.32-1.44 (m, 4H), 1.49 (s, 9H), 1.55-1.73 (m, 2H), 1.81-1.91 (m, 1H), 2.04-2.28 (m, 3H), 2.30-2.52 (m, 3H), 2.53-2.70 (m, 1H), 2.86-3.00 (m, 1H), 3.34-3.44 (m, 1H), 3.46-3.62 (m, 1H), 3.95 (s, 3H), 4.19 (q, J=7.1 Hz, 2H), 4.32-4.48 (m, 1H), 5.20-5.33 (m, 1H), 5.34 (bs, 1H), 5.58-5.70 (m, 1H), 7.10 (s, 1H), 7.14 (dd, J=2.5, 9.1 Hz, 1H), 7.39 (d, J=2.5 Hz, 1H), 7.45-7.55 (m, 3H), 8.00 (d, J=8.0 Hz, 2H), 8.17 (d, J=9.3 Hz, 1H); $^{13}$C-NMR (75.5 MHz, CD$_3$OD): δ 14.6, 23.4, 27.5, 27.7, 28.0, 28.5, 30.7, 36.1, 38.1, 42.5, 45.6, 56.0, 62.7, 79.9, 82.8, 100.2, 107.4, 116.6, 119.1, 124.5, 126.5, 128.9, 129.8, 130.5, 135.8, 141.5, 152.2, 156.4, 161.3, 162.5, 163.1, 171.9, 175.8, 179.0. MALDI-TOF-spectrum: (M+H)$^+$ calcd: 727.4. found: 727.5.

EXAMPLE 40

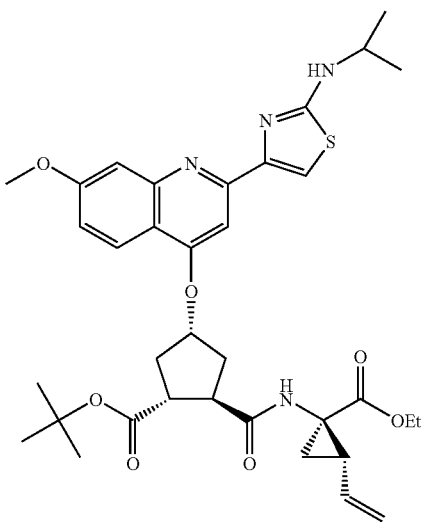

tert-Butyl (1R,2R,4R)-2-[[[(1R)-1-(ethoxycarbonyl)-2-vinylcyclopropyl]amino]carbonyl]-4-[[2-[2-(isopropylamino)-1,3-thiazol-4-yl]-7-methoxyquinolin-4-yl]oxy]cyclopentanecarboxylate (40)

To a solution of compound 35 (0.10 mmol) in dry THF (4 mL) was added the quinoline 12 (0.16 mmol) and Ph₃P (0.40 mmol). After cooling to 0° C. DIAD (0.40 mmol) was added dropwise during 5 min. The solution was stirred at 0° C. for 1 h and at rt for 48 h. The solvent was evaporated and the remainder was purified using flash column chromatography (toluene/EtOAc 1:1) to give the title compound (10%) as a white solid.

EXAMPLE 41

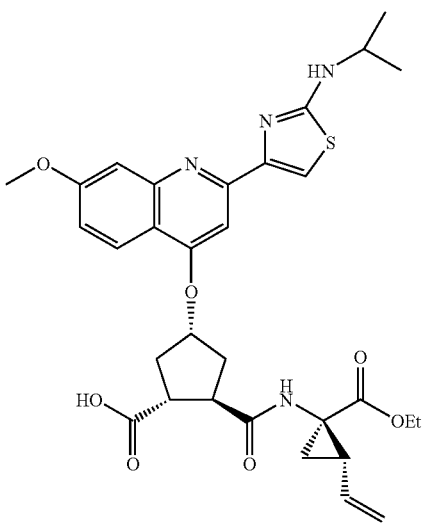

(1R,2R,4R)-2-[[[(1R)-1-(Ethoxycarbonyl)-2-vinylcyclopropyl]amino]carbonyl]-4-[[2-[2-(isopropylamino)-1,3-thiazol-4-yl]-7-methoxyquinolin-4-yl]oxy]cyclopentanecarboxylic acid (41)

To a solution of compound 40 (20 mg, 30 umol) in CH₂Cl₂ (2 mL) was added TFA (2 mL) and Et₃SiH (10 μL, 63 umol). After 2 h the volatiles were evaporated and the product was used without any purification. Title compound: 18 mg, quant. as a white solid.

Quinazolines

EXAMPLE 42

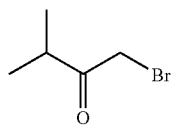

1-bromo-3-methylbutan-2-one (42)

To an ice cooled solution of 3-methyl-2-butanone (25.8 g, 300 mmol) in EtOH (250 ml) was added drop wise bromine (12.9 ml, 250 mmol) and the mixture was stirred for two hours in an ice bath. Petroleum ether (600 ml) was added. The organic phase was washed twice with water. The combined water phases was extracted twice with petroleum ether. The combined organic phases was washed twice with a cold sodium carbonate solution and with brine. The organic phase was dried over sodium sulphate and evaporated under reduced pressure (room temperature). Yield: 50%.

EXAMPLE 43

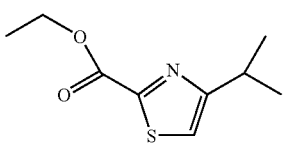

Ethyl 4-isoppropylthiazole-2-carboxylate (43)

To a boiling solution of ethyl thiooxamate (16.0 g, 120 mmol) in EtOH was added drop wise 1-bromo-3-methyl-2-butanone over a period of 15 minutes. The mixture was refluxed for 1.5 hours. The solution was added to 300 ml of ice water and basified with concentrated ammonia solution. The mixture was extracted twice with ethyl acetate. The organic phase was washed with brine, dried with sodium sulphate and evaporated under reduced pressure. The product was purificated by column on chromatography silica gel eluated with hexane and 20% ethyl acetate. Yield: 15.2 g, 67%

¹H-NMR-CDCl₃ 1.35 (d, 6H), 1.42 (t, 3H), 3.25 (m, 1H), 4.49 (m, 2H) 7.20 (s, 1H)

EXAMPLE 44

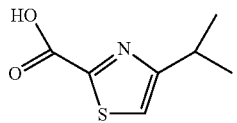

4-isopropylthiazole-2-carboxylic acid (44)

To a solution of ethyl 4-isopropylthiazole-2-carboxylate (9.1 g, 46 mmol) in THF (100 ml) and MeOH (30 ml) was added a solution of lithium hydroxide (1.16 g, 48.5 mmol) and the mixture was stirred for two days at room temperature. The mixture was acidified with 2M hydrochloric acid and extracted four times with diethyl ether. The organic phase was dried with sodium sulphate and evaporated under reduced pressure. Yield: 7.1 g, 90%.

EXAMPLE 45

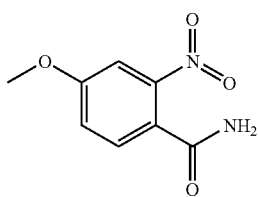

4-methoxy-2-nitro-benzamide (45)

To an ice cooled suspension of 4-methoxy-2-nitro-benzoic acid (14.1 g, 71.5 mmol) and some drops of DMF in DCM (150 ml) was added drop wise oxalyl chloride (19.0 g, 150 mmol) and the mixture was stirred for two hours at room temperature. The solvent was evaporated and water was added. The product was filtered of and washed with water and hexane. The product was dried in vacuum. Yield: 10 g, 71%.

EXAMPLE 46

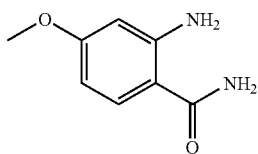

4-methoxy-2-amino-benzamide (46)

A suspension of 4-methoxy-2-nitro-benzamide (6.9 g, 35.1 mmol) in EtOH (200 ml) was hydrogenated with Raney-Ni (4.0 g) for two days at room temperature and 50 psi. The catalyst was filtered of and washed with DMF. The solvent was evaporated under reduced pressure. Yield: 5.6 g, 95%.

EXAMPLE 47

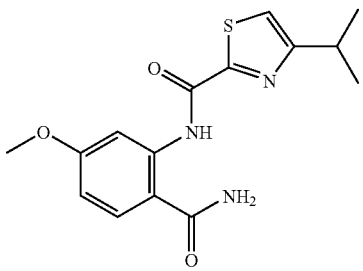

4-isopropylthiazole-2-carboxylic acid (2-carbamoyl-5-methoxy-phenyl)-amide (47)

To a cooled solution of 4-methoxy-2-aminobenzamide (5.6 g, 33.7 mmol), 4-isopropylthiazole-2-carboxylic acid (7.1 g, 42 mmol) and Hobt-hydrate (6.4 g, 42 mmol) in DMF (150 ml) was added EDAC (8.6 g, 45 mmol) and TEA (6.4 ml, 45 mmol) and the mixture was stirred overnight at room temperature. A 2.5% aqueous solution of citric acid (600 ml) was added and the mixture was extracted three times with ethyl acetate. The organic phase was washed with brine and saturated sodium hydrogencarbonate. The solution was dried over sodium sulphate and evaporated under reduced pressure. Yield: 9.0 g, 91%.

EXAMPLE 48

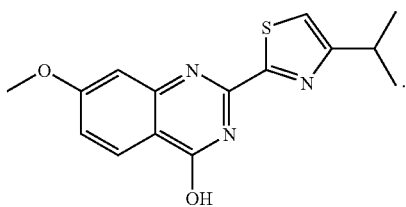

2-(4-isopopylthiazole-2-yl)-7-methoxy-quinazolin-4-ol (48)

A mixture of 4-isopropyl-2-carboxylic acid (2-carbamoyl-5-methoxy-phenyl)-amide (9.0 g, 28.2 mmol) and sodium carbonate (7.5 g, 71 mmol) in EtOH water 50/50 (300 ml) was refluxed for two hours. The mixture was cooled an acidified with citric acid and extracted four times with ethyl acetate. The organic phase was dried with sodium sulphate and evaporated under reduced pressure. The product was crystallized from EtOH. Yield: 4.8 g, 60%.

$^1$H-NMR-DMSO-D$_6$ δ 1.30 (d, 6H), 3.10 (m, 1H), 3.90 (s, 3H), 7.10 (dd, 1H) 7.16 (d, 1H), 7.62 (d, 1H), 8.02 (d, 1H).

EXAMPLE 49

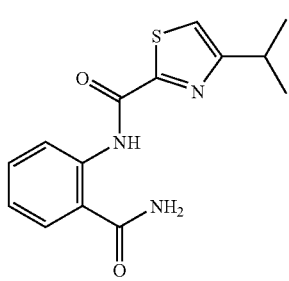

4-isopropylthiazole-2-carboxylic acid
(2-carbamoyl-phenyl)-amide (49)

2-Aminobenzamide (2.04 g, 15 mmol) was reacted with 4-isopropylthiazole-2-carboxylic acid (2.5 g, 14.6 mmol) as described in example 47 which gave the title compound (2.4 g, 56%).

EXAMPLE 50

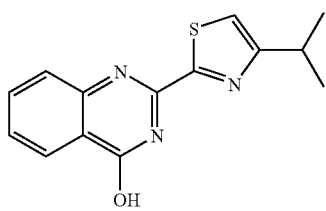

2-(4-isopropylthiazole-2-yl)-quinazolin-4-ol (50)

4-isopropylthiazole-2-carboxylic acid (2-carbamoyl-phenyl)-amide (2.4 g, 8.3 mmol) was treated according to the procedure described in example 48 which gave the title compound (1.7 g, 77%).
$^1$H-NMR CDCl$_3$ δ1.33 (d, 6H), 3.12 (m, 1H), 7.55 (t, 1H), 7.65 (s, 1H), 7.72 (d, 1H), 7.82 (t, 1H), 8.14 (d, 1H).

EXAMPLE 51

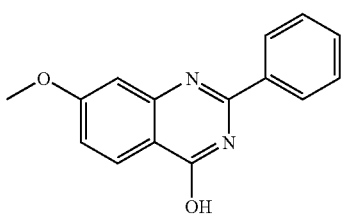

7-Methoxy-2-phenyl-quinazolin-4-ol (51)

Treatment of 2-amino-5-methoxy-benzamide according the procedure described by Raid J. Abdel-Jalil, Wolfgang Voelter and Muhammad Saeed in Tetrahedron Letters 45 (2004) 3475-3476 for the preparation of 2-phenyl-quinazoline 4-ol gave the title compound.

EXAMPLE 52

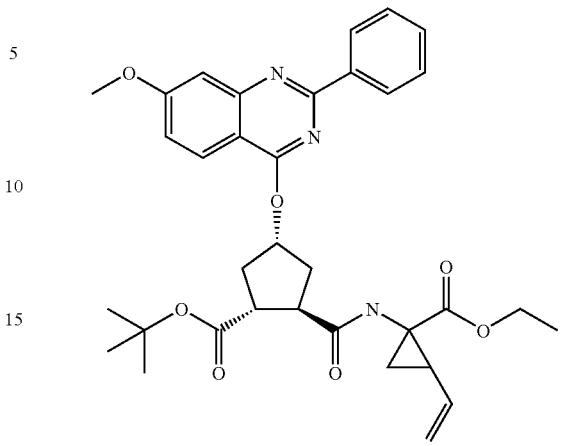

2-(1-Ethoxycarbonyl-2-vinyl-cyclopropylcarbamoyl)-4-(7-methoxy-2-phenyl-quinazolin-4-yloxy)-cyclopentanecarboxylic acid tert-butyl ester (52)

Compound 35 (700 mg, 1.9 mmol), 7-methoxy-2-phenyl-quinazolin-4-ol (670 mg, 2.66 mmol) and triphenyl phosphine (1245 mg, 4.75 mmol) were dissolved in THF (50 ml) and cooled to 0° C. Diisopropyl azidocarboxylate (960 mg, 4.75 mmol) was added slowly and the slurry was allowed to reach room temperature. After 12 h, the solvent was removed under reduced pressure and the residue taken up in ether and filtrated. Purification by column chromatography (SiO$_2$; 1% methanol in dichloromethane) gave the pure title compound (778 mg, 68%). MS (M+H$^+$) 603.

EXAMPLE 53

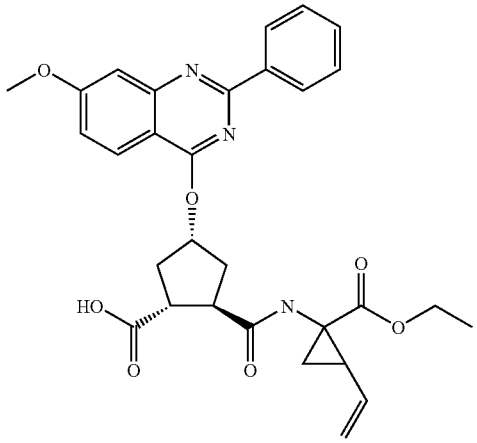

2-(1-Ethoxycarbonyl-2-vinyl-cyclopropylcarbamoyl)-4-(7-methoxy-2-phenyl-quinazolin-4-yloxy)-cyclopentanecarboxylic acid (53)

Compound 52 (780 mg, 1.29 mmol) was dissolved in dichloromethane (20 mL) and triethyl silane (0.4 mL). Trifluoromethane sulfonic acid was added dropwise at room temperature. The mixture was then left for 2 h at room temperature. Removal of the solvent gave pure title product (700 mg, 99%) MS (M+H$^+$) 546.

EXAMPLE 54

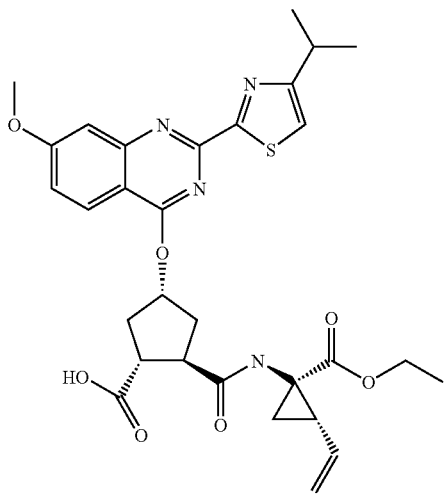

2-(1-Ethoxycarbonyl-2-vinyl-cyclopropylcarbamoyl)-4-[2-(4-isopropyl-thiazol-2-yl)-7-methoxy-quinazolin-4-yloxy]-cyclopentanecarboxylic acid (54)

Compound 56 (850.0 mg, 2.30 mmol), PPh$_3$ (1.60 g, 6 mmol), and the thiazole quinazoline 48 (820 mg, 2.72 mmol) were dissolved in THF (30 mL) in an ice bath. DIAD (1.18 ml, 6 mmol) was added dropwise. After stirring for 30 min, the mixture was stirred at RT for 2 days and then concentrated under vacuum. Flash column chromatography (silica, EtOAc-hexane) gave the Mitsunobu product. To a solution of this product (1.04 g, 1.60 mmol) and triethylsilane (460 mg, 4.00 mmol) in DCM (30 mL), TFA (30 mL) was added dropwise at RT. The mixture was stirred for 2 h at room temperature, evaporated under reduced pressure, and coevaporated twice with toluene. Flash column chromatography (silica, 94/6 DCM-MeOH) gave the title compound as a white solid (950 mg, 70%).

Lotta

EXAMPLE 55

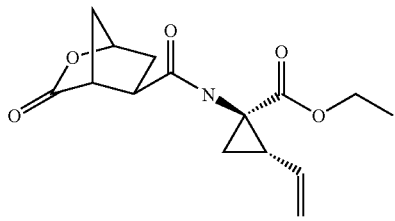

1-[(3-Oxo-2-oxa-bicyclo[2.2.1]heptane-5-carbonyl)-amino]-2-vinyl-cyclopropane carboxylic acid ethyl ester (55)

To a solution of 33 (857 mg, 5.5 mmol), in DMF (14 mL) and DCM (25 mL) at room temperature, was added the hydrochloride of 1-amino-2-vinyl-cyclopropanecarboxylic acid ethyl ester, prepared as described in WO03/099274, (1.15 g, 6.0 mmol), HATU (2.29 g, 6.0 mmol) and DIPEA (3.82 mL, 22 mmol). The reaction was stirred under N$_2$-atmosphere at ambient temperature for 1 h. LC/MS analysis showed complete conversion and the reaction mixture was concentrated in vacuo. The residue was redissolved in DCM (100 mL) and 0.1 M HCl (aq) and the phases were separated. The organic phase was washed with NaHCO$_3$ (aq) and brine, dried (MgSO$_4$) and filtered. Removal of the solvent in vacuo afforded the target compound (1.6 g, 99%). LC/MS>95%, m/z (ESI$^+$)=294 (MH$^+$)

EXAMPLE 56

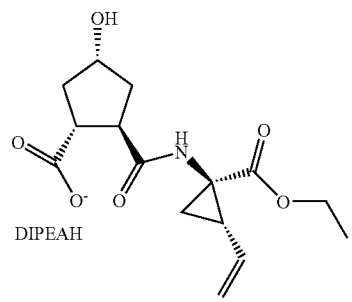

2-(1-Ethoxycarbonyl-2-vinyl-cyclopropylcarbamoyl)-4-hydroxy-cyclopentane carboxylic acid diisopropylethylamine salt (56)

To a solution of 55 (800 mg, 2.73 mmol) in water (15 mL) in a 20 mL microwave reaction vessel was added DIPEA (1.2 mL, 6.8 mmol) and a stirrbar. The reaction vessel was sealed and the immiscible slurry was shaken vigorously before insertion in the microwave cavity. After 1 min of pre-stirring, the reaction was irradiated for 40 min to a set temperature of 100° C. After cooling to 40° C., the transparent solution was concentrated in vacuo, and the residual brown oil co-evaporated 3× with MeCN to remove any residual water. The crude title compound, in the form of a DIPEA salt, was immediately taken forward to the next step. LC/MS>95%, m/z (ESI$^+$)=312 (MH$^+$).

EXAMPLE 57

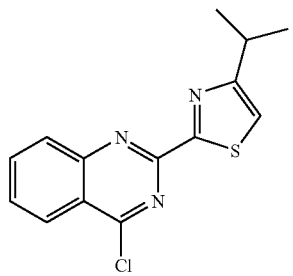

4-Chloro-2-(4-isopropyl-thiazol-2-yl)-quinazoline (57)

Compound 50 (100 mg, 0.37 mmol) was added to phosphorous oxychloride (2 mL) and heated to 100° C. for 2 h. The reaction mixture was then poured on ice with vigorous stirring and made basic with NaOH (aq). The resulting slurry was extracted with ether (3×20 mL) and the combined organic phases were dried (MgSO$_4$) and filtered. Removal of the solvent in vacuo afforded the title compound in quantitative yield. LC/MS>95%, m/z (ESI$^+$)=290 (MH$^+$).

EXAMPLE 58

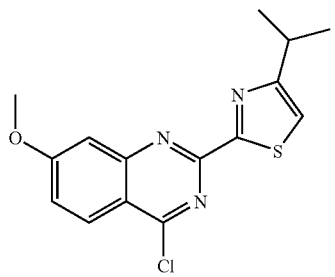

4-Chloro-2-(4-isopropyl-thiazol-2-yl)-7-methoxy-quinazoline (58)

Compound 48 (300 mg, 1 mmol) was added to phosphorous oxychloride (6 mL) and heated to 90° C. for 4 h. The reaction mixture was then poured on ice with vigorous stirring and made basic with NaOH (aq). The resulting slurry was extracted with ether (3×50 mL) and the combined organic phases were dried (MgSO$_4$) and filtered. Removal of the solvent in vacuo afforded the title compound in quantitative yield. LC/MS>95%, m/z (ESI$^+$)=320 (MH$^+$).

EXAMPLE 59

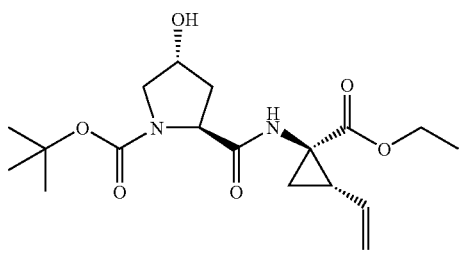

2-(1-Ethoxycarbonyl-2-vinyl-cyclopropylcarbamoyl)-4-hydroxy-pyrrolidine-1-carboxylic acid tert-butyl ester (59)

Boc-protected prolin (4 g, 17.3 mmol), HATU (6.9 g, 18.2 mmol) and 1-amino-2-vinyl-cyclopropanecarboxylic acid ethyl ester prepared as described in WO03/099274, (3.5 g, 18.3 mmol) were dissolved in DMF (60 ml) and cooled to 0° on an ice-bath. Diisopropylethyl amine (DIPEA) (6 ml) was added. The ice-bath was removed and the mixture was left at ambient temperature over-night. Dichloromethane (~80 ml) was then added and the organic phase was washed with aqueous sodium hydrogen carbonate, citric acid, water, brine and dried over sodium sulphate. Purification by flash chromatography (ether→7% methanol in ether) gave pure title compound (6.13 g, 96%)

EXAMPLE 60

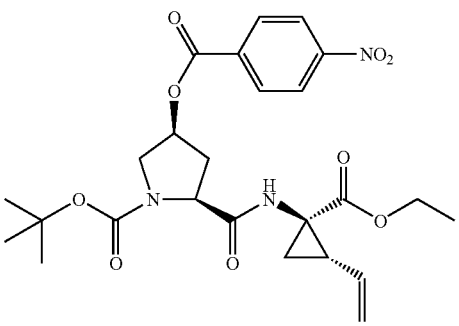

2-(1-Ethoxycarbonyl-2-vinyl-cyclopropylcarbamoyl)-4-(4-nitro-benzoyloxy)-pyrrolidine-1-carboxylic acid tert-butyl ester (60)

Compound 59 (6.13 g, 16.6 mmol), 4-nitrobenzoic acid (4.17 g, 25 mmol) and PPh$_3$ (6.55 g, 25 mmol) was dissolved in THF (130 ml). The solution was cooled to ~0° and diisopropyl azidocarboxylate (5.1 g, 25 mmol) was added slowly. The cooling was then removed and the mixture was left overnight at ambient condition. Aqueous sodium hydrogen carbonate (60 ml) was added and the mixture was extracted with dichloromethane. Purification by flash chromatography (pentane-ether, 2:1→pentane-ether, 1:2→2% methanol in ether) gave pure title compound (6.2 g, 72%).

EXAMPLE 61

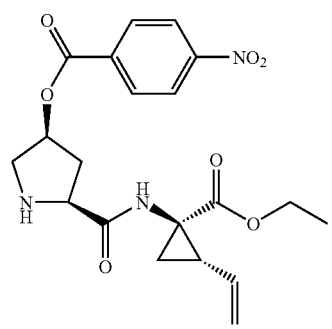

4-Nitro-benzoic acid 5-(1-ethoxycarbonyl-2-vinyl-cyclopropylcarbamoyl)-pyrrolidin-3-yl ester (61)

Compound 62 (6.2 g, 12 mmol) was dissolved in an ice-cold mixture of trifluoromethanesulfonic acid 33% in dichloromethane. The ice-bath was then removed and the mixture was left at room temperature for ~1.5 h. The solvent was evaporated and 0.25 M sodium carbonate added and the mixture was extracted with dichloromethane. Evaporation gave the title compound (4.8 g, 95%) as a yellowish powder.

EXAMPLE 62

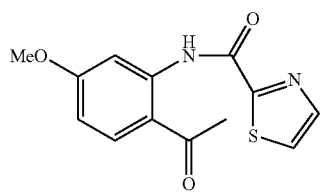

N-(2-acetyl-5-methoxyphenyl)-2-thiazole carboxamide (62)

To a solution of 2-thiazolecarboxaldehyde (500 mg, 3.87 mmol) in 35 mL of pyridine, 1-(2-amino-4-methoxyphenyl)

ethanone (640 mg, 3.87 mmol) was added and the solution was cooled to −30° C. before POCl₃ (750 μl, 8.13 mmol) was added drop wise. The reaction mixture was stirred at −10° C. for 1 hour and then at room temperature for 2 hours. The mixture was concentrated under vacuum and the residue was triturated with NaHCO₃ to pH 7. The precipitate was filtrated, washed with water and dried. The amide was pure enough for the next step without purification (972 mg, 91%).

EXAMPLE 63

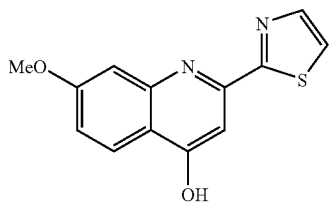

1,4-dihydro-7-methoxy-2-(2-thiazolyl)-4-quinolinol (63)

The precedent amide (441 mg, 1.6 mmol) was dissolved in pyridine (20 mL) and potassium hydroxide (180 mg, 3.2 mmol) was added. The mixture was treated by Micro-Waves (180° C., 30 min). The reaction mixture was concentrated under vacuum and dissolved in a small amount of water. The solution was poured in phosphate buffer (136 mL, pH=7) and stirred for 30 min. The solid was filtered and triturated with EtOAc and dried under vacuum to obtain the quinoline (361 mg, 87%).

EXAMPLE 64

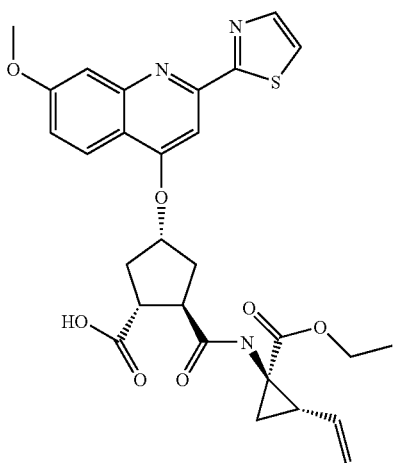

2-(1-Ethoxycarbonyl-2-vinylcyclopropylcarbamoyl)-4-(7-methoxy-2-thiazol-2-yl-quinolin-4-yloxy)-cyclopentanecarboxylic acid (64)

2-(1-Ethoxycarbonyl-2-vinylcyclopropylcarbamoyl)-4-(hydroxy-cyclopentanecarboxylic acid tert-butyl ester (450 mg, 1.22 mmol), PPh₃ (837 mg, 3.19 mmol), and the compound 63 (465 mg, 1.80 mmol) were dissolved in 23 mL THF, cooled on an ice bath. DIAD (0.628 mL, 3.19 mmol) was added drop wise. After stirring for 30 min the mixture was stirred at RT for 2 days, and then concentrated under vacuum. Flash column chromatography (silica, eluant MeOH in CH₂Cl₂ 5%) gave the Mitsunobu product. To a solution of this product (700 mg, 1.15 mmol) and triethylsilane (0.44 mL, 2.74 mmol) in DCM (55 ml), TFA (55 ml) was added drop wise at RT. The mixture was stirred for 2 h at room temperature, evaporated under reduced pressure, and co-evaporated twice with toluene. Flash column chromatography (silica, eluant MeOH in CH₂Cl₂ 2%) gave the title compound as a white solid (424 mg, 63%).

¹H-NMR (CD₃OD): δ 8.12 (d, 1H), 8.09 (d, 1H), 7.90 (d, 1H), 7.66 (s, 1H), 7.47 (d, 1H), 7.24 (dd, 1H), 5.73 (m, 1H), 5.46 (m, 1H), 5.29 (dd, 1H), 5.09 (dd, 1H), 4.13 (m, 2H), 3.99 (s, 3H), 3.48 (m, 1H), 3.35 (m, 1H), 2.65 (m, 1H), 2.48 (m, 2H), 2.30 (m, 1H), 2.18 (m, 1H), 1.75 (dd, 1H), 1.37 (dd, 1H), 1.22 (t, 3H). MS m/z 552 (M+H, 100%), 553 (33%), 554 (12%).

EXAMPLE 65

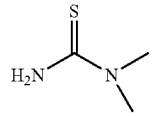

1,1-Dimethyl-thiourea (65)

Dimethylamine (2M in THF, 27.5 mL, 55 mmol) was added to a stirred solution of thiocarbonyldiimidazole (10 g, 56.1 mmol) in dry THF (50 mL). The reaction mixture turned clear by addition and was stirred at 50° C. for 2 hrs. After the reaction mixture had reached rt, it was evaporated on silica and purified by flash chromatography (MeOH:DCM 2:98). The solvent was removed by rotary evaporation and the remaining product dried with high vacuum before it was added to a solution of MeOH (125 mL) saturated with NH₃. The reaction mixture was stirred for 60 hrs until TLC indicated complete consumption of the starting material and LC-MS showed the product peak. The product precipitated while removing the solvent by rotary evaporation. The remaining solvent was diluted with diethyl ether and the white crystals were filtered off and dried to give a yield of 1.16 g (20%). The remaining oil was purified by flash chromatography (MeOH:DCM 5:95) and another 1.87 g (32%) was obtained.

EXAMPLE 66

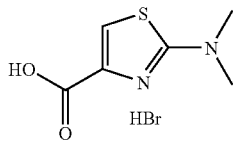

2-Dimethylamino-thiazole-4-carboxylic acid *HBr (66)

3-Bromopyruvic acid (2.94 g, 17.6 mmol) was added to a stirred solution of 1,1-dimethyl-thiourea (1.87 g, 17.6 mmol) in dry THF (60 mL). The reaction mixture was stirred at rt for 4 hrs. The precipitate that had formed was filtered off, washed with cold THF and dried on high vacuum. LC-MS showed the product peak. The product was obtained as a white solid (2.64 g, 59%).

EXAMPLE 67

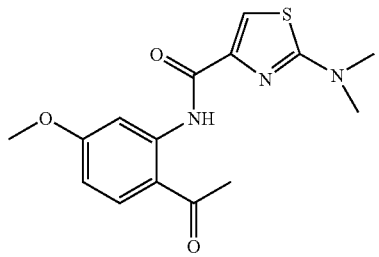

2-Dimethylamino-thiazole-4-carboxylic acid
(2-acetyl-5-methoxy-phenyl)-amide (67)

POCl₃ (2.07 mL, 21.8 mmol) was added to a stirred mixture of 2-dimethylamino-thiazole-4-carboxylic acid *HBr (2.63 g, 10.4 mmol) in dry pyridine (50 mL). The reaction was stirred at rt for 3 hrs and thereafter the solvent was removed by rotary evaporation and the residue dissolved in H₂O. The brown precipitate that was formed was filtered, washed with water and was found to be pure by LC-MS and NMR. The product was obtained as a brown solid (2.85 g, 86%). LRMS (M+H) 320.

EXAMPLE 68

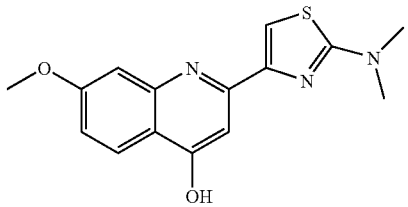

2-(2-Dimethylamino-thiazole-4-yl)-7-methoxy-
quinolin-4-ol (68)

2-Dimethylamino-thiazole-4-carboxylic acid (2-acetyl-5-methoxy-phenyl)-amide (1.29 g, 4.04 mmol) was dissolved in 20 mL pyridine in a microwave vial. Grinded KOH (0.48 g, 8.48 mmol) was added to the solution and the enclosed vial was reacted in the microwave oven at 100° C. for 30 minutes. The mixture was transferred to a round-bottom flask and the solvent was removed by rotary evaporation. The residue was transferred to a beaker with phosphate buffer (pH 7.0, 0.1 M, 300 mL) where the product precipitated while stirring. The precipitate was filtered, rinsed with water and dried with high vacuum. The product was found to be pure by LC-MS and NMR and was obtained in 74% yield (0.90 g). LRMS (M+H) 302.

EXAMPLE 69

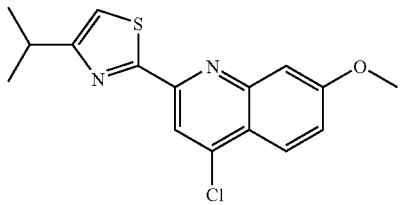

4-Chloro-2-(4-isopropyl-thiazol-2-yl)-7-methoxy-
quinoline (69)

2-(4-Isopropylthiazol-2-yl)-7-methoxyquinolin-4-ol, prepared as described in WO00/59929, (3.6 g) was mixed with 20 ml of phosphorus oxychloride and heated at 100° C. for 40 min. Reaction was monitored by LC-MS. After 40 min of heating the excess of phosphorus oxychloride was removed by rotary evaporation. The residual oil was mixed with sat. sodium bicarbonate solution and extracted into ether (3×70 ml). The combined organic extracts were washed with brine, dried over magnesium sulfate, concentrated by rotary evaporation and passed through short pad of silica (hexane) to give the title compound as a white powder 3.6 g (yield 62%).

EXAMPLE 70

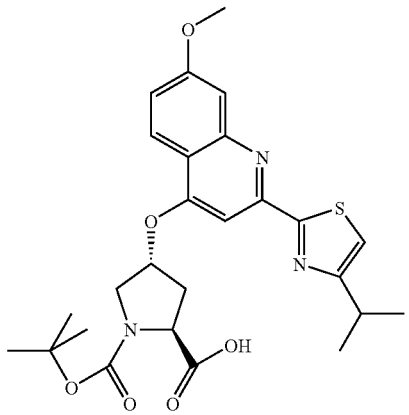

4-[2-(4-Isopropyl-thiazol-2-yl)-7-methoxy-quinolin-
4-yloxy]-pyrrolidine-1,2-dicarboxylic acid 1-tert-
butyl ester (70)

To a stirred solution of N-Boc-trans-4-hydroxy-L-proline (2.6 g, 11.2 mmol) in DMSO (80 mL) was added potassium tert-butoxide (3.8 g, 3 eq). After approx. 1 hr of stirring 4-chloro-2-phenyl-7-methoxy quinoline (3.6 g, 11.2 mmol) was added and the reaction mixture was stirred at room temperature overnight. The mixture was diluted with water (350 mL) and neutralized with 1N HCl. The resulting suspension was extracted into ethylacetate (3×100 ml), washed with brine and dried over magnesium sulfate. Filtration and concentration by rotary evaporation gave after drying overnight on high vacuum 3.6 g of the title compound (yield 62%). Purity by HPLC >95%. M+H⁺ 514.

EXAMPLE 71

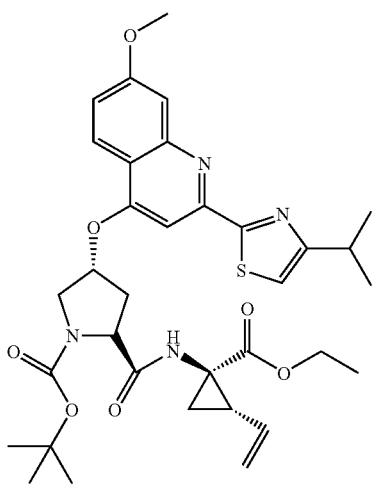

2-(1'-Ethoxycarbonyl-2-vinyl-cyclopropylcarbamoyl)-4-[2-(4-isopropyl-thiazol-2-yl)-7-methoxy-quinolin-4-yloxy]-pyrrolidine-1'-carboxylic acid tert-butyl ester (71)

Acid 70 (3.6 g, 7 mmol) was mixed with the hydrochloride of 1'-methyl-2-vinyl-cyclopropanecarboxylic acid methyl ester, prepared as described in WO03/099274, (1.47 g, 7.6 mmol), dissolved in DMF. The reaction mixture was flushed with argon and cooled down in an ice bath and Hunigs base (1.5 ml) was added in one portion and the reaction mixture was stirred for 10-15 min. HATU (2.93 g, 7.7 mmol) was added to the cold reaction mixture in one portion and the reaction mixture was stirred for about 40 min in an ice bath (reaction was monitored by LC-MS). After 40 min the reaction mixture was concentrated by rotary evaporation (not to complete dryness), mixed with sat. sodium bicarbonate solution and extracted into EtOAc (3×1100 ml), washed with brine, dried over magnesium sulfate and concentrated by rotary evaporation. Purified by column chromatography on silica (dissolved in DCM) and then applied on YMC silica (200 g, eluent hex/EA 3:2 then 2:3) to give 3.81 g of pure white compound (yield 84%).

EXAMPLE 72

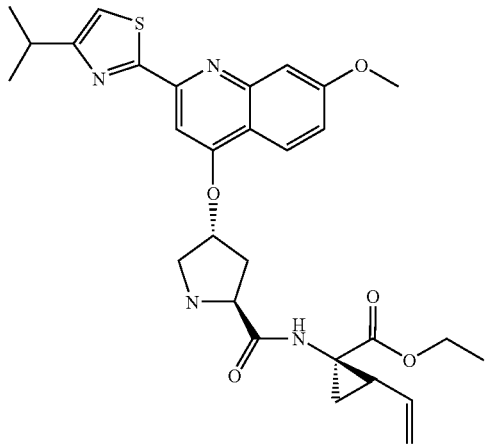

1-({4-[2-(4-Isopropyl-thiazol-2-yl)-7-methoxy-quinolin-4-yloxy]-pyrrolidine-2-carbonyl}-amino)-2-vinyl-cyclopropanecarboxylic acid ethyl ester (72)

Compound 71 (3.81 g, 5.8 mmol) was dissolved in dichloromethane (30 ml) and trifluoromethanesulphonic acid (30 ml). The mixture was stirred for about 1.5 h at room temp. The solvent was then removed by rotary evaporation. Saturated sodium bicarbonate (100 ml) was added to the obtained oil and the mixture was extracted with ether (3×100 ml). The ether layers were combined, washed with brine, dried over magnesium sulfate (overnight) and concentrated by rotary evaporation to give pure title compound (3.13 g after drying overnight on high vacuum, 98.3%). MS (M+H+) 551.

Carbamates

EXAMPLE 73

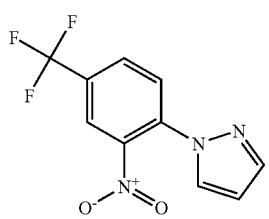

1-(2-Nitro-4-trifluoromethyl-phenyl)-1H-pyrazole (73)

1-Fluoro-2-nitro-4-trifluoromethyl-benzene (209 mg, 1 mmol) was dissolved in EtOH (4.5 mL) in a 5 mL microwave reaction vessel. 1H-pyrazole (83.5 mg, 1.2 mmol), DIPEA (329 μL, 2 mmol) and a stirrbar was added followed by sealing of the reaction vessel. The reaction mixture was then heated in the microwave for 30 min at 120° C. The reaction was concentrated in vacuo and the residue purified by flash chromatography (Silica, Hexane: EtOAc) to afford the title compound (206 mg, 81%). LC/MS>95%, m/z (ESI+)=258 (MH+).

EXAMPLE 74

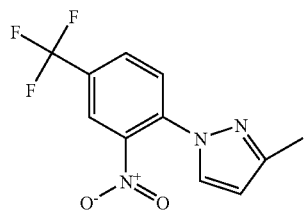

3-Methyl-1-(2-nitro-4-trifluoromethyl-phenyl)-1H-pyrazole (74)

The title compound was synthesised according to the procedure described in Example 73, except that 3-methyl-1H-pyrazole replaced 1H-pyrazole. TLC (Silica; Hexane:EtOAc, 4:1): Rf=0.3; LC/MS>95%, m/z (ESI+)=272 (MH+).

EXAMPLE 75

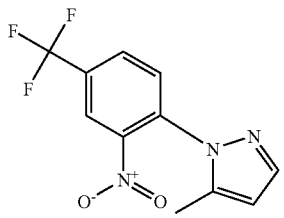

5-Methyl-1-(2-nitro-4-trifluoromethyl-phenyl)-1H-pyrazole (75)

The title compound was synthesised according to the procedure described in Example 73, except that 3-methyl-1H-pyrazole replaced 1H-pyrazole. The 3-methyl-1H-pyrazole partially rearranges to 5-methyl-1H-pyrazole during the conditions in Example 10-1. TLC (Silica; Hexane:EtOAc, 4:1): Rf=0.4; LC/MS>95%, m/z (ESI$^+$)=272 (MH$^+$).

EXAMPLE 76

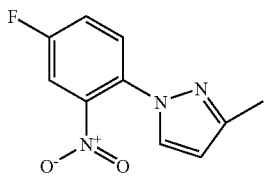

1-(4-Fluoro-2-nitro-phenyl)-3-methyl-1H-pyrazole (76)

The title compound was synthesised according to the procedure described in Example 73, except that 3-methyl-1H-pyrazole replaced 1H-pyrazole. TLC (Silica; Hexane:EtOAc, 4:1): Rf=0.3; LC/MS>95%, m/z (ESI$^+$)=222 (MH$^+$).

EXAMPLE 77

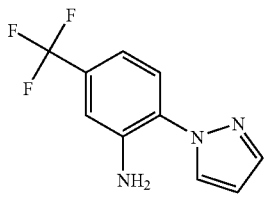

2-Pyrazol-1-yl-5-trifluoromethyl-phenylamine (77)

Compound 73 (206 mg, 0.8 mmol) was dissolved in EtOH (25 mL) in a 50 mL flask. 2 spatulas of 5% Pd on Activated Carbon and a stirrbar was added followed by evacuation and N$_2$(g) purging of the flask. H$_2$(g) was then introduced into the flask by a balloon and the reaction stirred at room temperature under H$_2$-atmosphere for 2 h. The H$_2$(g) inlet was closed and the flask evacuated and N$_2$(g) purged 3 times. LC/MS analysis showed complete hydrogenation and the mixture was filtered through a plug of Celite before removal of the solvent in vacuo to afford the crude aniline (163 mg, 90%). LC/MS, >95%, m/z (ESI$^+$)=228 (MH$^+$).

EXAMPLE 78

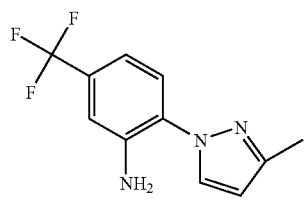

2-(3-Methyl-pyrazol-1-yl)-5-trifluoromethyl-phenylamine (78)

The title compound was synthesised according to the procedure described in Example 77. LC/MS>95%, m/z (ESI$^+$)=242 (MH$^+$).

EXAMPLE 79

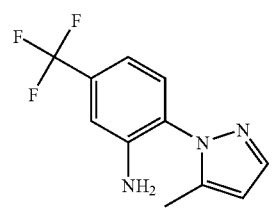

2-(5-Methyl-pyrazol-1-yl)-5-trifluoromethyl-phenylamine (79)

The title compound was synthesised according to the procedure described in Example 77. LC/MS>95%, m/z (ESI$^+$)=242 (MH$^+$).

EXAMPLE 80

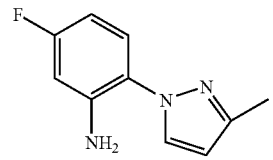

5-Fluoro-2-(3-methyl-pyrazol-1-yl)-phenylamine (80)

The title compound was synthesised according to the procedure described in Example 77. LC/MS>95%, m/z (ESI$^+$)=192 (MH$^+$).

Dialkylhydrazines

EXAMPLE 81

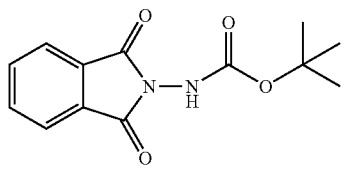

N-tert-butyloxycarbonylaminophthalimide (81)

A mixture of phthalic anhydride (29.63 g, 200 mmol) and tert-butylcarbazate (26.40 g, 200 mmole) in toluene was refluxed for two hours using a Dean-Stark trap. The mixture was allowed to cool and crystallize overnight. The crystals were filtered of and washed with cold toluene. The crystals were dried in vacuum.

Yield: 48.7 g=92%

EXAMPLE 82

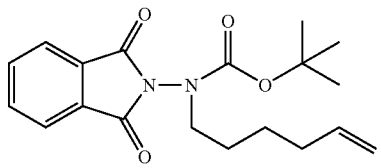

N-Hex-5-enyl-N-tert-butyloxycarbonylaminophthalimide (82)

To an ice cooled solution of N-tert-butyloxycarbonylaminophthalimide (19.80 g, 75 mmol), 5-hexen-1-ol (13.5 ml, 111 mmol) and triphenylphosphine (29.5 g, 111 mmol) in dry THF (300 ml) was added drop wise DIAD (22.2 ml, 111 mmol) and the mixture was stirred overnight at room temperature. The solvent was evaporated under reduced pressure and ether (200 ml) was added. The mixture was allowed to stay for five hours and the precipitated triphenylphosphine oxide was removed by filtration. The solvent was removed in vacuum. Yield: 35 g crude product.

EXAMPLE 83

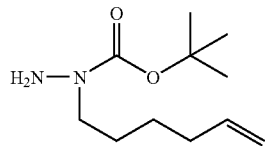

N-Hex-5-enyl-hydrazinecarboxylic acid tert-butylester (83)

The crude product from example 82 was dissolved in THF (200 ml) and hydrazine monohydrate (5.63 g, 112 mmol) was added. The mixture was stirred for five days at room temperature and the precipitated phthalyhydrazide was removed by filtration. The solution was evaporated and the product was purificated by column chromatography on silica gel, using dichloromethane:methanol 99:1 as eluent. Yield: 15 g, 93% from compound 81.

EXAMPLE 84

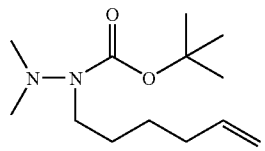

N-Hex-5-enyl-N',N'-dimethyl-hydrazinecarboxylic acid tert-butylester (84)

To an ice cooled solution of N-hex-5-enyl-hydrazinecarboxylic acid tert-butylester (5.10 g, 23.8 mmol) in dry DMF (100 ml) was added a 60% sodium hydride suspension (2.00 g, 50 mmol) and the mixture was stirred for two hours at room temperature. The mixture was cooled on an ice bath and methyl iodide (10.64 g, 75 mmol) was added slowly. The mixture was stirred overnight at room temperature. Water was added and the mixture was extracted three times with ethyl acetate. The organic phase was washed two times with brine, dried with sodium sulphate and evaporated under reduced pressure. The product was isolated by column chromatography on silica gel using hexane:ethyl acetate (10%-20% ethyl acetate: 90-80% hexane) as eluent.

Yield: 2.0 g=36% (the monomethylated product was isolated as a byproduct).

EXAMPLE 85

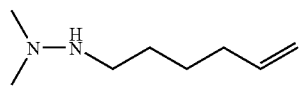

N-Hex-5-enyl-N,N-dimethylhydrazine (85)

To a solution of compound 5 (1.90 g, 7.8 mmol) in dichloromethane (25 ml) was added TFA and the solution was stirred for three hours at room temperature.

The solvent was evaporated under reduced pressure and a 2M solution of NaOH was added. The product was extracted four times with dichloromethane. The organic phase was dried with sodium sulphate and evaporated under reduced pressure.

Yield: 1.0 g=90%

1H NMR (CDCl$_3$) δ 1.40-1.54 (m, 4H) 2.06 (m, 2H) 2.44 (s, 6H) 2.75 (m, 2H) 5.00 (m, 2H) 5.8 (m, 1H).

EXAMPLE 86

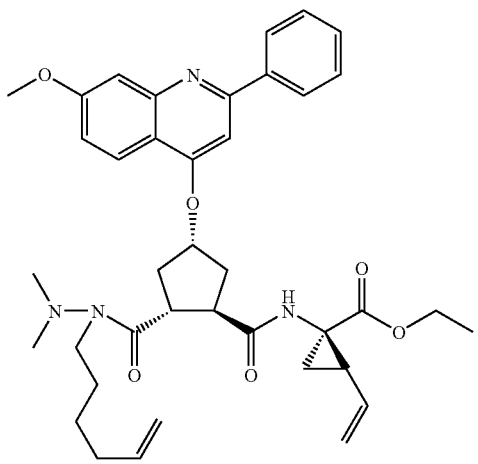

1-{[2-(N-Hex-5-enyl-N,N'-dimethylhydrazinocarbonyl)-4-(7-methoxy-2-phenyl-quinolin-4-yloxy)-cyclopntanecarbonyl]-amino}-2-vinyl-cycloprpanecarboxylic acid ethyl ester (86)

Compound 36 (135 mg, 0.225 mmol) and triethylsilane (71 μL, 0.447 mmol) was dissolved in DCM (2 mL) after which trifluoroacetic acid (TFA) (2 mL) was added. The mixture was stirred for 2 h and thereafter co-evaporated with toluene in order to remove the TFA. The residue was dissolved in DMF (15 mL) and 85 (142 mg, 1.0 mmol) and DIEA (530 μL, 3.10 mmol) were added. The temperature was lowered to 0° C. and the coupling reagent O-(7-azabenzotriazol-1-yl)-N,N,N',N'-tetramethyluronium hexafluorophosphate (HATU) (261 mg, 0.68 mmol) was added. The cold solution was allowed to stir for half an hour and then for additional 16 h in room temperature. The solvent was removed by heating the reaction flask in a water bath under diminished pressure. The residue was thereafter dissolved in ethyl acetate and the organic phase was washed three times with brine, dried, filtered and evaporated. Purification gave 48 (160 mg, 53%) as an oil.

EXAMPLE 87

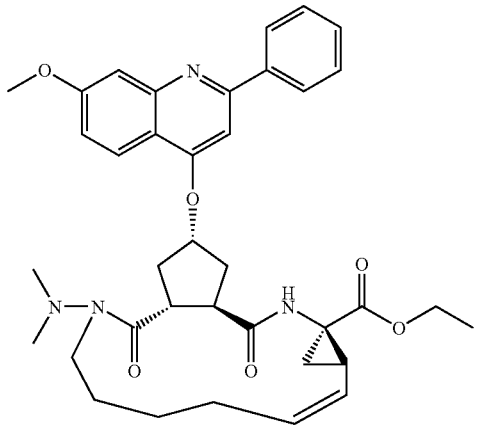

13-Dimethylamino-17-(7-methoxy-2-phenyl-quinolin-4-yloxy-2,14-dioxo-3,13-diaza-tricyclo[13.3.0.0*4,6*]octadec-7-ene-4-carboxylic acid ethyl ester (7)

A solution of 86 (145 mg, 0.216 mmol) in dry DCM (145 mL) was bubbled with argon for 5 min. To the stirred solution under argon atmosphere was then added a solution of Hoveyda-Grubbs catalyst $2^{nd}$ generation (14.5 mg) in dry DCM (5 mL). The mixture was stirred at reflux under argon atmosphere for 16 h. The solvent was evaporated and purification yielded the title compound (100 mg, 71%) as a colorless solid.

EXAMPLE 88

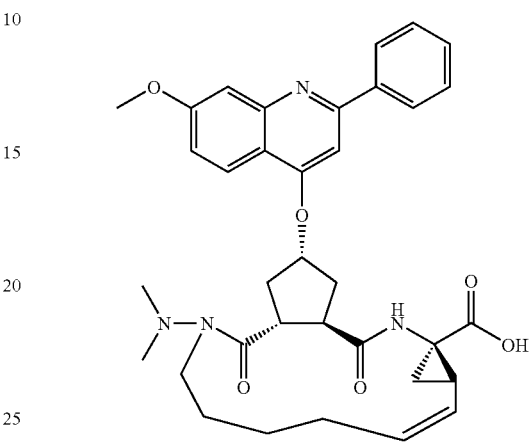

13-Dimethylamino-17-(7-methoxy-2-phenyl-quinolin-4-yloxy-2,14-dioxo-3,13-diaza-tricyclo [13.3.0.0*4,6*]octadec-7-ene-4-carboxylic acid (8)

To a solution of 87 (93 mg, 0.145 mmol) in THF/MeOH/H$_2$O 2:1:1 (10 mL) was added 1 M LiOH (600 μL, 0.600 mmol). The solution was stirred for 24 h at room temperature and finally for one hour at reflux. After acidification to pH 3-4 with 1 M HCl and evaporation the residue was purified providing the title compound (40 mg, 45%) as a colorless solid.

EXAMPLE 89

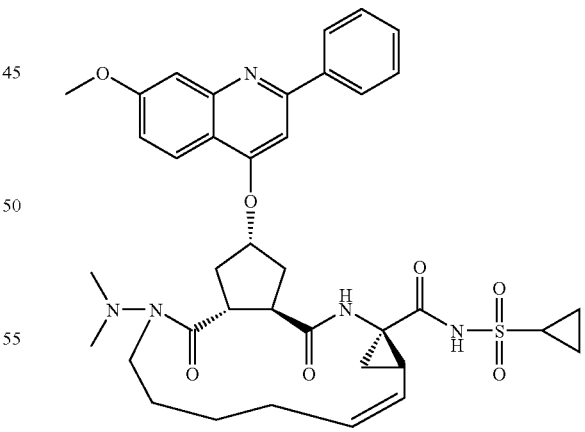

Cyclopropanesulphonic acid [13-dimethylamino-17-(7-methoxy-2-phenyl-quinolin-4-yloxy)-2,14-dioxo-3,13-diaza-tricyclo[13.3.0.0*4,6*]octadec-7-ene-4-carbonyl]-amide (9)

To a solution of the acid 8 (37 mg, 0.060 mmol) in DMF (1 mL) was added. DMAP (14.6 mg, 0.12 mmol) and EDAC (28.8 mg, 0.12 mmol). The solution was stirred at room temperature for 6 h prior to the addition of a solution containing cyclopropylsulfonamide (36 mg, 0.3 mmol), and DBU (45.6 mg, 0.3 mmol) in dry DMF (1.5 mL). The mixture was stirred at room temperature over night, acidified with 5% aqueous solution of citric acid, extracted with ethyl acetate. The combined organic layers were dried, concentrated and subjected to purification by HPLC, which gave the title compound (10 mg), Purity by HPLC >95%, M+H$^+$ 716.

EXAMPLE 90

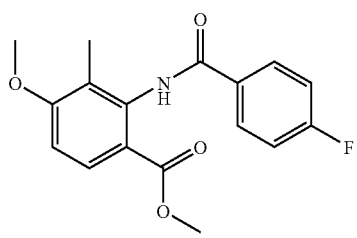

2-(4-Fluoro-benzoylamino)-4-methoxy-3-methyl-benzoic acid methyl ester (90)

4-Fluoro benzoic acid (700 mg, 5 mmol) was dissolved in dichloromethane (20 ml) and pyridine (2 ml). 2-Amino-4-methoxy-3-methyl-benzoic acid methyl ester (81) (878 mg, 4.5 mmol) was added and the mixture was refluxed for 5 h. Water was added and the mixture was extracted with dichloromethane. The organic phase was dried, filtered and evaporated and the afforded residue was purified by column chromatography on silica gel, eluted with ether-pentane 1:1 which gave pure title compound (870 mg, 61%). MS (M+H$^+$) 318.

EXAMPLE 91

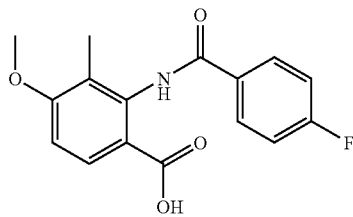

2-(4-Fluoro-benzoylamino)-4-methoxy-3-methyl-benzoic acid (91)

LiOH (1M, 4 mL) was added to a solution of 2-(4-fluoro-benzoylamino)-4-methoxy-3-methyl-benzoic acid methyl ester (90) (870 mg, 2.7 mmol), in tetrahydrofuran (15 ml), water (7.5 ml) and methanol (7.5 ml). The mixture was heated to 50° C. for 4 h. Water (30 ml) was then added and the volume reduced to half. Acidification with acetic acid followed by filtration gave pure title compound (830 mg, 100%).

MS (M+H$^+$) 304.

EXAMPLE 92

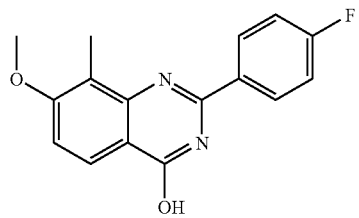

2-(4-Fluoro-phenyl)-7-methoxy-8-methyl-quinazolin-4-ol (92)

2-(4-Fluoro-benzoylamino)-4-methoxy-3-methyl-benzoic acid (91) (830 mg, 2.7 mmol) was heated to 150° C. in formamide (20 ml) for 4 h. The excess formamide was removed by distillation. Water was added and the precipitated product was filtered of to give pure title compound (642 mg, 83%).

MS (M+H$^+$) 285.

EXAMPLE 93

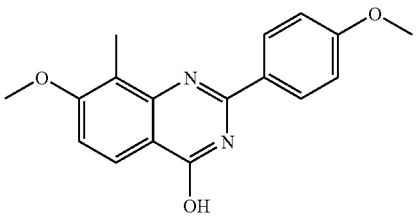

7-Methoxy-8-methyl-2-(4-methoxyphenyl)-quinazolin-4-ol (93)

To a suspension of 2-amino-4-methoxy-3-methyl benzamide in dry THF (60 ml) was added pyridine (2 eq) and the mixture was cooled to 5° C. 4-Methoxybenzoic acid chloride (1.25 eq) was added slowly and the mixture was stirred at room temperature overnight. The mixture was evaporated under reduced pressure and then suspended in water. The compound was left in the water for some hours, filtered and washed with cold water and diethyl ether and dried under vacuum. The residue was then added to a suspension of sodium carbonate (2.5 eq) in a 1:1 mixture of water and EtOH and the mixture was refluxed for two hours. The EtOH was removed under reduced pressure, a solution of 5% citric acid was added and the mixture was allowed to stay overnight. The title compound was isolated by filtration, then washed with water and diethyl ether and dried under vacuum. (5.5 g, 92%).

$^1$H-NMR DMSO-D$_6$ δ 2.38 (s, 3H), 3.82 (s, 3H), 3.92 (s, 3H), 7.04 (d, 2H), 7.20 (d, 1H), 8.00 (d, 1H), 8.20 (d, 2H), 12.18 (s, 1H).

EXAMPLE 94

Alternative Method for the Preparation of Compound 35

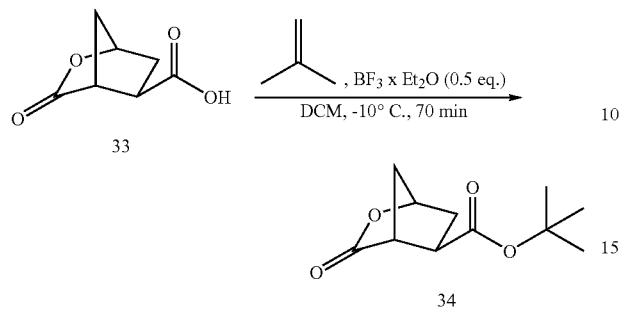

Compound 33 (13.9 g, 89 mmol) was dissolved in dichloromethane (200 ml) and then cooled to approximately −10° C. under nitrogen. Isobutylene was then bubbled into the solution until the total volume had increased to approximately 250 ml which gave a "clowdy solution". $BF_3{\times}Et_2O$ (5.6 ml, 44.5 mmol, 0.5 eq.) was added and the reaction mixture was kept at approximately −10° C. under nitrogen. After 10 min, a clear solution was obtained. The reaction was monitored by TLC (EtOAc-Toluene 3:2 acidified with a few drops of acetic acid and hexane-EtOAc 4:1, staining with basic permanganate solution). At 70 min only traces of compound 13 remained and aq. saturated $NaHCO_3$ (200 ml) was added to the reaction mixture, which was then stirred vigorously for 10 min. The organic layer was washed with saturated $NaHCO_3$ (3×200 ml) and brine (1×150 ml), then dried with sodium sulfite, filtered and concentrated into an oil containing small droplets. Upon addition of hexane to the residue the product crashed out. Addition of more hexane and heating to reflux gave a clear solution from which the product crystallized. The crystals were collected by filtration and was washed with hexane (rt), then air-dried for 72 h giving colourless needles (12.45 g, 58.7 mmol, 66% from first harvest)

EXAMPLE 95

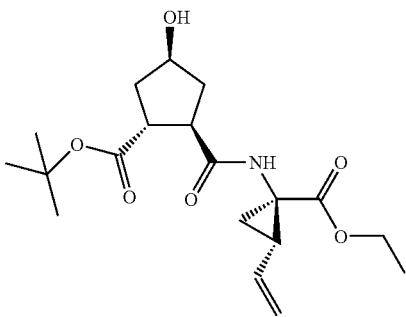

(1R,2R,4S)-2-((1R,2S)-1-Ethoxycarbonyl-2-vinyl-cyclopropylcarbamoyl)-4-hydroxy-cyclopentanecarboxylic acid tert-butyl ester (35)

Compound 34 (56 mg, 0.264 mmol) was dissolved in dioxane/water 1:1 (5 mL) and the mixture was cooled to 0° C. 1 M lithium hydroxide (0.52 mL, 0.520 mmol) was added and the mixture was stirred at 0° C. for 45 minutes, after which the mixture was neutralized with 1M hydrochloric acid and evaporated and coevaporated with toluene. The crystalline residue was dissolved in DMF (5 mL) and (1R,2S)-1-amino-2-vinylcyclopropane carboxylic acid ethyl ester hydrochloride (60 mg, 0.313 mmol) and diisopropylethylamine (DIEA) (138 μL, 0.792 mmol) were added and the solution was cooled to 0° C. HATU (120 mg, 0.316 mmol) was added and the mixture was stirred for 0.5 h at 0° C. and for an additional 2 h at room temperature. The mixture was then evaporated and extracted with EtOAc, washed with brine, dried, filtered and concentrated. Purification by flash column chromatography (toluene/EtOAc 1:1) provided the title compound (86 mg, 89%) as a colourless oil. The afforded oil was crystallised from ethyl acetate-hexane.

BIOLOGICAL EXAMPLE 1

Activity of Compounds of Formula (I) in HCV Replicon Assays

The compounds of formula (I) were examined for activity in the inhibition of HCV RNA replication in a cellular assay. The assay demonstrated that the compounds of formula (I) exhibited activity against HCV replicons functional in a cell culture. The cellular assay was based on a bicistronic expression construct, as described by Lohmann et al. (1999) Science vol. 285 pp. 110-113 with modifications described by Krieger et al. (2001) Journal of Virology 75: 4614-4624, in a multi-target screening strategy. In essence, the method was as follows.

The assay utilized the stably transfected cell line Huh-7 luc/neo (hereafter referred to as Huh-Luc). This cell line harbors an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter portion (FfL-luciferase), and a selectable marker portion ($neo^R$, neomycine phosphotransferase). The construct is bordered by 5' and 3' NTRs (non-translated regions) from HCV type 1b. Continued culture of the replicon cells in the presence of G418 ($neo^R$) is dependent on the replication of the HCV RNA. The stably transfected replicon cells that express HCV RNA, which replicates autonomously and to high levels, encoding inter alia luciferase, are used for screening the antiviral compounds.

The replicon cells were plated in 384 well plates in the presence of the test and control compounds which were added in various concentrations. Following an incubation of three days, HCV replication was measured by assaying luciferase activity (using standard luciferase assay substrates and reagents and a Perkin Elmer ViewLux™ ultraHTS microplate imager). Replicon cells in the control cultures have high luciferase expression in the absence of any inhibitor. The inhibitory activity of the compound on luciferase activity was monitored on the Huh-Luc cells, enabling a dose-response curve for each test compound. EC50 values were then calculated, which value represents the amount of the compound required to decrease by 50% the level of detected luciferase activity, or more specifically, the ability of the genetically linked HCV replicon RNA to replicate.

Results are typically tabulated in ranges such as:
value A corresponds to an $EC_{50}$ between 10 μM and 1 μM;
value B corresponds to an $EC_{50}$ between 0.99 μM and 50 nM;
value C corresponds to an $EC_{50}$ between 49 nM and 0.5 nM.

BIOLOGICAL EXAMPLE 2

Inhibition Assay

The aim of this in vitro assay is to measure the inhibition of HCV NS3/4A protease complexes by the compounds of the present invention. This assay provides an indication of how effective compounds of the present invention would be in inhibiting HCV NS3/4A proteolytic activity.

The inhibition of full-length hepatitis C NS3 protease enzyme was measured essentially as described in Poliakov, 2002 Prot Expression & Purification 25 363 371. Briefly, the hydrolysis of a depsipeptide substrate, Ac-DED(Edans)EEA-buψ[COO]ASK(Dabcyl)-NH$_2$ (AnaSpec, San José, USA), was measured spectrofluorometrically in the presence of a peptide cofactor, KKGSVVIVGRIVLSGK (Åke Engström, Department of Medical Biochemistry and Microbiology, Uppsala University, Sweden). [Landro, 1997 #Biochem 36 9340-9348]. The enzyme (1 nM) was incubated in 50 mM HEPES, pH 7.5, 10 mM DTT, 40% glycerol, 0.1% n-octyl-D-glucoside, with 25 μM NS4A cofactor and inhibitor at 30° C. for 10 min, whereupon the reaction was initiated by addition of 0.5 μM substrate. Inhibitors were dissolved in DMSO, sonicated for 30 sec. and vortexed. The solutions were stored at −20° C. between measurements.

The final concentration of DMSO in the assay sample is adjusted to 3.3%. The rate of hydrolysis is corrected for inner filter effects according to published procedures. [Liu, 1999 Analytical Biochemistry 267 331-335]. Ki values are estimated by non-linear regression analysis (GraFit, Erithacus Software, Staines, MX, UK), using a model for competitive inhibition and a fixed value for Km (0.15 μM). A minimum of two replicates are performed for all measurements.

Results are typically tabulated in ranges such as
value E corresponds to a Ki>2 μM;
value F corresponds to a Ki between 2 μM and 100 nM;
value G corresponds to a Ki between 99.9 nM and 5 nM;
value H corresponds to a Ki between 4.9 nM and 0.1 nM.

Representative compounds of the invention perform as shown in Table 1

| Example nr. | EC$_{50}$ Replicon assay | Ki Enzymatic assay |
|---|---|---|
| Example 88 | A | F |
| Example 89 | C | H |

The invention claimed is:
1. A compound of the formula I:

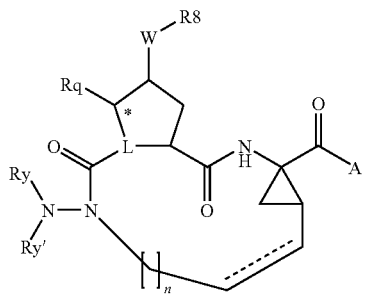

and N-oxides, salts and stereoisomers thereof
wherein
A is OR$^1$, NHS(=O)$_p$R$^2$, NHR$^3$, NRaRb, C(=O)NHR$^3$ or C(=O)NRaRb wherein;
R$^1$ is hydrogen, C$_1$-C$_6$alkyl, C$_0$-C$_3$alkylenecarbocyclyl, C$_0$-C$_3$alkyleneheterocyclyl;
R$^2$ is C$_1$-C$_6$alkyl, C$_0$-C$_3$alkylenecarbocyclyl, C$_0$-C$_3$alkyleneheterocyclyl or NRaRb;
R$^3$ is C$_1$-C$_6$alkyl, C$_0$-C$_3$alkylenecarbocyclyl, C$_0$-C$_3$alkyleneheterocyclyl, —OC$_1$-C$_6$alkyl, —OC$_0$-C$_3$alkylenecarbocyclyl, —OC$_0$-C$_3$alkyleneheterocyclyl;

wherein
any alkyl, carbocyclyl or heterocyclyl in R$^1$, R$^2$ or R$^3$ are optionally substituted with 1 to 3 substituents independently selected from the group consisting of halo, oxo, cyano, azido, nitro, C$_1$-C$_6$alkyl, C$_0$-C$_3$alkylenecarbocyclyl, C$_0$-C$_3$alkyleneheterocyclyl, —C(=O)NH$_2$, Y—NRaRb, Y—O—Rb, Y—C(=O)Rb, Y—(C=O)NRaRb, Y—NRaC(=O)Rb, Y—NHSO$_p$Rb, Y—S(=O)$_p$Rb and Y—S(=O)$_p$NRaRb, Y—C(=O)ORb, Y—NRaC(=O)ORb;

Y is independently a bond or C$_1$-C$_3$alkylene;
Ra is independently H, C$_1$-C$_6$alkyl or C$_1$-C$_6$alkoxy;
Rb is independently H, C$_1$-C$_6$alkyl, C$_1$-C$_6$alkoxy, C$_0$-C$_3$alkylenecarbocyclyl or C$_0$-C$_3$alkyleneheterocyclyl;
or Ra and Rb together with the nitrogen to which they are attached join to form a heterocyclyl group;
p is independently 1 or 2;
n is 3, 4, 5 or 6;
----- denotes an optional double bond;
Rq is H or when L is CRz, Rq can also be C$_1$-C$_6$alkyl;
Ry and Ry' are independently C$_1$-C$_6$alkyl;
L is N or CRz;
Rz is H or forms a double bond with the asterisked carbon;
W is —CH$_2$—, —O—, —OC(=O)NH—, —OC(=O)—, —S—, —NH—, —NRa, —NHS(=O)$_2$—, —NHC(=O)NH— or —NHC(=O)—, —NHC(=S)NH— or a bond;
R$^8$ is a ring system containing 1 or 2 saturated, partially saturated or unsaturated rings each of which has 4-7 ring atoms and each of which has 0 to 4 hetero atoms independently selected from S, O and N, the ring system being optionally spaced from W by a C$_1$-C$_3$ alkylene group; or R$^8$ is C$_1$-C$_6$alkyl; any of which R$^8$ groups can be optionally mono-, di-, or tri-substituted with R$^9$,
wherein
R$^9$ is independently selected from the group consisting of halo, oxo, cyano, azido, nitro, C$_1$-C$_6$alkyl, C$_0$-C$_3$alkylenecarbocyclyl, C$_0$-C$_3$alkyleneheterocyclyl, —C(=O)NH$_2$, Y—NRaRb, Y—O—Rb, Y—C(=O)Rb, Y—(C=O)NRaRb, Y—NRaC(=O)Rb, Y—NHS(=O)$_p$Rb, Y—S(=O)$_p$Rb, Y—S(=O)$_p$NRaRb, Y—C(=O)ORb, Y—NRaC(O)ORb; wherein said carbocyclyl or heterocyclyl is optionally substituted with R$^{10}$; wherein
R$^{10}$ is C$_1$-C$_6$alkyl, C$_3$-C$_7$cycloalkyl, C$_1$-C$_6$alkoxy, amino, amido, sulfonyl, (C$_1$-C$_3$ alkyl)sulfonyl, nitro, hydroxy, mercapto, halo, haloalkyl, carboxyl.

2. A compound according to claim 1, with the partial structure:

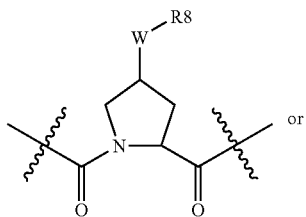

or

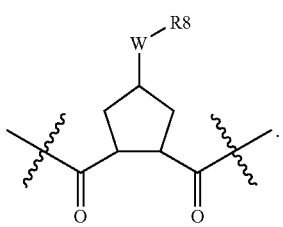

3. A compound according to claim 1, wherein n is 4 or 5.

4. A compound according to claim 1, wherein the dashed line ----- denotes a double bond.

5. A compound according to claim 1, wherein Ry and Ry are each methyl.

6. A compound according to claim 1, wherein W is —O— and $R^8$ is quinolin-4-yl, isoquinolin-1-yl, quinazolin-4-yl, or pyrimidin-4-yl, any of which is, independently, optionally mono, di, or tri substituted with methyl, ethyl, isopropyl, tert-butyl, methoxy, trifluoromethyl, trifluoromethoxy, fluoro, chloro, bromo, —$NRt^{5a}Rt^{5b}$, —$C(O)NRt^{5a}Rt^{5b}$, phenyl, methoxyphenyl, cyanophenyl, halophenyl, pyridyl, $C_{1-4}$alkylpyridyl, pyrimidinyl, morpholinyl, piperazinyl $C_{1-4}$alkylpiperazinyl, pyrrolidinyl, pyrazolyl, $C_{1-4}$alkylpyrazolyl, thiazolyl, $C_{1-4}$alkylthiazolyl, cyclopropylthiazolyl, or mono- or di$C_{1-4}$alkyl-aminothiazolyl or $C_{1-3}$alkylthiazolyl, where $Rt^{5a}$ and $Rt^{5b}$ are, independently, hydrogen, $C_{3-7}$cycloalkyl, aryl, heterocyclyl, $C_{1-6}$alkyl optionally substituted with halo, $C_{1-6}$alkoxy, cyano, halo$C_{1-6}$alkoxy, $C_{3-7}$cycloalkyl, aryl or with heterocyclyl.

7. A compound according to claim 1, wherein W is O(C═O)NH and $R^8$ is phenyl substituted with one to 3 substituents selected from $R^9$.

8. A compound according to claim 1, wherein
A is —$OR^1$, wherein R1 is hydrogen, methyl, ethyl, or tert-butyl; or
A is —$NHS(═O)_2R^2$, where $R^2$ is methyl, cyclopropyl, or phenyl; or
A is —$NHS(═O)_2NR^{5a}R^{5b}$ where $R^{5a}$ and $R^{5b}$ are, each independently, hydrogen, $C_{3-7}$cycloalkyl or $C_{1-6}$alkyl.

9. A method of treating a warm-blooded animal infected by HCV, said method comprising the administration of an antivirally effective amount of a compound according to claim 1.

10. A combination of a compound according to claim 1 with one or two anti-HCV agents.

11. A pharmaceutical composition comprising one or more compounds according to claim 1.

12. A process for preparing a compound according to claim 1, wherein said process comprises:

(a) Preparing a compound of formula (I) wherein the bond between $C_7$ and $C_8$ is a double bond, which is a compound of formula (I-c), by forming a double bond between $C_7$ and $C_8$, in particular via an olefin metathesis reaction, with concomitant cyclization to the macrocycle as outlined in the following reaction scheme:

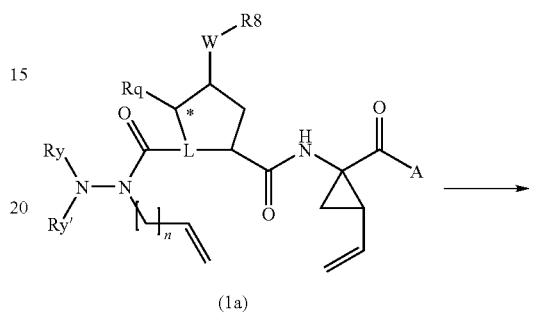

(1a)

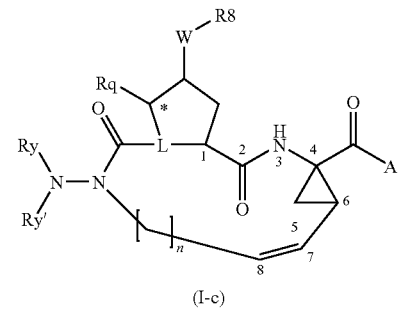

(I-c)

(b) Converting a compound of formula (1c) by a reduction of the C7-C8 double bond to a compound of formula (I-d) wherein the link between C7 and C8 in the macrocycle is a single bond, i.e. a compound of formula (I-d):

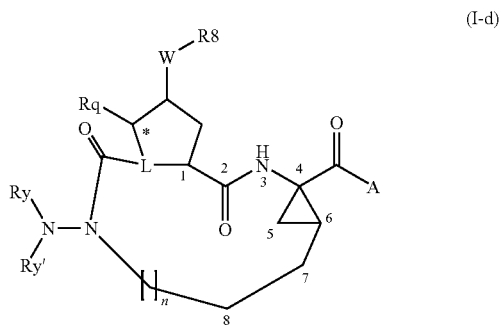

(c) preparing a compound of formula (I) wherein A represents —$NHSO_2R^2$, said compounds being represented by formula (I-k-1), by forming an amide bond between a intermediate (2a) and an sulfonylamine (2b), or preparing a compound of formula (I) wherein $R^1$ represents —$OR^1$, i.e. a compound (I-k-2), by forming an ester bond between an intermediate (2a) and an alcohol (2c) as outlined in the following scheme:

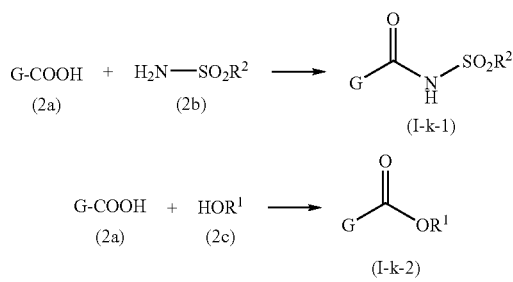

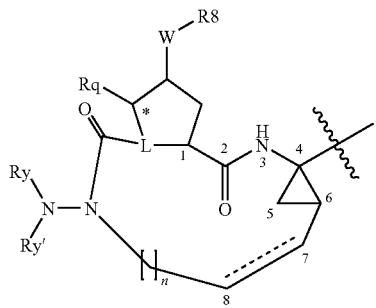

wherein G represents a group:

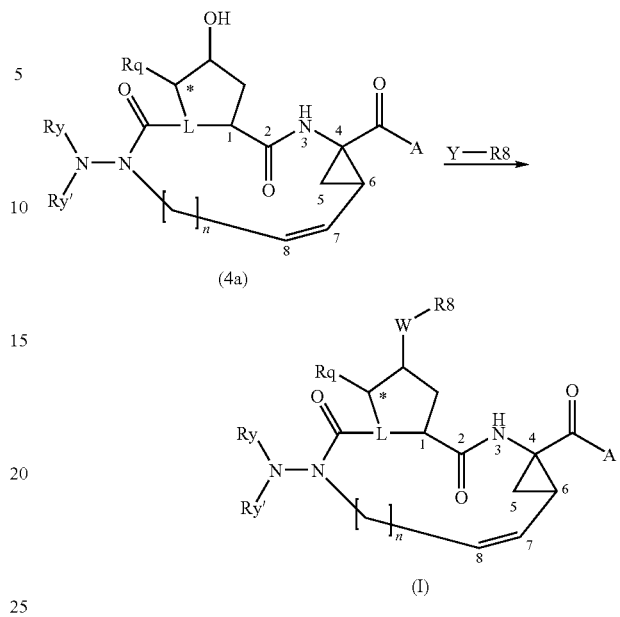

(d) reacting an intermediate (4a) with an intermediate Y—R⁸ as outlined in the following reaction scheme:

wherein Y represents hydroxy or a leaving group; which reaction in particular is an O-arylation reaction wherein Y represents a leaving group, or a Mitsunobu reaction, wherein Y represents hydroxy; and (e) preparing a salt form by reacting the free form of a compound of formula (I) with a acid or base.

* * * * *